United States Patent
Hammond et al.

(10) Patent No.: US 11,040,091 B2
(45) Date of Patent: Jun. 22, 2021

(54) CYCLE ADENOSINE MONOPHOSPHATE-INCOMPETENT ADENYLYL CYCLASE AND COMPOSITIONS AND METHODS FOR TREATING HEART FAILURE AND INCREASING CARDIAC FUNCTION

(71) Applicant: THE REGENTS OF THE UNIVERSITY OF CALIFORNIA, Oakland, CA (US)

(72) Inventors: H. Kirk Hammond, La Jolla, CA (US); Mei Hua Gao, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/893,905

(22) PCT Filed: Jun. 4, 2014

(86) PCT No.: PCT/US2014/040948
§ 371 (c)(1),
(2) Date: Nov. 24, 2015

(87) PCT Pub. No.: WO2014/197624
PCT Pub. Date: Dec. 11, 2014

(65) Prior Publication Data
US 2016/0101164 A1    Apr. 14, 2016

Related U.S. Application Data

(60) Provisional application No. 61/832,759, filed on Jun. 7, 2013.

(51) Int. Cl.
*C12N 15/861* (2006.01)
*A61K 38/51* (2006.01)
*C12N 9/88* (2006.01)

(52) U.S. Cl.
CPC ............... *A61K 38/51* (2013.01); *C12N 9/88* (2013.01); *C12Y 406/01001* (2013.01)

(58) Field of Classification Search
None
See application file for complete search history.

(56) References Cited

U.S. PATENT DOCUMENTS

2002/0103147 A1    8/2002    Hammond et al.

OTHER PUBLICATIONS

Kieserman et al., J. AMer. Heart Assoc., 2019: 14 pages.*
Copenheaver, International Search Report for PCT/US2014/040948 dated Nov. 12, 2014.
Copenheaver, International Preliminary Report on Patentability for PCT/US2014/040948 dated Nov. 12, 2014.
Gao et al, "Beneficial Effects of Adenylyl Cyclase Type 6 (AC6) Expression Persist Using a Catalytically Inactive AC6 Mutant," Molecular Pharmacology, 2011, v 79, n 3, p. 381-388.
Lai et al, "Activation of Cardiac Adenylyl Cyclase Expression Increases Function of the Failing Ischemic Heart in Mice," Journal of the American College of Cardiology, 2008, v 51, n 15, p. 1490-1497.
Sugano et al, "Activated expression of cardiac adenylyl cyclase 6 reduces dilation and dysfunction of the pressure-overloaded heart," Biochem Biophys Res Commun, 2011, v 405, n 3, p. 349-355.
Takahashi et al, "Increased Cardiac Adenylyl Cyclase Expression Is Associated With Increased Survival After Myocardial Infarction," Circulation, 2006, v 114, p. 388-396.
Sugano et al., "Activated expression of cardiac adenylyl cyclase 6 reduces dilation and dysfunction of the pressure-overloaded heart," Biochem Biophy Res Commun. Dec. 30, 2010, pp. 349-355, vol. 405, No. 3.
Gao et al., "Beneficial effects of adenylyl cyclase type 6 (AC6) expression persist using a catalytically inactive AC6 mutant," Mal Pharmacol. Dec. 2, 2010, pp. 381-388, vol. 79, No. 3.
Takahashi et al., "Increased cardiac adenylyl cyclase expression is associated with increased survival after myocardial infarction," Circulation, Jul. 24, 2006, pp. 388-396, vol. 114, No. 5.
Lai et al., "Activation of cardiac adenylyl cyclase expression increases function of the falling ischemic heart in mice," J. Am. Coll Cardiol. Apr. 15, 2008, pp. 1490-1497, vol. 51, No. 15.
International Search Report for PCT/US2014/040948, dated Nov. 12, 2014.
Guan, First Office Action for Chinese Patent application CN 2014800441905, dated Sep. 3, 2018.
Chumasov et al., "Current views on the cardiac innervation and its involvement in the regulation of systemic hemodynamics" 2012, v 11, n 1, p. 9-14.

* cited by examiner

*Primary Examiner* — Michael D Burkhart
(74) *Attorney, Agent, or Firm* — Greer, Burns & Crain, LTD.; Gregory P. Einhorn

(57) ABSTRACT

The invention provides methods for treating, ameliorating or protecting (preventing) an individual or a patient having or at risk of having heart disease or heart failure, or decreased cardiac function, comprising: providing a cyclic adenosine monophosphate-incompetent (cAMP-incompetent) adenylyl cyclase type 6 (AC6) protein or polypeptide (also called "an AC6mut"), or an AC6mut-encoding nucleic acid or a gene operatively linked to a transcriptional regulatory sequence.

15 Claims, 5 Drawing Sheets

Specification includes a Sequence Listing.

CYCLE ADENOSINE MONOPHOSPHATE-INCOMPETENT ADENYLYL CYCLASE AND COMPOSITIONS AND METHODS FOR TREATING HEART FAILURE AND INCREASING CARDIAC FUNCTION

RELATED APPLICATIONS

This application is a national phase application which claims the benefit of priority under 35 U.S.C. § 371 to Patent Convention Treaty (PCT) International Application serial number PCT/US2014/040948 filed Jun. 4, 2014, which claims the benefit of priority under 35 U.S.C. § 119(e) of U.S. Provisional Application No. 61/832,759, filed Jun. 7, 2013. The aforementioned applications are expressly incorporated herein by reference in their entirety and for all purposes.

STATEMENT AS TO FEDERALLY SPONSORED RESEARCH

This invention was made with government support under HL066941, HL081741, and HL088426 awarded by National Institutes of Health. The government has certain rights in the invention.

TECHNICAL FIELD

This invention relates generally to cellular and molecular biology, gene therapy and medicine; and more specifically, to compositions methods for treating a subject having or at risk of having heart failure or heart disease by administering a cyclic adenosine monophosphate-incompetent (cAMP-incompetent) adenylyl cyclase type 6 (AC6) protein or polypeptide (also called "an AC6mut"), or an AC6mut-encoding nucleic acid sequence.

BACKGROUND

Adenylyl cyclase, a transmembrane protein in cardiac myocytes and other cells, is the key effector molecule that transduces p-adrenergic signaling by generation of intracellular cAMP. Cyclic-AMP is the second messenger for downstream events including protein kinase A activation. Heart failure is associated with impaired cAMP production, which is tightly linked to heart function. It has been shown that increased cardiac AC type 6 (AC6), a dominant AC isoform expressed in mammalian cardiac myocytes, has protean beneficial effects on the failing left ventricle (LV). These include: 1) increased survival in cardiomyopathy and in acute myocardial infarction, 2) reduced action potential duration and facilitation of atrio-ventricular conduction associated with reduction of AV block, 3) reductions in both LV dilation and pathological hypertrophy, 4) beneficial effects on calcium handling through improved SERCA2a activity, increased phospholamban activity, and 5) increased cardiac troponin I phosphorylation.

Consequently, several drugs have been generated which increase intracellular levels of cAMP, and have been tested in patients with heart failure. However, these drugs typically increase mortality. The current dogma dictates that drugs and proteins that increase levels of intracellular cAMP are deleterious to the failing heart, and therefore, are unsuitable for the treatment of heart failure.

SUMMARY

In alternative embodiments, the invention provides methods for treating, ameliorating or protecting (preventing) an individual or a patient against heart disease or decreased cardiac function, comprising: providing a cyclic adenosine monophosphate-incompetent (cAMP-incompetent) adenylyl cyclase type 6 (AC6) protein or polypeptide (also called "an AC6mut"), or an AC6mut-encoding nucleic acid or a gene operatively linked to a transcriptional regulatory sequence; or an expression vehicle, a vector, a recombinant virus, or equivalent, having contained therein an AC6mut-encoding nucleic acid or gene, and the expression vehicle, vector, recombinant virus, or equivalent can express the an AC6mut-encoding nucleic acid or gene in a cell or in vivo; and administering or delivering the AC6mut, or the AC6mut-encoding nucleic acid or gene operatively linked to a transcriptional regulatory sequence, or the expression vehicle, vector, recombinant virus, or equivalent, to an individual or a patient in need thereof, thereby treating, ameliorating or protecting (preventing) the individual or patient against the heart disease or decreased cardiac function. In alternative embodiments, the AC6mut comprises an adenylyl cyclase (AC) polypeptide having a substitution of an uncharged or non-polar amino acid for a charged or an acidic amino acid in the catalytic core of the AC polypeptide.

In alternative embodiments, the invention provides methods, and an in vivo method for or method of:

(1) treating a subject having or at risk of having a heart disease or a heart failure;

(2) treating, ameliorating, reversing the effects of, protecting or preventing an individual or a patient against:
a heart disease,
a heart failure,
a decrease in heart function or cardiac output,
a decrease in heart function or cardiac output due to a heart infection or a heart condition,
  (3) enhancing calcium handling in intact cardiac myocytes by increasing sarcoplasmic reticulum (SR) $Ca^{2+}$ uptake and/or increased $Ca^{2+}$ transients with reduced time of relaxation in intact cardiac myocytes, (4) inhibiting the generation of intracellular cAMP levels in cardiac myocytes, (5) protecting a cardiac myocyte from a programmed cell death (apoptosis) signal, or decreasing the number of cardiac myocytes signaled to programmed cell death (apoptosis) subsequent to an apoptotic signal, or (6) in heart failure patients or in individuals having a heart infection or a heart condition resulting in a decrease in heart function or cardiac output: increasing heart function or cardiac output, reducing symptom and/or decreasing mortality; or reducing the frequency of hospitalizations for heart failure, comprising:

(a) providing:
  (i) a cyclic adenosine monophosphate-incompetent (cAMP-incompetent) adenylyl cyclase type 6 (AC6) protein or polypeptide (also called "an AC6mut"),
  wherein optionally the AC6mut is a recombinant, a synthetic, a peptidomimetic or an isolated AC6mut polypeptide or peptide; or
  (ii) a AC6mut-encoding nucleic acid or gene:
  wherein optionally the AC6mut-encoding nucleic acid or gene is operatively linked to a transcriptional regulatory sequence, wherein optionally the transcriptional regulatory sequence is a promoter and/or an enhancer, or a cardiac cell-specific promoter or a myocyte-specific promoter; or
  wherein optionally the AC6mut-encoding nucleic acid or gene is operatively linked to a transcriptional regulatory sequence, and optionally the AC6mut-encoding nucleic acid or gene is contained in a delivery vehicle, a vector, an expression vector, a recombinant virus, or an equivalent, and the delivery vehicle, expression vehicle, vector, recombinant virus, or equivalent can express the AC6mut-encoding nucleic acid or gene in a cell or in vivo, wherein optionally the cell is a cardiac cell or a myocyte;

wherein the AC6mut does not catalyze the breakdown of ATP to cAMP, or has impaired ability to catalyze the breakdown of ATP to cAMP, and optionally the impaired ability to catalyze the breakdown of ATP to cAMP is defined as the AC6mut having only about 1%, 10%, 20%, 30%, 40%, 50%, 60%, 70%, 80%, 90% or 95% of the ATP to cAMP catalytic activity of wild type AC6, and when the AC6mut is expressed in a cardiac myocyte in vivo left ventricular (LV) function is not affected or does not decrease or LV function is substantially not affected or decreased, and optionally AC6mut expression in a cardiac myocyte increases sarcoplasmic reticulum $Ca^{2+}$ uptake, and optionally AC6mut expression in a cardiac myocyte reduces the EC50 for SERCA2a activation, and optionally AC6mut expression in a cardiac myocyte reduces expression of a phospholamban protein, and optionally the substitution inhibits $Mg^{2+}$ binding and alters the efficiency of Gsα-mediated activation of the catalytic core;

(b) delivering or administering the AC6mut, or the AC6mut-encoding nucleic acid or gene, to a cardiac cell or a cardiac myocyte, or expressing the AC6mut in a cardiac cell or a cardiac myocyte, or expressing the AC6mut-encoding nucleic acid or gene in a cardiac cell or a cardiac myocyte, wherein optionally the AC6mut-encoding nucleic acid is operatively linked to a transcriptional regulatory sequence, or optionally the delivery vehicle, vector, expression vector, recombinant virus, or equivalent, is delivered or administered to a cardiac myocyte cell, or to an individual or a patient in need thereof, and optionally the delivering or administering of the AC6mut-encoding nucleic acid or gene to the cardiac cell or myocyte in vivo is a targeted delivery to a heart muscle or a cardiac myocyte, or comprises direct delivery or administration to a heart, or comprises an intracardiac injection or an infusion, thereby:

treating the subject having or at risk of having a heart disease or a heart failure, treating, ameliorating or protecting (preventing) an individual or a patient against a heart disease, a heart failure, a decrease in heart function or cardiac output, a decrease in heart function or cardiac output due to a heart infection or a heart condition, enhancing calcium handling in intact cardiac myocytes by increasing sarcoplasmic reticulum (SR) $Ca^{2+}$ uptake and/or increased $Ca^{2+}$ transients with reduced time of relaxation in intact cardiac myocytes, inhibiting the generation of intracellular cAMP levels in cardiac myocytes, protecting a cardiac myocyte from a programmed cell death (apoptosis) signal, or decreasing the number of cardiac myocytes signaled to programmed cell death (apoptosis) subsequent to an apoptotic signal, or in heart failure patients or in individuals having a heart infection or a heart condition resulting in a decrease in heart function or cardiac output: increasing heart function or cardiac output, reducing symptom and/or decreasing mortality.

In alternative embodiments, the AC6mut comprises an adenylyl cyclase (AC) polypeptide having a substitution of an uncharged or non-polar amino acid for a charged or an acidic amino acid in the catalytic core of the AC polypeptide, wherein optionally the uncharged or non-polar amino acid is an alanine (Ala), and optionally the acidic amino acid is an aspartic acid (Asp), or optionally the uncharged or non-polar amino acid is an Ala and the acidic amino acid is an Asp.

In alternative embodiments, the AC6mut comprises:

a murine adenylyl cyclase (AC) polypeptide having a substitution of an Ala for an Asp at position 426 in the catalytic core of the AC polypeptide based on SEQ ID NO:16, where SEQ ID NO:17 is the polypeptide amino acid sequence after the D=>A substitution (SEQ ID NO:16 is the amino acid sequence before the D=>A substitution); or a murine AC6mut polypeptide having a substitution of an alanine, or Ala for an Asp at position 436 in the catalytic core of the AC polypeptide based on SEQ ID NO:11, where SEQ ID NO:12 is the polypeptide amino acid sequence after the D=>A substitution (SEQ ID NO:11 is the amino acid sequence before the D=>A substitution).

In alternative embodiments, the AC6 is a mammalian AC6 polypeptide, or the AC6 is a human AC6 polypeptide. In alternative embodiments, the human AC6 polypeptide comprises a human AC6 polypeptide having a substitution of an Ala for an Asp at position 426 in the catalytic core of the AC polypeptide based on SEQ ID NO:10, where SEQ ID NO:13 is the polypeptide amino acid sequence after the D=>A substitution (SEQ ID NO:10 is the amino acid sequence before the D=>A substitution).

In alternative embodiments of the methods:

(a) the AC6mut-encoding nucleic acid or gene is stably inserted into a chromosome of a cell;

(b) the delivery vehicle, vector, expression vector, recombinant virus, or equivalent, is or comprises: an adeno-associated virus (AAV); a recombinant AAV virus or vector; an AAV virion, or an adenovirus vector, or any pseudotype, hybrid or derivative thereof;

(c) the method of (b), wherein the adeno-associated virus (AAV), recombinant AAV virus or vector, AAV virion, or adenovirus vector, is or comprises: an AAV serotype AAV5, AAV6, AAV7, AAV8 or AAV9; a rhesus macaque AAV (AAVrh), or an AAVrh10; or any hybrid or derivative thereof;

(d) the AC6mut-encoding nucleic acid or gene is operatively linked to a regulated or inducible transcriptional regulatory sequence;

(e) the method of (d), wherein the regulated or inducible transcriptional regulatory sequence is a regulated or inducible promoter;

(f) the method of any of (a) to (e), wherein administering the AC6mut-encoding nucleic acid or gene operatively linked to a transcriptional regulatory sequence, or the delivery vehicle, vector, expression vector, recombinant virus, or equivalent, to an individual or a patient in need thereof results in: targeted delivery and expression of the AC6mut in a cardiac myocyte, or a AC6mut being released into the bloodstream or general circulation; or (g) the method of any of (a) to (f), wherein a disease, infection or condition responsive to an increased AC6mut level in vivo is a cardiac contractile dysfunction; a congestive heart failure (CHF); a cardiac fibrosis; a cardiac myocyte disease; a cardiac myocyte dysfunction or a cardiac myocyte apoptosis.

In alternative embodiments of the methods:

(a) the AC6mut-encoding nucleic acid or gene operatively linked to the transcriptional regulatory sequence; or the delivery vehicle, vector, expression vector, recombinant virus, or equivalent, is administered or delivered to the individual or a patient in need thereof, by oral administration, by intramuscular (IM) injection, by intravenous (IV) injection, by subcutaneous (SC) injection, by intradermal injection, by intrathecal injection, by intra-arterial (IA) injection, by intracoronary or intracardiac injection, by intraocular injection or application, by inhalation, or by a biolistic particle delivery system, or by using a "gene gun", air pistol or a HELIOS™ gene gun (Bio-Rad Laboratories, Hercules, Calif.), wherein optionally the AC6mut-encoding nucleic acid or gene is delivered by intravenous (IV) injection of an AAV vector, or AAV-9 vector; or (b) the AC6mut-encoding nucleic acid or gene operatively linked to the transcriptional regulatory sequence; or the expression vehicle, vector, recombinant virus, or equivalent, is administered or delivered to the individual or a patient in need thereof, by introduction into any cell, organ, tissue or fluid space within the body that is adjacent to or is drained by the bloodstream, such that the encoded AC6mut protein may be secreted from cells in the tissue and released into the bloodstream.

In alternative embodiments of the methods:

(a) the individual, patient or subject is administered a stimulus or signal that induces expression of the AC6mut-expressing nucleic acid or gene, or induces or activates a promoter (e.g., a promoter operably linked to the AC6mut-expressing nucleic acid or gene) that induces expression of or up-regulates expression of the AC6mut-expressing nucleic acid or gene;

(b) the individual, patient or subject is administered a stimulus or signal that induces synthesis of an activator of a promoter, wherein optionally the promoter is an AC gene promoter, or a myocyte cell-specific promoter;

(c) the individual, patient or subject is administered a stimulus or signal that induces synthesis of a natural or a synthetic activator of the AC6mut-expressing nucleic acid or gene or the AC6mut-expressing nucleic acid or gene-specific promoter, wherein optionally the natural activator is an endogenous transcription factor;

(d) the method of (c), wherein the synthetic activator is a zinc-finger DNA binding protein designed to specifically and selectively turn on an endogenous or exogenous target gene, wherein optionally the endogenous target is an AC6mut-expressing nucleic acid or gene or an activator of an AC6mut, or a AC6mut-expressing nucleic acid or gene, or an activator of a promoter operatively linked to a AC6mut-expressing nucleic acid or gene;

(e) the method of any of (a) to (c), wherein the stimulus or signal comprises a biologic, a light, a chemical or a pharmaceutical stimulus or signal;

(f) the individual, patient or subject is administered a stimulus or signal that stimulates or induces expression of a post-transcriptional activator of an AC6mut, or a AC6mut-expressing nucleic acid or gene, or an activator of a promoter operatively linked to a AC6mut-expressing nucleic acid or gene, or (g) the individual, patient or subject is administered a stimulus or signal that inhibits or induces inhibition of a transcriptional repressor or a post-transcriptional repressor of a AC6-expressing nucleic acid or gene.

In alternative embodiments: the chemical or pharmaceutical that induces expression of the AC6mut, or the AC6mut-expressing nucleic acid or gene, or induces expression of the regulated or inducible promoter operatively linked to the AC6mut-expressing nucleic acid or gene, is or comprises an oral antibiotic, a doxycycline or a rapamycin; or a tet-regulation system using doxycycline is used to induce expression of the AC6mut, or the AC6mut-expressing nucleic acid or gene, or an equivalent thereof.

In alternative embodiments: the AC6mut, or the AC6mut-expressing nucleic acid or gene, or the delivery vehicle, vector, expression vector, recombinant virus, or equivalent, is formulated in or as a lyophilate, a liquid, a gel, a hydrogel, a powder, a spray, an ointment, or an aqueous or a saline formulation.

In alternative embodiments: the AC6mut, or the AC6mut-expressing nucleic acid or gene or the delivery vehicle, vector, expression vector, recombinant virus, or equivalent, comprises, or is formulated in, a vesicle, a hydrogel, a gel, a liposome, a nanoliposome, a nanoparticle or a nanolipid particle (NLP).

In alternative embodiments: the AC6mut, or the AC6mut-expressing nucleic acid or gene or the delivery vehicle, vector, expression vector, recombinant virus, or equivalent, is formulated in an isolated or cultured cell, and optionally the cell is a mammalian cell, a cardiac cell, or a human cell, a non-human primate cell, a monkey cell, a mouse cell, a rat cell, a guinea pig cell, a rabbit cell, a hamster cell, a goat cell, a bovine cell, an equine cell, an ovine cell, a canine cell or a feline cell.

In alternative embodiments: the AC6mut, or the AC6mut-expressing nucleic acid or gene, or the delivery vehicle, vector, expression vector, recombinant virus, or equivalent, is formulated as a pharmaceutical or sterile.

In alternative embodiments: the AC6mut, or the AC6mut-expressing nucleic acid or gene or the delivery vehicle, vector, expression vector, recombinant virus, or equivalent, is formulated or delivered with, on, or in conjunction with a product of manufacture, an artificial organ or an implant.

In alternative embodiments: the AC6mut, or the AC6mut-expressing nucleic acid or gene or the delivery vehicle, vector, expression vector, recombinant virus, or equivalent expresses a AC6mut polypeptide in vitro or ex vivo.

In alternative embodiments, the invention provides methods for treating, ameliorating, reversing, protecting or preventing an individual or a patient against a AC6mut-responsive pathology, infection, disease, illness, or condition, comprising practicing a method of the invention.

In alternative embodiments, the invention provides methods for treating, ameliorating, reversing, protecting or preventing a cardiopathy or a cardiovascular disease in an individual or a patient in need thereof, comprising practicing a method of the invention. In alternative embodiments, the cardiopathy or cardiovascular disease comprises: a coronary artery disease (CAD); an atherosclerosis; a thrombosis; a restenosis; a vasculitis, an autoimmune or a viral vasculitis; a polyarteritis nodosa; a Churg-Strass syndrome; a Takayasu's arteritis; a Kawasaki Disease; a Rickettsial vasculitis; an atherosclerotic aneurism; a myocardial hypertrophy; a congenital heart disease (CHD); an ischemic heart disease; an angina; an acquired valvular or an endocardial disease; a primary myocardial disease; a myocarditis; an arrhythmia; a transplant rejection; a metabolic myocardial disease; a myocardiomyopathy; a congestive, a hypertrophic or a restrictive cardiomyopathy; and/or, a heart transplant.

In alternative embodiments, the invention provides uses comprising:

an AC6mut; an AC6mut-expressing nucleic acid or gene; a delivery vehicle, a vector, an expression vector, a recombinant virus, or equivalent; an adeno-associated virus (AAV); a recombinant AAV virus or vector; or an adenovirus vector, or any pseudotype, hybrid or derivative thereof, as set forth in any of claims 1 to 16, wherein optionally the AAV or recombinant AAV virus or vector comprises an AAV serotype AAV5, AAV6, AAV7, AAV8 or AAV9; a rhesus macaque AAV (AAVrh), or an AAVrh10; or any hybrid or derivative thereof, or an AC6mut-expressing cell or cardiac myocyte, in the preparation of a medicament for:

(1) treating a subject having or at risk of having a heart disease or a heart failure;

(2) treating, ameliorating, reversing the effects of, protecting or preventing an individual or a patient against:
  a heart disease,
  a heart failure,
  a decrease in heart function or cardiac output,
  a decrease in heart function or cardiac output due to a heart infection or a heart condition, (3) enhancing calcium handling in intact cardiac myocytes by increasing sarcoplasmic reticulum (SR) $Ca^{2+}$ uptake and/or increased $Ca^{2+}$ transients with reduced time of relaxation in intact cardiac myocytes, (4) inhibiting the generation of intracellular cAMP levels in cardiac myocytes, (5) protecting a cardiac myocyte from a programmed cell death (apoptosis) signal, or decreasing the number of cardiac myocytes signaled to programmed cell death (apoptosis) subsequent to an apoptotic signal, (6) in heart failure patients or in individuals having a heart infection or a heart condition resulting in a decrease in heart function or cardiac output: increasing heart function or cardiac output, reducing symptom and/or decreasing mortality; or reducing the frequency of hospitalizations for heart failure;

(7) a cardiopathy or a cardiovascular disease; or (8) a coronary artery disease (CAD); an atherosclerosis; a thrombosis; a restenosis; a vasculitis, an autoimmune or a viral vasculitis; a polyarteritis nodosa; a Churg-Strass syndrome; a Takayasu's arteritis; a Kawasaki Disease; a Rickettsial vasculitis; an atherosclerotic aneurism; a myocardial hypertrophy; a congenital heart disease (CHD); an ischemic heart disease; an angina; an acquired valvular or an endocardial disease; a primary myocardial disease; a myocarditis; an arrhythmia; a transplant rejection; a metabolic myocardial disease; a myocardiomyopathy; a congestive, a hypertrophic or a restrictive cardiomyopathy; and/or, a heart transplant.

In alternative embodiments, therapeutic formulations as used or as set forth herein, or as in any methods of the invention, for use in the treatment of or for:

(1) a heart disease, a heart failure, a decrease in heart function or cardiac output, a decrease in heart function or cardiac output due to a heart infection or a heart condition, (2) enhancing calcium handling in intact cardiac myocytes by increasing sarcoplasmic reticulum (SR) $Ca^{2+}$ uptake and/or increased $Ca^{2+}$ transients with reduced time of relaxation in intact cardiac myocytes, (3) inhibiting the generation of intracellular cAMP levels in cardiac myocytes, (4) protecting a cardiac myocyte from a programmed cell death (apoptosis) signal, or decreasing the number of cardiac myocytes signaled to programmed cell death (apoptosis) subsequent to an apoptotic signal, (5) in heart failure patients or in individuals having a heart infection or a heart condition resulting in a decrease in heart function or cardiac output: increasing heart function or cardiac output, reducing symptom and/or decreasing mortality; or reducing the frequency of hospitalizations for heart failure;

(6) a cardiopathy or a cardiovascular disease; or (7) a coronary artery disease (CAD); an atherosclerosis; a thrombosis; a restenosis; a vasculitis, an autoimmune or a viral vasculitis; a polyarteritis nodosa; a Churg-Strass syndrome; a Takayasu's arteritis; a Kawasaki Disease; a Rickettsial vasculitis; an atherosclerotic aneurism; a myocardial hypertrophy; a congenital heart disease (CHD); an ischemic heart disease; an angina; an acquired valvular or an endocardial disease; a primary myocardial disease; a myocarditis; an arrhythmia; a transplant rejection; a metabolic myocardial disease; a myocardiomyopathy; a congestive, a hypertrophic or a restrictive cardiomyopathy; and/or, a heart transplant.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

FIG. 1A schematically illustrates a diagram depicting the site of substitution of alanine (ala) for aspartic acid (asp) (a D=>A substitution) at position 426 (position number based on SEQ ID NO:17, where SEQ ID NO:16 is the sequence before the D=>A substitution) in the C1 domain (intracellular loop) in the construction of an exemplary murine AC6mut of the invention;

FIG. 1B graphically illustrates AC6mut mRNA expression as assessed by qRT-PCR using primers common to endogenous AC6 and transgene AC6mut;

FIG. 1C illustrates an immunoblot detecting AC6mut protein using anti-AC5/6 antibody and confirmed using anti-AU1 tag antibody;

FIG. 1D graphically illustrates cyclic AMP production in isolated cardiac myocytes from AC6mut and control mice, before (Basal) and after stimulation with isoproterenol, as measured by cAMP Enzyme immunoassay;

FIG. 1E illustrates a double immunofluorescence staining of AC6mut protein in cardiac myocytes isolated from AC6mut vs control mice using anti-AU1 antibody (red); anti-caveolin 3 (Cav-3) antibody (green, for caveolae); anti-protein disulphide-isomerase (PDI) antibody (green, for sarcoplasmic reticulum); anti-lamin A antibody (green, for nuclear envelope), and anti-voltage dependent anion selective channel protein (VDAC) antibody (green, for mitochondria); Nucleus is blue;

as discussed in detail in Example 1, below.

Figure 2:
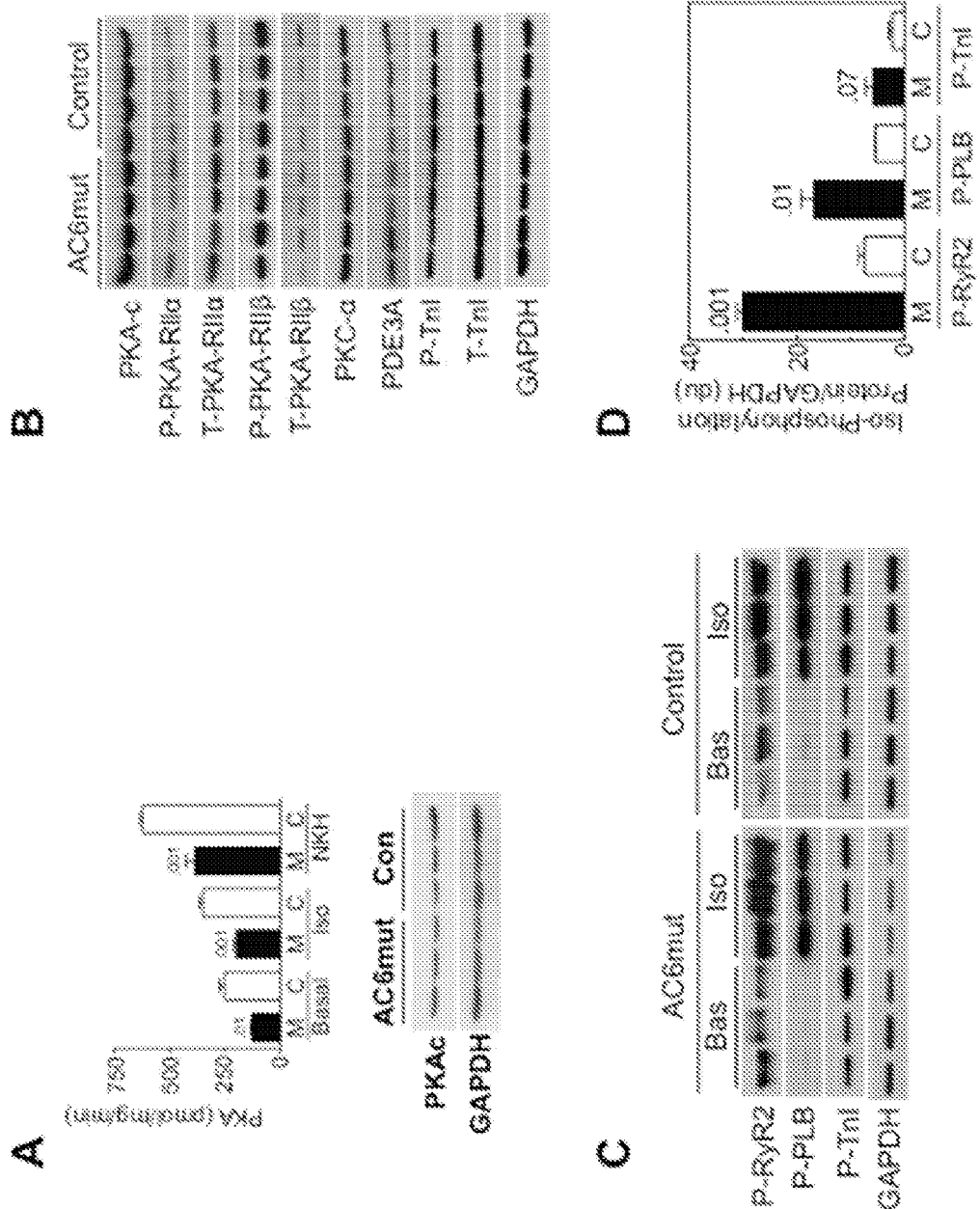

FIG. 2 illustrates the activities and expression of PKA, PKS and PDE:

FIG. 2A Upper Graph graphically illustrates levels of PKA activity in isolated cardiac myocytes without stimulation (Basal) or stimulated with isoproterenol or NKH477;

and FIG. 2A Lower illustration illustrates a gel immunoblot showing PKA protein in left ventricle (LV) homogenates;

FIG. 2B illustrates immunoblots showing the phosphorylation of key signaling proteins using left ventricular homogenates from AC6mut and control mice; shown are phospho (P) and Total (T) PKA regulatory subunits II-α and II-β, PKCα, phosphor-diesterase type 3A (PDE3A), phospho-troponin I (P22/23-TnI), and total TnI;

FIG. 2C illustrates immunoblots showing the phosphorylation of RyR2, PLB and TnI before and after isoproterenol stimulation was assessed in cultured cardiac myocytes isolated from each group;

FIG. 2D graphically illustrates the data from FIG. 2C indicating that isoproterenol stimulation in AC6mut mice was associated with increased phosphorylation of RyR2, PLB, and TnI in cardiac myocytes; data is normalized for loading (GAPDH);

as discussed in detail in Example 1, below.

Figure 3:
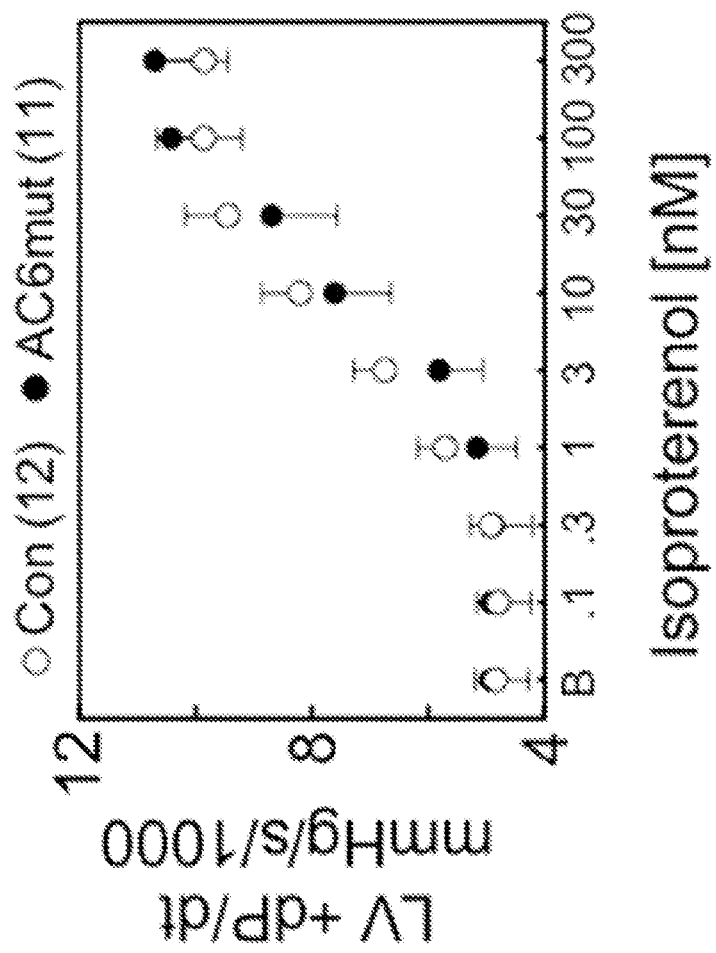

FIG. 3 graphically illustrates Left Ventricular Contractile Function: isolated hearts from AC6mut TG mice (closed circles) showed preserved LV dP/dt in response to isoproterenol stimulation through a wide range of isoproterenol doses; open circles represent transgene negative control mice; as discussed in detail in Example 1, below.

Figure 4:
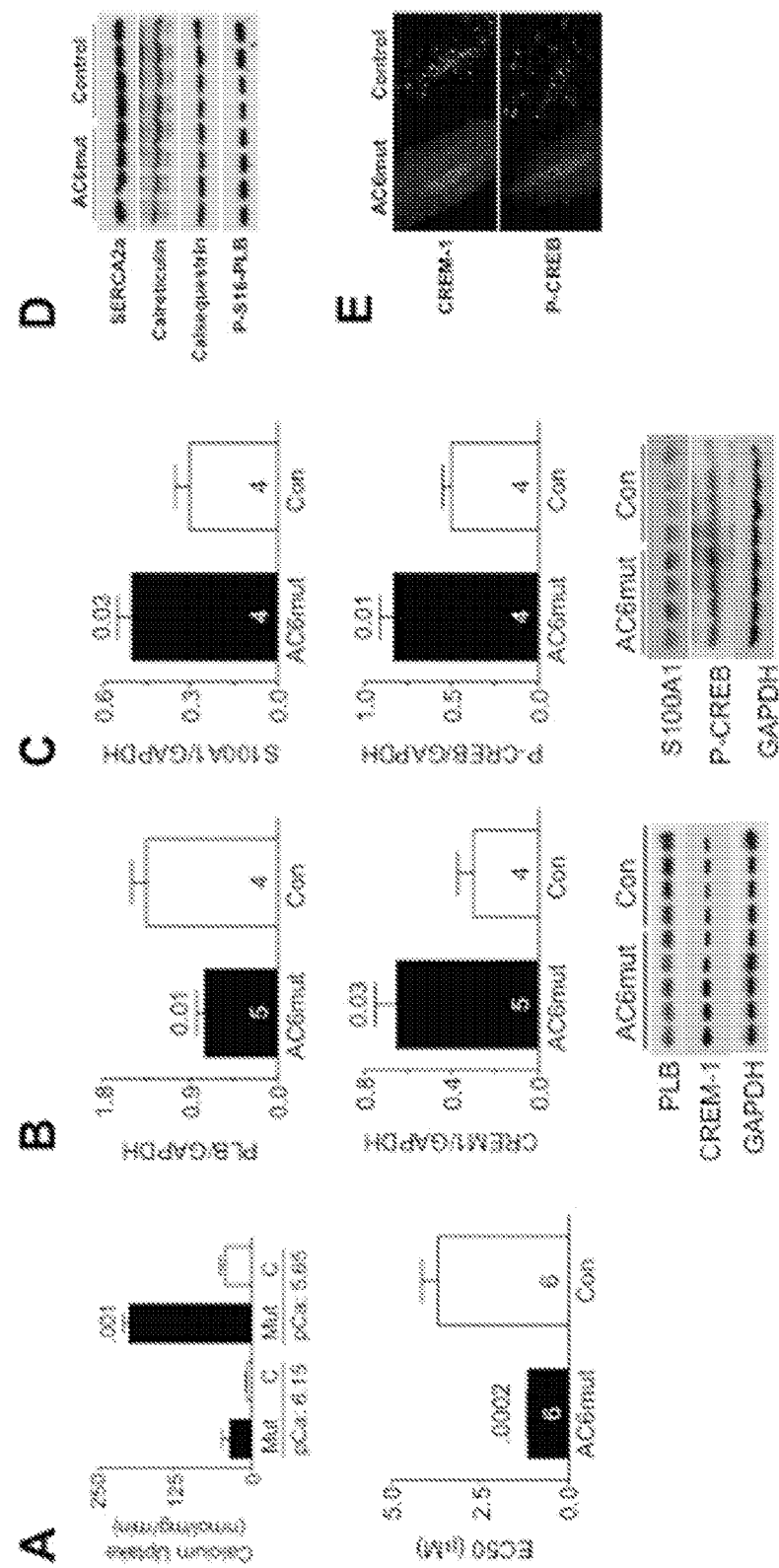

FIG. 4 illustrates SR $Ca^{2+}$ uptake, $Ca^{2+}$ signaling proteins, and transcriptional factors:

FIG. 4A Upper graph, graphically illustrates $Ca^{2+}$ uptake activity in pooled LV samples from AC6mut and TG negative sibling control mice; and FIG. 4A Lower graph, graphically illustrates expression of AC6mut decreased SERCA2a affinity for $Ca^{2+}$;

FIG. 4B Upper graph graphically illustrates AC6mut expression was associated with decreased LV phospholamban (PLB) expression; and FIG. 4B Lower graph graphically illustrates AC6mut expression was associated with increased LV CREM-1 protein expression; and FIG. 4B lower illustration illustrates immunoblots of the gels showing protein levels; data is normalized for loading (GAPDH);

FIG. 4C Upper graph graphically illustrates AC6mut expression was associated with increased LV S100A1 protein expression; and FIG. 4C Lower graph graphically illustrates AC6mut expression was associated with increased LV P133-CREB protein expression; and FIG. 4C lower illustration illustrates immunoblots of the gels showing protein levels; data is normalized for loading (GAPDH);

FIG. 4D illustrates immunoblots of the gels showing AC6mut expression did not affect LV expression of SERCA2a, calreticulin, calsequestrin or phospho-S16-PLB proteins;

FIG. 4E illustrates a double immunofluorescence staining of AC6mut protein in isolated cardiac myocytes from AC6mut and control mice using anti-AU1 antibody (red) and anti-CREM-1 antibody (green) or anti-AU1 and anti-phospho-CREB (S133, green); nucleus was showing in blue;

as discussed in detail in Example 1, below.

Figure 5:
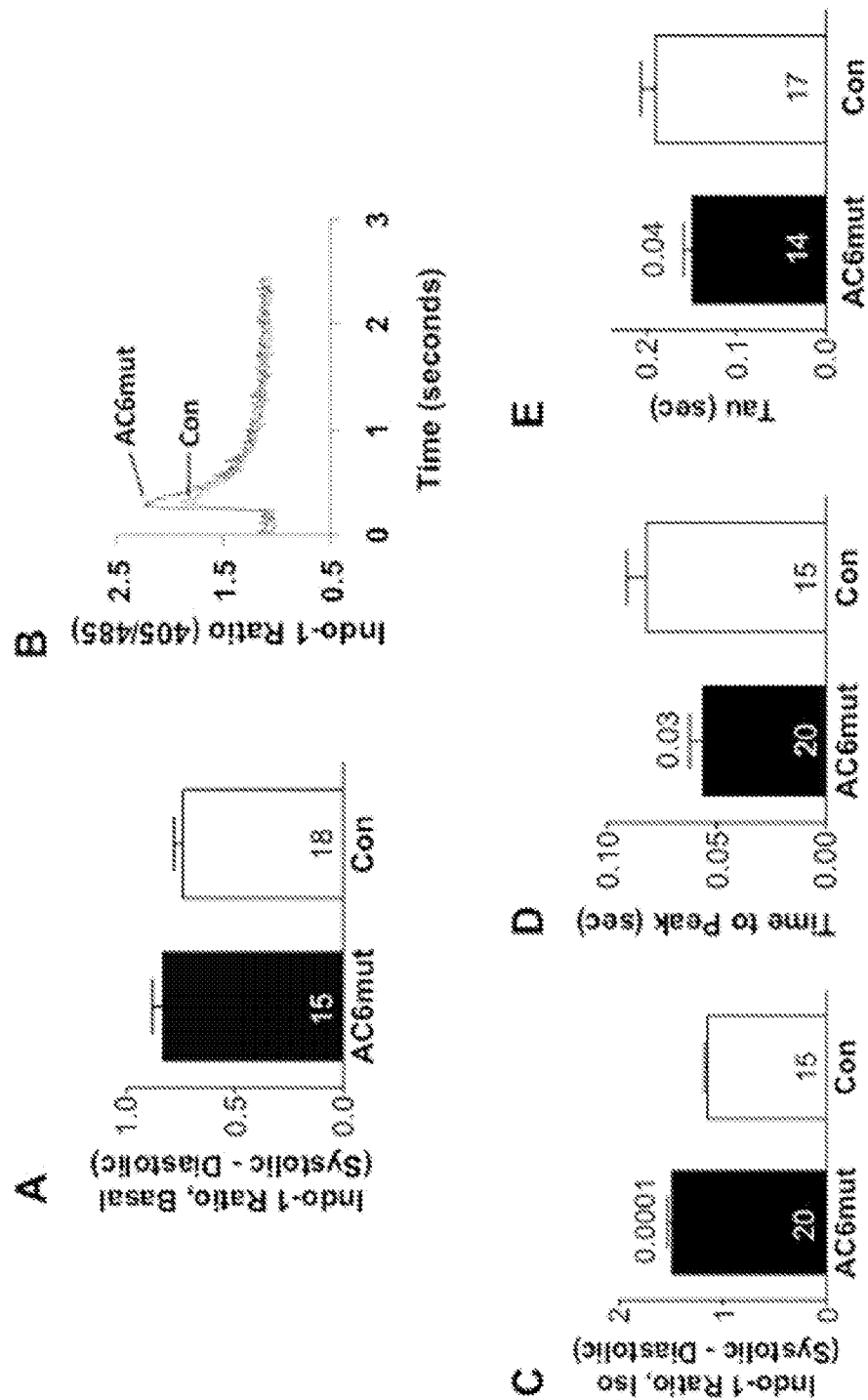

FIG. 5 illustrates cytosolic $Ca^{2+}$ transients in isolated cardiac myocytes from AC6mut and control mice:

FIG. 5A graphically illustrates data showing that basal $Ca^{2+}$ released (systolic-diastolic $Ca^{2+}$) showed no group difference between AC6mut and control;

FIG. 5B graphically illustrates data showing that representative Indo-1 $Ca^{2+}$ transient recordings in cardiac myocytes stimulated with isoproterenol were higher in cardiac myocytes from AC6mut mice; summary data are displayed in FIG. 5C;

FIG. 5C graphically illustrates data showing that $Ca^{2+}$ released in the presence of isoproterenol was increased in cardiac myocytes from AC6mut mice;

FIG. 5D graphically illustrates data showing that time-to-peak $Ca^{2+}$ transient in the presence of isoproterenol was decreased in cardiac myocytes from AC6mut mice;

FIG. 5E graphically illustrates data showing that time to 50% relaxation (tau) in the presence of isoproterenol was decreased in cardiac myocytes from AC6mut mice; as discussed in detail in Example 1, below.

Like reference symbols in the various drawings indicate like elements.

DETAILED DESCRIPTION

The invention provides compositions and in vivo and ex vivo methods comprising administration of a cyclic adenosine monophosphate-incompetent (cAMP-incompetent) adenylyl cyclase type 6 (AC6) protein or polypeptide (also called "an AC6mut"), or an AC6mut-encoding nucleic acid or a gene to treat, ameliorate or protect (as a preventative or a prophylaxis) individuals with a heart disease, a decreased cardiac function or output, or a heart infection or a condition responsive to decreased cAMP, increased sarcoplasmic reticulum (SR) $Ca^{2+}$ uptake and/or increased $Ca^{2+}$ transients with reduced time of relaxation in intact cardiac myocytes in vivo.

In alternative embodiments, the invention provides an AC6mut that inhibits or substantially reduces amounts of, or does not catalyze generation of, intracellular cAMP. In alternative embodiments, the AC6mut of the invention alters intracellular signaling in a manner that 1) enhances calcium handling in intact cardiac myocytes, 2) inhibits generation of intracellular cAMP levels in cardiac myocytes, and 3) protects cardiac myocytes from programmed cell death (apoptosis). In alternative embodiments, when the AC6mut is expressed in or delivered to the failing hearts of patients, heart function increases, symptoms are reduced, and mortality decreases. Therefore, delivery of the AC6mut of the invention to the heart increases cardiac function with no deleterious effects due to cAMP generation. Thus, in alternative embodiments, the invention provides an ideal therapy for heart failure and decrease heart function.

In alternative embodiments, the invention provides compositions and methods for the delivery and expression (e.g., a controlled expression) of an AC6mut-encoding nucleic acid or gene, or an expression vehicle (e.g., vector, recombinant virus, and the like) comprising (having contained therein) an AC6mut-encoding nucleic acid or gene, that results in an AC6mut protein selectively expressed in a cardiac myocyte, or only delivered to cardiac myocytes, or alternatively, released into the bloodstream or general circulation where it can have a beneficial effect on in the body, e.g., such as the heart in the case of treating cardiovascular disease.

In alternative embodiments, the invention provides delivery vehicles, vectors, expression vectors, recombinant viruses and the like for in vivo expression of an AC6mut-encoding nucleic acid or gene to practice the methods of this invention. In alternative embodiments, the delivery vehicles, vectors, expression vectors, recombinant viruses and the like expressing the AC6mut or the AC6mut nucleic acid or gene can be delivered by intramuscular (IM) injection, direct injection into the heart, by intravenous (IV) injection, by subcutaneous injection, by inhalation, by a biolistic particle delivery system (e.g., a so-called "gene gun"), and the like, e.g., as an outpatient, e.g., during an office visit.

In alternative embodiments, AC6mut-encoding nucleic acids or genes (for example, including delivery vehicles (such as e.g., liposomes), vectors, expression vectors, recombinant viruses and the like carrying them as a "payload") are targeted to myocytes, cardiac myocytes or delivered directly to cardiac myocytes for directed cAMP-incompetent AC expression, or expression directly in the target heart organ.

In alternative embodiments, this "peripheral" mode of delivery, e.g., delivery vehicles, vectors, expression vectors, recombinant viruses and the like, are injected IM or IV, can circumvent problems encountered when genes or nucleic acids are expressed directly in an organ (e.g., the heart, lung or kidney) itself. Sustained secretion of a desired AC6mut protein(s), or delivery vehicles, vectors, expression vectors, recombinant viruses and the like, in the bloodstream or general circulation also circumvents the difficulties and expense of administering proteins, delivery vehicles, vectors, expression vectors, recombinant viruses and the like, by infusion, which can be particularly problematic for many proteins, delivery vehicles, vectors, expression vectors, recombinant viruses and the like, which exhibit very short half lives in the body.

In alternative embodiments, the invention provides methods for being able to turn on and turn off AC6mut-expressing nucleic acid or gene expression easily and efficiently for tailored treatments and insurance of optimal safety.

In alternative embodiments, the AC6mut protein or proteins expressed by the AC6mut-expressing nucleic acid(s) or gene(s) have a beneficial or favorable effects (e.g., therapeutic or prophylactic) on a tissue or an organ, e.g., the heart, blood vessels, lungs, kidneys, or other targets, even though secreted into the blood or general circulation at a distance (e.g., anatomically remote) from their site or sites of action.

In an exemplary embodiment of the invention AC6mut-expressing nucleic acids or genes encoding cAMP-incompetent AC are used to practice methods of this invention, including but not limited to, e.g., treating a heart disease, a heart failure, a congestive heart failure (CHF), any decrease in cardiac output or function, or any combination thereof.

For example, in alternative embodiments, delivery vehicles, vectors, expression vectors, recombinant viruses and the like, e.g., a long-term virus or viral vector, can be injected, e.g., in a systemic vein (e.g., IV), or by intramuscular (IM) injection, by inhalation, or by a biolistic particle delivery system (e.g., a so-called "gene gun"), e.g., as an outpatient, e.g., in a physician's office. In alternative embodiments, days or weeks later (e.g., four weeks later), the individual, patient or subject is administered (e.g., inhales, is injected or swallows), a chemical or pharmaceutical that induces expression of the AC6mut-expressing nucleic acids or genes; for example, an oral antibiotic (e.g., doxycycline or rapamycin) is administered once daily (or more or less often), which will activate the expression of the gene. In alternative embodiments, after the "activation", or inducement of expression (e.g., by an inducible promoter) of the nucleic acid or gene, an AC6mut protein is synthesized and released into the subject's circulation (e.g., into the blood), and subsequently has favorable physiological effects, e.g., therapeutic or prophylactic, that benefit the individual or patient (e.g., benefit heart function). When the physician or subject desires discontinuation of the treatment, the subject simply stops taking the activating chemical or pharmaceutical, e.g., antibiotic.

In alternative embodiments, applications of the present invention include: the treatment of severe, low ejection fraction heart failure; the treatment of pulmonary hypertension; the treatment of heart failure with preserved ejection fraction; replacement of current therapies that require hospitalization and sustained intravenous infusions of vasoactive peptides for the treatment of a pulmonary hypertension and heart failure; and, the treatment of other conditions in which controlled expression of an AC6mut or an AC6mut nucleic acid or gene to promote favorable effects in the body.

Generating and Manipulating Nucleic Acids

In alternative embodiments, to practice the methods of the invention, the invention provides isolated, synthetic and/or recombinant nucleic acids or genes encoding AC6mut polypeptides. In alternative embodiments, to practice the methods of the invention, the invention provides AC6mut-expressing nucleic acids or genes in recombinant form in an (e.g., spliced into) an expression vehicle for in vivo expression, e.g., in a vector, e.g., an AAV, or any pseudotype, hybrid or derivative thereof, or a recombinant virus.

In alternative embodiments, a mammalian, e.g., human or murine, AC6mut can be used to practice this invention, wherein the AC6mut comprises an adenylyl cyclase (AC) polypeptide having a substitution of an uncharged or non-polar amino acid for a charged or an acidic amino acid in the catalytic core of the AC polypeptide. The catalytic core (also called the catalytic region 1 (C1)) of human AC6 polypeptide (SEQ ID NO:10) is from amino acid residue 307 to 675. The catalytic core of murine AC6 polypeptide (SEQ ID NO:11) is from amino acid residue 315 to 683.

In alternative embodiments, the uncharged or non-polar amino acid is an alanine (Ala), and optionally the acidic amino acid is an aspartic acid (Asp), or optionally the uncharged or non-polar amino acid is an Ala and the acidic amino acid is an Asp.

In alternative embodiments, the invention provides a (murine) AC6mut polypeptide (SEQ ID NO:12) comprising a murine adenylyl cyclase (AC) polypeptide having a substitution of an alanine, or Ala (or "A") for an aspartic acid, or Asp (or "D") at position 436 in the catalytic core of the AC polypeptide; i.e., in this embodiment, the murine adenylyl cyclase (AC) polypeptide has a substitution D=>A, or of an Ala for an Asp, at position 436 in the catalytic core of the murine AC polypeptide (SEQ ID NO:11 is the amino acid sequence before the D=>A substitution).

In alternative embodiments, the invention provides a (murine) AC6mut polypeptide (SEQ ID NO:17) comprising a murine adenylyl cyclase (AC) polypeptide having a substitution of an alanine, or Ala (or "A") for an aspartic acid, or Asp (or "D") (i.e., a D=>A substitution) at position 426 in the catalytic core of the AC polypeptide. The SEQ ID NO:17 polypeptide differs from the SEQ ID NO:12 polypeptide in that the SEQ ID NO:17 polypeptide is missing the first ten amino acids of the SEQ ID NO:12 polypeptide; otherwise the polypeptides are identical. SEQ ID NO:16 is the murine amino acid sequence before the D=>A substitution. The isoform lacking the amino terminal is believed to be the wild type murine polypeptide, with the first ten amino acids of SEQ ID NO:11 and SEQ ID NO:12 being untranslated.

In alternative embodiments, the invention provides a (human) AC6mut polypeptide (SEQ ID NO:13) comprising a human adenylyl cyclase (AC) polypeptide having a substitution of an alanine, or Ala (or "A") for an aspartic acid, or Asp (or "D") at position 428 in the catalytic core of the AC polypeptide; i.e., in this embodiment, the murine adenylyl cyclase (AC) polypeptide has a substitution D=>A, or of an Ala for an Asp, at position 428 in the catalytic core of the murine AC polypeptide.

Human AC6 nucleic acid coding sequence (SEQ ID NO:14) vs murine coding sequence: 86% homology (SEQ ID NO:15). Human AC6 polypeptide (SEQ ID NO:10) vs murine AC6 polypeptide (SEQ ID NO:11) at amino acid levels: 94% homology.

The AC6mut D=>A substitution is in the exact same relative structural position in the catalytic core of the human AC6mut as the murine AC6mut, as illustrated below (showing the wild type still having the aspartic acid, or "D" residue, as underlined below:

```
Human     1    MSWFSGLLVPKVDERKTAWGERNGQKRSRRRGTRAGGFCTPRYMSCLRDAEPPSPIPAGP     60
Murine    11   MSWFSGLLVPKVDERKTAWGERNGQKRPRH-ANRASGFCAPRYMSCLKNAEPPSPIPAAH    69

Human     61   PRCPWQDDAFIRRGGPGKGKELGLRAVALGFEDTEVITTAGGTAEVAPDAVPRSGRSCWR   120
Murine    70   TRCPWQDEAFIRRAGPGRGVELGLRSVALGFDDIEVTIPMG-TAEVAPDTSPRSGPSCWH   128

Human     121  RLVQVFQSKQFRSAKLERLYQRYFFQMNQSSLTLLMAVLVLLTAVLLAFHAAPARPQPAY   180
Murine    129  RLVQVFQSKQFRSAKLERLYQRYFFQMNQSSLTLLMAVLVLLMAVLLTFHAAPAQPQPAY   188

Human     181  VALLACAAALFVGLMVVCNRHSFRQDSMWVVSYVVLGILAAVQVGGALAADPRSPSAGLW   240
Murine    189  VALLICASVLFVVLMVVCNRHSFRQDSMWVVSYVVLGILAAVQVGGALAANPHSPSAGLW   248

Human     241  CPVFFVYIAYILLPIRMRAAVLSGLGLSTLHLILAWQLNRGDAFLWRQLGANVLLFLCIN   300
Murine    249  CPVFFVYITYILLPIRMRAAVLSGLGLSTLHLILAWQLNSSDPFLWKQLGANVVLFLCIN   308

Human     301  VIGICTHYPAEVSQRQAFQETRGYIQARLHLQHENRQQERLLLSVLPQHVAMEMKEDINT   360
Murine    309  AIGVCTHYPAEVSQRQAFQETRGYIQARLHLQHENRQQERLLLSVLPQHVAMEMKEDINT   368

Human     361  KKEDMMFHKIYIQKHDNVSILFADIEGFTSLASQCTAQELVMTLNELFARFDKLAAENHC   420
Murine    369  KKEDMMFHKIYIQKHDNVSILFADIEGFTSLASQCTAQELVMTLNELFARFDKLAAENHC   428

Human     421  LRIKILGDCYYCVSGLPEARADHAHCCVEMGVDMIEAISLVREVTGVNVNMRVGIHSGRV   480
Murine    429  LRIKILGDCYYCVSGLPEARADHAHCCVEMGVDMIEAISLVREVTGVNVNMRVGIHSGRV   488

Human     481  HCGVLGLRKWQFDVWSNDVTLANHMEAGGRAGRIHITRATLQYLNGDYEVEPGRGGERNA   540
Murine    489  HCGVLGLRKWQFDVWSNDVTLANHMEAGGRAGRIHITRATLQYLNGDYEVEPGRGGERNA   548

Human     541  YLKEQHIETFLILGASQKRKEEKAMLAKLQRTRANSMEGLMPRWVPDRAFSRTKDSKAFR   600
Murine    549  YLKEQCIETFLILGASQKRKEEKAMLAKLQRTRANSMEGLMPRWVPDRAFSRTKDSKAFR   608

Human     601  QMGIDDSSKDNRGTQDALNPEDEVDEFLSRAIDARSIDQLRKDHVRRFLLTFQREDLEKK   660
Murine    609  QMGIDDSSKDNRGAQDALNPEDEVDEFLGRAIDARSIDQLRKDHVRRFLLTFQREDLEKK   668

Human     661  YSRKVDPRFGAYVACALLVFCFICFIQLLIFPHSTLMLGIYASIFLLLLITVLICAVYSC   720
Murine    669  YSRKVDPRFGAYVACALLVFCFICFIQLLVFPYSTLILGIYAAIFLLLLVTVLICAVCSC   728

Human     721  GSLFPKALQRLSRSIVRSRAHSTAVGIFSVLLVFTSAIANMFTCNHIPIRSCAARMLNLT   780
Murine    729  GSFFPKALQRLSRNIVRSRVHSTAVGIFSVLLVFISAIANMFTCNHIPIRTCAARMLNLT   788

Human     781  PADITACHLQQLNYSLGLDAPLCEGIMPTCSFPEYFIGNMLLSLLASSVFLHISSIGKLA   840
Murine    789  PADVTACHLQQLNYSLGLDAPLCEGTAPTCSFPEYFVGNVLLSLLASSVFLHISSIGKLA   848

Human     841  MIFVLGLIYLVLLLLGPPATIFDNYDLLLGVHGLASSNETFDGLDCPAAGRVALKYMTPV   900
Murine    849  MTFILGFTYLVLLLLGPPAAIFDNYDLLLGVHGLASSNETFDGLDCPAVGRVALKYMTPV   908

Human     901  ILLVFALALYLHAQQVESTARLDFLWKLQATGEKEEMEELQAYNRRLLHNILPKDVAAHF   960
Murine    909  ILLVFALALYLHAQQVESTARLDFLWKLQATGEKEEMEELQAYNRRLLHNILPKDVAAHF   968

Human     961  LARERRNDELYYQSCECVAVMFASIANFSEFYVELEANNEGVECLRLLNEIIADFDEIIS  1020
Murine    969  LARERRNDELYYQSCECVAVMFASIANFSEFYVELEANNEGVECLRLLNEIIADFDEIIS  1028

Human     1021 EERFRQLEKIKTIGSTYMAASGLNASTYDQVGRSHITALADYAMRLMEQMKHINEHSFNN  1080
Murine    1029 EERFRQLEKIKTIGSTYMAASGLNASTYDQVGRSHITALADYAMRLMEQMKHINEHSFNN  1088

Human     1081 FQMKIGLNMGPVVAGVIGARKPQYDIWGNIVNVSSRMDSTGVPDRIQVITDLYQVLAAKG  1140
```

```
Murine  1089  FQMKIGLNMGPVVAGVIGARKPQYDIWGNIVNVSSRMDSTGVPDRIQVITDLYQVLAAKG  1148

Human   1141  YQLECRGVVKVKGKGEMITYFLNGGPSS (SEQ ID NO: 10)                 1168

Murine  1149  YQLECRGVVKVKGKGEMTTYFLNGGPSS (SEQ ID NO: 11)                 1176

++++++++++++
```

In alternative embodiments, both the human ACmut nucleic acid coding sequence (SEQ ID NO:13) and the murine ACmut nucleic acid coding sequence (SEQ ID NO:12) were made by changing an adenosine (or "A") to a cytosine (or "C"), as indicated below, where the "A" residue before its change to "C" is underlined, below; i.e., illustrated below is the wild type human AC6 (SEQ ID NO:10) and wild type murine AC6 (SEQ ID NO:11):

```
Murine   90   CCTCCCAGCAGCATGTCATGGTTTAGTGGCCTCCTGGTTCCCAAAGTGGATGAACGGAAA  149
              |||  ||||| |||||||||||||||||||||||||||| |||||||||||||||||||
Human   649   CCTACCAGCAACATGTCATGGTTTAGTGGCCTCCTGGTCCCTAAAGTGGATGAACGGAAA  708

Murine  150   ACAGCTTGGGGGGAACGCAATGGGCAGAAGCG--C-CCACGCCACGCGAATCGAGCCAGT  206
              ||||| ||||| ||||||||||||||||||||  |  ||||   |  ||| || || ||
Human   709   ACAGCCTGGGGTGAACGCAATGGGCAGAAGCGTTCGCGGCGCCGTGGCACTCGGGCAGGT  768

Murine  207   GGCTTCTGCGCACCTCGCTACATGAGCTGCCTCAAGAATGCGGAGCCACCCAGCCCCACT  266
              ||||||||||  |||| ||||| ||||||||||| |   ||| |||||||||||||||
Human   769   GGCTTCTGCACGCCCCGCTATATGAGCTGCCTCCGGGATGCAGAGCCACCCAGCCCCACC  828

Murine  267   CCTGCAGCTCACACTCGGTGCCCCTGGCAGGATGAAGCCTTCATCAGGAGGGCGGGCCCG  326
              |||||  |  |   ||||||||||||||||||||  ||||||||| |||||| |||||
Human   829   CCTGCGGCCCCCCCTCGGTGCCCCTGGCAGGATGACGCCTTCATCCGGAGGGGCGGCCCA  888

Murine  327   GGCAGGGGTGTGGAGCTGGGGCTGCGGTCAGTGGCCTTGGGGTTTGACGACACTGAGGTG  386
              |||| |||     |||||||||||||| |||||||||| ||  || ||| || |||||
Human   889   GGCAAGGGCAAGGAGCTGGGGCTGCGGGCAGTGGCCCTGGGCTTCGAGGATACCGAGGTG  948

Murine  387   AC--C-ACACCGATGGGCACAGCTGAAGTGGCACCGGATACATCGCCTCGGAGCCGGTCCG  443
              ||  |  || ||   || || ||||| ||||| || ||    |  |  ||| ||||  |
Human   949   ACAACGACAGCGGGCGGGACGGCTGAGGTGGCGCCCGACGCGGTGCCCAGGAGTGGGCGA  1008

Murine  444   TCCTGCTGGCACCGGCTTGTGCAGGTGTTCCAGTCTAAGCAGTTCCGCTCTGCCAAGCTG  503
              |||||||||| || || ||||||||||||||||||  |||||||||| || ||||||||
Human  1009   TCCTGCTGGCGCCGTCTGGTGCAGGTGTTCCAGTCGAAGCAGTTCCGTTCGGCCAAGCTG  1068

Murine  504   GAGCGGCTGTACCAGCGGTACTTCTTCCAGATGAACCAGAGCAGCCTCACGCTGCTCATG  563
              ||||| |||||||||||||||||||||||||||||||||||||||||| |||||| |||
Human  1069   GAGCGCCTGTACCAGCGGTACTTCTTCCAGATGAACCAGAGCAGCCTGACGCTGCTGATG  1128

Murine  564   GCGGTGCTGGTGCTGCTCATGGCTGTACTGTTGACTTTCCACGCTGCGCCTGCCCAGCCT  623
              ||||||||||||||||| || ||| || |||  ||||||||||  || ||  ||  |||
Human  1129   GCGGTGCTGGTGCTGCTCACAGCGGTGCTGCTGGCTTTCCACGCCGCACCCGCCCGCCCT  1188

Murine  624   CAGCCTGCTTACGTGGCCCTGCTGACCTGTGCCTCTGTCCTTTTTGTGGTACTCATGGTG  683
              |||||||| ||  ||||| ||| || ||||||| ||  | ||  ||| ||| ||||||
Human  1189   CAGCCTGCCTATGTGGCACTGTTGGCCTGTGCCGCGCCCGTTCGTGGGGCTCATGGTG  1248

Murine  684   GTGTGTAACCGACACAGCTTCCGCCAGGACTCCATGTGGGTGGTGAGCTATGTGGTCCTG  743
              ||||||||||| || ||||||||||||||||||||||||||||||||||| ||||| ||
Human  1249   GTGTGTAACCGGCATAGCTTCCGCCAGGACTCCATGTGGGTGGTGAGCTACGTGGTGCTG  1308

Murine  744   GGCATCCTAGCAGCCGTGCAAGTCGGGGGTGCCCTGGCAGCCAATCCACACAGCCCCTCG  803
              ||||||||  |  |||||||  ||||| | |||||   ||||  |||| |||  |||| 
Human  1309   GGCATCCTGGCGGCAGTGCAGGTCGGGGGCGCTCTCGCAGCAGACCCGCGCAGCCCCTCT  1368

Murine  804   GCGGGCCTTTGGTGCCCCGTGTTCTTCGTCTACATCACCTACACTCTTCTTCCCATTCGC  863
              |||||||| |||||||| ||||||| |||||||| | |||||| |||||| ||||| ||
Human  1369   GCGGGCCTCTGGTGCCCTGTGTTCTTTGTCTACATCGCCTACACGCTCCTCCCCATCCGC  1428

Murine  864   ATGCGAGCCGCAGTACTCAGCGGCCTGGGCCTCTCTACTCTGCATTTGATTTTGGCCTGG  923
              ||||| || || || |||||||||||||||||| |   ||||||||||| ||||||||
Human  1429   ATGCGGGCTGCCGTCCTCAGCGGCCTGGGCCTCTCCACCTTGCATTTGATCTTGGCCTGG  1488

Murine  924   CAGCTCAACAGCAGCGACCCCTTCCTTTGGAAGCAGCTCGGTGCTAACGTGGTGCTCTTC  983
              || || |||  |   | |||||||||||||||||||||||||| || ||||||||| ||
Human  1489   CAACTTAACCGTGGTGATGCCTTCCTCTGGAAGCAGCTCGGTGCCAATGTGCTGCTGTTC  1548

Murine  984   CTCTGCACCAATGCCATCGGTGTCTGCACACACTACCCTGCTGAAGTGTCTCAGCGCCAA  1043
              ||||||||||| || || || ||||||||||||| |||||||| |||||||||||||| 
Human  1549   CTCTGCACCAACGTCATTGGCATCTGCACACACTATCCAGCAGAGGTGTCTCAGCGCCAG  1608

Murine 1044   GCTTTTCAGGAGACCCGAGGTTACATCCAGGCGCGGCTGCACCTGCAGCATGAGAACCGT  1103
```

```
                    ||  ||||||||||||  ||||||||||||||  |||||  ||||||||||||||||  ||
Human    1609  GCCTTTCAGGAGACCCGCGGTTACATCCAGGCCCGGCTCCACCTGCAGCATGAGAATCGG  1668

Murine   1104  CAGCAGGAACGGCTGCTGCTATCGGTGTTGCCCCAGCACGTTGCCATGGAGATGAAAGAA  1163
                ||||||||  |||||||||||||  |||||  ||||||||||||||||||||||||||
Human    1669  CAGCAGGAGCGGCTGCTGCTGTCGGTATTGCCCCAGCACGTTGCCATGGAGATGAAAGAA  1728

Murine   1164  GACATCAACAC        GAGGACATGATGTTCCATAAGATCTACATCCAGAAGCATGAT  1223
               |||||||||||        |||||||||||||||||||  ||||||||||||||||||||
Human    1729  GACATCAACACAAAAAAAGAAGACATGATGTTCCACAAGATCTACATACAGAAGCATGAC  1788

Murine   1224  AATGTCAGCATCCTGTTTGCGGACATTGAGGGCTTCACCAGCCTGGCCTCCCAGTGCACT  1283
               |||||||||||||||||||||  |||||||||||||||||||||||||  |||||||||
Human    1789  AATGTCAGCATCCTGTTTGCAGACATTGAGGGCTTCACCAGCCTGGCATCCCAGTGCACT  1848

Murine   1284  GCACAGGAACTGGTCATGACCTTGAATGAGCTCTTTGCCCGGTTTGACAAGCTGGCTGCG  1343
                |  |||||  ||||||||||||  |||||||||||||||||||||||||||||||||
Human    1849  GCGCAGGAGCTGGTCATGACCCTGAATGAGCTCTTTGCCCGGTTTGACAAGCTGGCTGCG  1908

Murine   1344  GAGAATCACTGTCTGAGGATCAAGATCTTAGGAGACTGTTACTACTGCGTGTCAGGGCTG  1403
               ||||||||||  |||||||||||||||||  || |||||||||||||| |||||||||
Human    1909  GAGAATCACTGCCTGAGGATCAAGATCTTGGGGGACTGTTACTACTGTGTGTCAGGGCTG  1968

Murine   1404  CCCGAGGCCCGGGCAGATCACGCCCACTGCTGTGTGGAGATGGGGGTAGACATGATCGAA  1463
               || |||||||||||| || || |||||||||||||||||||||||||||||||||  ||
Human    1969  CCGGAGGCCCGGGCCGACCATGCCCACTGCTGTGTGGAGATGGGGGTAGACATGATTGAG  2028

Murine   1464  GCCATCTCGCTGGTGCGTGAGGTAACAGGTGTGAACGTGAACATGCGTGTGGGCATCCAC  1523
               ||||||||||||||  |||||||||  ||||||||| |||||||||||||||||||||
Human    2029  GCCATCTCGCTGGTACGTGAGGTGACAGGTGTGAATCTGAACATGCGCGTGGGCATCCAC  2088

Murine   1524  AGCGGACGTGTGCATTGCGGCGTCCTTGGCCTACGGAAATGGCAGTTTGATGTCTGGTCA  1583
               |||||  ||||| ||||||||||||||||||| | |||||||||||||  |||||||
Human    2089  AGCGGGCGCGTGCACTGCGGCGTCCTTGGCTTGCGAAATGGCAGTTCGATGTGTGGTCC  2148

Murine   1584   AACGATGTGACCCTGGCTAACCACATGGAGGCCGG-GGGC-GGCCGG-CGCATCCACATC  1640
                || |||||||||||||||||||||||||||||| ||  ||  ||| || |||||||||
Human    2149  AATGATGTGACCCTGGCCAACCACATGGAGGCAGGAGGCCGGGCTGGCCGCATCCACATC  2208

Murine   1641  ACTCGGGCTACACTGCAGTACTTGAACGGGGACTATGAGGTGGAGCCAGGCCGTGGTGGT  1700
               ||||||||  ||||||||||||| ||||||||||| |||||||||||||||||||||
Human    2209  ACTCGGGCAACACTGCAGTACCTGAACGGGGACTACGAGGTGGAGCCAGGCCGTGGTGGC  2268

Murine   1701  GAACGCAATGCGTACCTCAAGGAGCAGTGCATTGAGACCTTCCTCATACTTGGCGCCAGC  1760
                || ||||||  |||||||||||||||| ||  |||||||| || ||  ||||||||||
Human    2269  GAGCGCAACGCGTACCTCAAGGAGCAGCACATTGAGACTTTCCTCATCCTGGGCGCCAGC  2328

Murine   1761  CAAAAACGGAAAGAGGAGAAAGCCATGCTGGCCAAGCTTCAGCGGACACGGGCCAACTCC  1820
               || ||||||||||||||||||| ||||||||||||||||  ||||||| |||||||||||
Human    2329  CAGAAACGGAAAGAGGAGAAGGCCATGCTGGCCAAGCTGCAGCGGACTCGGGCCAACTCC  2388

Murine   1821  ATGGAAGGACTGATGCCCCGCTGGGTTCCTGACCGTGCCTTCTCCCGGACCAAGGACTCT  1880
               |||||||  ||||||| |||||||||||||||  ||||||||||||||||||||||||
Human    2389  ATGAAGGGCTGATGCCGCGCTGGGTTCCTGATCGTGCCTTCTCCCGGACCAAGGACTCC  2448

Murine   1881  AAGGCATTCCGCCAGATGGGCATTGATGATTCTAGCAAAGACAACCGGGGTGCCCAAGAT  1940
               |||||  ||||||||||||||||||||||||| ||||||||||||||||| |||||||
Human    2449  AAGGCCTTCCGCCAGATGGGCATTGATGATTCCAGCAAAGACAACCGGGGGCACCCAAGAT  2508

Murine   1941  GCTCTGAACCCTGAAGATGAGGTGGATGAGTTCCTGGGCCGAGCCATCGATGCCCGAAGC  2000
                || |||||||||||| |||||||||||||||||||  |||| ||||||||||||  ||
Human    2509  GCCCTGAACCCTGAGGATGAGGTGGATGAGTTCCTGAGCCGTGCCATCGATGCCCGCAGC  2568

Murine   2001  ATCGACCAACTGCGTAAGGACCATGTGCGCCGGTTCCTGCTCACCTTCCAGAGAGAGGAT  2060
               ||  || || ||||| |||||||||||||| ||||||||||||||||||||||||||||
Human    2569  ATTGATCAGCTGCGGAAGGACCATGTGCGCCGGTTTCTGCTCACCTTCCAGAGAGAGGAT  2628

Murine   2061  CTTGAGAAGAAGTATTCACGGAAAGTAGATCCTCGCTTCGGAGCCTACGTCGCCTGTGCC  2120
               |||||||||||||| ||  ||||| || |||| ||||||||||||||||| ||||||||
Human    2629  CTTGAGAAGAAGTACTCCCGGAAGGTGGATCCCCGCTTCGGAGCCTACGTTGCCTGTGCC  2688

Murine   2121  CTCCTGGTTTTTTGCTTCATCTGTTTTATCCAGCTCCTTGTGTTCCCATACTCCACCCTG  2180
               ||  ||||  || || ||||||||  || ||||  ||  |  ||||||||||||||||
Human    2689  CTGTTGGTCTTCTGCTTCATCTGCTTCATCCAGCTTCTCATCTTCCCACACTCCACCCTG  2748

Murine   2181  ATACTCGGGATTTATGCC-GCTATCTTCCTGCTGTTGCTGGTCACTGTGCTGATCTGTGC  2239
               || || |||| |||||||  ||||||||||||||||  |||| |||||||||||||||||
Human    2749  ATGCTTGGGATCTATGCCAGC-ATCTTCCTGCTGCTGCTAATCACCGTGCTGATCTGTGC  2807
```

-continued

```
Murine 2240 CGTGTGCTCCTGCGGTTCTTTCTTCCCCAAGGCCCTGCAACGCCTGTCCCGCAATATTGT 2299
            |||| |||||| ||||||| | ||||| |||||||||||||| |||||||||| |||||
Human  2808 TGTGTACTCCTGTGGTTCTCTGTTCCCTAAGGCCCTGCAACGTCTGTCCCGCAGCATTGT 2867

Murine 2300 CCGCTCACGGGTGCACAGCACCGCGGTTGGAATCTTCTCGGTTCTGCTTGTGTTCATCTC 2359
            |||||||||| || ||||||||||| ||||| ||||| || ||||||||||||| | ||
Human  2868 CCGCTCACGGGCACATAGCACCGCAGTTGGCATCTTTTCCGTCCTGCTTGTGTTTACTTC 2927

Murine 2360 TGCCATCGCCAACATGTTTACCTGTAATCACACCCCAATAAGGACCTGCGCGGCCCGGAT 2419
            |||||| ||||||||||| |||||||| |||||||| ||| ||| || || ||||||||
Human  2928 TGCCATTGCCAACATGTTCACCTGTAACCACACCCCCATACGGAGCTGTGCAGCCCGGAT 2987

Murine 2420 GCTGAACTTAACACCAGCGGATGTCACCGCCTGCCACCTACAACAGCTCAATTACTCTCT 2479
            ||||||| |||||||| || ||| || |||||||||||| ||| ||||||||||||||| 
Human  2988 GCTGAATTTAACACCTGCTGACATCACTGCCTGCCACCTGCAGCAGCTCAATTACTCTCT 3047

Murine 2480 GGGACTGGATGCTCCCCTGTGTGAGGGCACCGCACCCACCTGCAGCTTCCCTGAGTACTT 2539
            ||| |||||||||||||||||||||||||||| ||||||||||||| |||||||||||| 
Human  3048 GGGCCTGGATGCTCCCCTGTGTGAGGGCACCATGCCCACCTGCAGCTTTCCTGAGTACTT 3107

Murine 2540 CGTCGGGAACGTGCTGCTGAGTCTTCTAGCCAGCTCTGTCTTCCTACACATCAGCAGCAT 2599
            | ||||||||||||||||||||||| |||||||||||||||||||| ||||||||||||
Human  3108 CATCGGGAACATGCTGCTGAGTCTCTTGGCCAGCTCTGTCTTCCTGCACATCAGCAGCAT 3167

Murine 2600 CGGCAAGCTGGCCATGACCTTCATCTTGGGGTTCACCTACTTGGTGCTGCTTTTGCTGGG 2659
            ||| ||| ||||||||| ||| ||||||||| || |||| |||||||||||| |||||| 
Human  3168 CGGGAAGTTGGCCATGATCTTTGTCTTGGGGCTCATCTATTTGGTGCTGCTTCTGCTGGG 3227

Murine 2660 TCCCCCGGCCGCCATCTTTGACAACTATGATCTACTGCTTGGCGTCCATGGCTTGGCTTC 2719
            |||||| || || |||||||||||||||||| |||||||||||||||||||||||||||
Human  3228 TCCCCCAGCCACCATCTTTGACAACTATGACCTACTGCTTGGCGTCCATGGCTTGGCTTC 3287

Murine 2720 CTCCAATGAGACCTTTGATGGGCTGGACTGCCCAGCTGTGGGGAGGGTAGCGCTCAAATA 2779
             |||||||||||||||||||||||||||| ||||||||| |||||||||  || |||||
Human  3288 TTCCAATGAGACCTTTGATGGGCTGGACTGTCCAGCTGCAGGGAGGGTGGCCCTCAAATA 3347

Murine 2780 TATGACCCCCGTGATTCTGCTGGTGTTTGCCCTGGCACTGTATCTGCATGCACAACAGGT 2839
            |||||| |||||||||||||||||||||||| ||||| |||||||||||| || ||||| 
Human  3348 TATGACCCCTGTGATTCTGCTGGTGTTTGCGCTGGCGCTGTATCTGCATGCTCAGCAGGT 3407

Murine 2840 GGAATCGACTGCCCGCCTGGACTTCCTGTGGAAGTTACAGGCAACAGGGGAGAAGGAGGA 2899
            ||| ||||||||| ||| ||||||||||| ||||||||||||||||||||||||||||| 
Human  3408 GGAGTCGACTGCCCGCCTAGACTTCCTCTGGAAACTACAGGCAACAGGGGAGAAGGAGGA 3467

Murine 2900 GATGGAGGAGCTACAGGCATACAACCGGAGGTTGCTGCATAACATTCTTCCCAAGGACGT 2959
            ||||||||||||||||||||||||||||||| ||||||||||||||||| |||||||||
Human  3468 GATGGAGGAGCTACAGGCATACAACCGGAGGCTGCTGCATAACATTCTGCCCAAGGACGT 3527

Murine 2960 GGCCGCCCACTTCCTGGCCCGGGAACGCCGCAACGATGAGCTGTACTACCAGTCGTGTGA 3019
            ||| ||||||||||||||||||||| |||| |||||||| |||| ||||||||||||||
Human  3528 GGCGGCCCACTTCCTGGCCCGGGAGCGCCGCAATGATGAACTCTACTATCAGTCGTGTGA 3587

Murine 3020 ATGTGTGGCTGTCATGTTTGCCTCCATCGCCAATTTCTCGGAGTTCTACGTGGAGCTCGA 3079
              ||||||||||| |||||||||||||| ||||| ||| ||||| |||||||||||| |
Human  3588 GTGTGTGGCTGTTATGTTTGCCTCCATTGCCAACTTCTCTGAGTTCTATGTGGAGCTGGA 3647

Murine 3080 GGCAAACAACGAGGGCGTGGAGTGCCTGCGGCTGCTCAATGAGATCATCGCAGACTTTGA 3139
            |||||||| || || ||| |||||||||||||||||| ||||||||||| ||||||||| 
Human  3648 GGCAAACAATGAGGGTGTCGAGTGCCTGCGGCTGCTCAACGAGATCATCGCTGACTTTGA 3707

Murine 3140 CGAGATCATCAGTGAGGAGAGATTCCGGCAGTTGGAGAAGATCAAGACCATCGGTAGCAC 3199
             ||||| ||||| ||||||||| ||||||||| ||||||||||||||||| || |||||
Human  3708 TGAGATTATCAGCGAGGAGCGGTTCCGGCAGCTGGAAAAGATCAAGACGATTGGTAGCAC 3767

Murine 3200 CTACATGGCCGCCTCTGGGCTAAATGCCAGCACCTATGACCAGGTCGGCCGCTCACACAT 3259
            ||||||||| ||||| ||||| |||||||||||||| |||||||| ||||||| ||||| 
Human  3768 CTACATGGCTGCCTCAGGGCTGAACGCCAGCACCTACGATCAGGTGGGCCGCTCCCACAT 3827

Murine 3260 CACGGCGCTGGCTGACTATGCCATGCGGCTCATGGAGCAGATGAAACACATCAATGAACA 3319
            ||| || ||||||||||| |||||||||||||||||||||||||| ||||||||||| |
Human  3828 CACTGCCCTGGCTGACTACGCCATGCGGCTCATGGAGCAGATGAAGCACATCAATGAGCA 3887

Murine 3320 CTCTTTCAACAATTTCCAGATGAAGATCGGGTTGAACATGGGTCCGGTTGTAGCAGGCGT 3379
            ||| |||||||||||||||||||||||| || |||||||||| |  || || ||||| ||
Human  3888 CTCCTTCAACAATTTCCAGATGAAGATTGGGCTGAACATGGGCCCAGTCGTGGCAGGTGT 3947

Murine 3380 CATTGGGGCCCGAAAGCCACAGTATGACATCTGGGGAAATACCGTGAATGTTTCCAGTCG 3439
            ||| ||||| ||||||||||||||||||||||||| ||| || |||||||| || |||| 
Human  3948 CATCGGGGCTCGGAAGCCACAGTATGACATCTGGGGGAACACAGTGAATGTCTCTAGTCG 4007
```

```
Murine 3440  TATGGACAGCACTGGAGTTCCTGACCGAATACAGGTGACTACGGACCTATACCAGGTTCT  3499
             ||||||||||| || || || |||||||| ||||||| |||||||| ||||||||||||
Human  4008  TATGGACAGCACGGGGGTCCCCGACCGAATCCAGGTGACCACGGACCTGTACCAGGTTCT  4067

Murine 3500  AGCTGCCAAGGGCTACCAGCTGGAGTGTCGAGGGGTGGTCAAGGTGAAGGGAAAGGGGGA  3559
             |||||||||||||||||||||||||||||||||||||||||||||||||| ||||||||
Human  4068  AGCTGCCAAGGGCTACCAGCTGGAGTGTCGAGGGGTGGTCAAGGTGAAGGGCAAGGGGGA  4127

Murine 3560  GATGACCACCTACTTCCTCAACGGGGGCCCCAGCAGT  3596 (from SEQ ID NO:10)
             |||||||||||||||||||||| ||||||||||||||
Human  4128  GATGACCACCTACTTCCTCAATGGGGGCCCCAGCAGT  4164 (from SEQ ID NO:11)
```

In alternative embodiments, nucleic acids of the invention are made, isolated and/or manipulated by, e.g., cloning and expression of cDNA libraries, amplification of message or genomic DNA by PCR, and the like. The nucleic acids and genes used to practice this invention, including DNA, RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides (e.g., cAMP-incompetent AC chimeric proteins used to practice this invention) generated from these nucleic acids can be individually isolated or cloned and tested for a desired activity. Any recombinant expression system can be used, including e.g. bacterial, fungal, mammalian, yeast, insect or plant cell expression systems or expression vehicles.

Alternatively, nucleic acids used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In alternative embodiments, to practice the methods of the invention, AC6mut fusion proteins and nucleic acids encoding them are used. Any AC6mut polypeptide can be used to practice this invention. In alternative embodiments, the AC6mut protein can be fused to a heterologous peptide or polypeptide, such as a peptide for targeting the polypeptide to a desired cell type, such as a cardiac myocyte.

In alternative embodiments, a heterologous peptide or polypeptide joined or fused to a protein used to practice this invention can be an N-terminal identification peptide which imparts a desired characteristic, such as fluorescent detection, increased stability and/or simplified purification. Peptides and polypeptides used to practice this invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Nucleic acids or nucleic acid sequences used to practice this invention, e.g., AC6mut-encoding nucleic acids, can be an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. Compounds use to practice this invention include "nucleic acids" or "nucleic acid sequences" including oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., e.g., double stranded iRNAs, e.g., iRNPs). Compounds use to practice this invention include nucleic acids, i.e., oligonucleotides, containing known analogues of natural nucleotides. Compounds use to practice this invention include nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. Compounds use to practice this invention include "oligonucleotides" including a single stranded polydeoxynucleotide or two complementary polydeoxynucleotide strands that may be chemically synthesized. Compounds use to practice this invention include synthetic oligonucleotides having no 5' phosphate, and thus will not ligate to another oligonucleotide without adding a phosphate with an ATP in the presence of a kinase. A synthetic oligonucleotide can ligate to a fragment that has not been dephosphorylated.

In alternative aspects, compounds used to practice this invention include genes or any segment of DNA involved in producing an AC6mut polypeptide; it can include regions preceding and following the coding region (leader and trailer) as well as, where applicable, intervening sequences (introns) between individual coding segments (exons). "Operably linked" can refer to a functional relationship between two or more nucleic acid (e.g., DNA) segments. In alternative aspects, it can refer to the functional relationship of transcriptional regulatory sequence to a transcribed sequence. For example, a promoter can be operably linked to a coding sequence, such as a nucleic acid used to practice this invention, if it stimulates or modulates the transcription of the coding sequence in an appropriate host cell or other expression system. In alternative aspects, promoter transcriptional regulatory sequences can be operably linked to a transcribed sequence where they can be physically contiguous to the transcribed sequence, i.e., they can be cis-acting. In alternative aspects, transcriptional regulatory sequences, such as enhancers, need not be physically contiguous or located in close proximity to the coding sequences whose transcription they enhance.

In alternative aspects, the invention comprises use of "expression cassettes" comprising a nucleotide sequences used to practice this invention, which can be capable of affecting expression of the nucleic acid, e.g., a structural gene or a transcript (e.g., encoding AC6mut protein) in a host compatible with such sequences. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes used to practice this invention also include plasmids, expression vectors, recombinant viruses, any form of recombinant "naked DNA" vector, and the like. In alternative aspects, a "vector" used to practice this invention can comprise a nucleic acid that can infect, transfect, transiently or permanently transduce a cell. In alternative aspects, a vector used to practice this invention can be a naked nucleic acid, or a nucleic acid complexed with protein or lipid. In alternative aspects, vectors used to practice this invention can comprise viral or bacterial nucleic acids and/or proteins, and/or membranes (e.g., a cell membrane, a viral lipid envelope, etc.). In alternative aspects, vectors used to practice this invention can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, the vector used to practice this invention can be stably replicated by the cells during mitosis as an autonomous structure, or can be incorporated within the host's genome.

In alternative aspects, "promoters" used to practice this invention include all sequences capable of driving transcription of a coding sequence in a cell, e.g., a mammalian cell such as a heart, lung, muscle, nerve or brain cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

In alternative embodiments, "constitutive" promoters used to practice this invention can be those that drive expression continuously under most environmental conditions and states of development or cell differentiation. In alternative embodiments, "Inducible" or "regulatable" promoters used to practice this invention can direct expression of the nucleic acid of the invention under the influence of environmental conditions, administered chemical agents, or developmental conditions.

Adenovirus Vector and Adeno-Associated Virus (AAV) Delivery

In alternative embodiments, delivery vehicles, vectors, expression vectors, recombinant viruses, or equivalent are or comprise: an adeno-associated virus (AAV); a recombinant AAV virus, vector or virion; or, an adenovirus vector. In alternative embodiments, the AAV, recombinant AAV virus or vector, or adenovirus vector, is or comprises: an AAV serotype AAV5, AAV6, AAV7, AAV8 or AAV9; a rhesus macaque AAV (AAVrh), or an AAVrh10; or any pseudotype, hybrid or derivative thereof.

In alternative embodiments, any of these vectors (or any delivery vehicle of the invention) is tropic for, or is designed for specific delivery to, a particular cell, tissue or organ. For example, in alternative embodiments, an AAV used to practice the invention (or any vector or delivery vehicle used to practice the invention) is tropic (or has tropism) for the heart. In other embodiments, an AAV used to practice the invention (or any vector or delivery vehicle) is tropic for, or is designed for specific delivery another tissue or organ, for example, the liver. In alternative embodiments, this "peripheral" mode of delivery, e.g., delivery vehicles, vectors, recombinant viruses and the like, are injected IM or IV, can circumvent problems encountered when genes or nucleic acids are expressed directly in an organ (e.g., the heart, lung or kidney) itself. For example, AAV5, AAV6, and AAV9 have been found to be tropic for the heart, see e.g., Fang et al., Hum Gene Ther Methods 2012 Oct. 17; Zincarelli, et al., Clin Transl Sci. 2010 June; 3(3):81-9.

Adeno-associated virus (AAV) used to practice the invention can be any non-pathogenic member of the Parvoviridae family of small, non-enveloped, single-stranded DNA animal viruses. AAV require helper virus (e.g., adenovirus) for replication and, thus, AAVs used to practice the invention do not replicate upon administration to a subject. AAV can infect a relatively wide range of cell types and stimulate only a mild immune response, particularly as compared to a number of other viruses, such as adenovirus. AAV serotypes used to practice this invention include, e.g., AAV1, AAV2, AAV3, AAV4, AAV5, AAV6, AAV7, AAV8, AAV9, AAV10, AAV11, and AAV12. AAV used to practice the invention can be from other animals, including: e.g., birds (e.g., avian AAV, or AAAV), bovines (e.g., bovine AAV, or BAAV), canines, equines, ovines, and porcines.

In alternative embodiments, AAV vectors used to practice the invention are recombinant nucleic acid molecules in which at least a portion of the AAV genome is replaced by a heterologous nucleic acid molecule; one can replace about 4.7 kilobases (kb) of AAV genome DNA, e.g., by removing the viral replication and capsid genes. In alternative embodiments, the heterologous nucleic acid molecule is simply flanked by AAV inverted terminal repeats (ITRs) on each terminus. The ITRs serve as origins of replication and contain cis acting elements required for rescue, integration, excision from cloning vectors, and packaging. In alternative embodiments AAVs used to practice the invention comprise a promoter operatively linked to the heterologous nucleic acid molecule to control expression.

An AAV vector can be packaged into an AAV capsid in vitro with the assistance of a helper virus or helper functions expressed in cells to yield an AAV virion. The serotype and cell tropism of an AAV virion are conferred by the nature of the viral capsid proteins. AAV vectors and AAV virions can transduce cells efficiently, including both dividing and non-dividing cells. AAV vectors and virions have been shown to be safe and to lead to long term in vivo persistence and expression in a variety of cell types.

In alternative embodiments, an ITR joined to 5' terminus of the AC6mut-encoding nucleic acid molecule, and an ITR joined to the 3' terminus of the AC6mut-encoding nucleic acid molecule. Examples of ITRs include, but are not limited to, AAV1, AAV2, AAV3, AAV4, AAV5, AAV6, AAV7, AAV8, AAV9, AAV10, AAV11, AAV12, AAAV, BAAV, and other AAV ITRs known to those skilled in the art. In one embodiment, an AAV ITR is selected from an AAV2 ITR, an AAV5 ITR, an AAV6 ITR, and a BAAV ITR. In one embodiment, an AAV ITR is an AAV2 ITR. In one embodiment, an AAV ITR is an AAV5 ITR. In one embodiment, an AAV ITR is an AAV6 ITR. In one embodiment, an AAV ITR is a BAAV ITR.

In alternative embodiments, AAV vectors (and other vectors, recombinant viruses and the like) used to practice the invention comprise other sequences, such as expression control sequences, e.g., a promoter, an enhancer, a repressor, a ribosome binding site, an RNA splice site, a polyadenylation site, a transcriptional terminator sequence, and a microRNA binding site. Examples of promoters include, but are not limited to, an AAV promoter, such as a p5, p19 or p40 promoter, an adenovirus promoter, such as an adenoviral major later promoter, a cytomegalovirus (CMV) promoter, a papilloma virus promoter, a polyoma virus promoter, a respiratory syncytial virus (RSV) promoter, a sarcoma virus promoter, an SV40 promoter, other viral promoters, an actin promoter, an amylase promoter, an immunoglobulin promoter, a kallikrein promoter, a metallothionein promoter, a heat shock promoter, an endogenous promoter, a promoter regulated by rapamycin or other small molecules, other cellular promoters, and other promoters known to those skilled in the art. In one embodiment, the promoter is an AAV promoter. In one embodiment, the promoter is a CMV promoter. Selection of expression control sequences to include can be accomplished by one skilled in the art.

In alternative embodiments, AAV vectors of different serotypes (as determined by the serotype of the ITRs within such vector) are used, e.g., an AAV1 vector, an AAV2 vector, an AAV3 vector, an AAV4 vector, an AAV5 vector, an AAV6 vector, an AAV7 vector, an AAV8 vector, an AAV9 vector, an AAV10 vector, an AAV11 vector, an AAV 12 vector, an AAAV vector, and a BAAV vector. In alternative embodiments the AAV vector is an AAV2 vector, an AAV5 vector, an AAV6 vector or a BAAV vector.

In alternative embodiments, chimeric, shuffled or capsid-modified AAV derivatives are used to provide one or more desired functionalities for the viral vector. alternative embodiments, these derivatives may display increased efficiency of gene delivery, decreased immunogenicity (humoral or cellular), an altered tropism range and/or improved targeting of a particular cell type compared to an AAV viral vector comprising a naturally occurring AAV genome. In alternative embodiments increased efficiency of gene delivery is achieved by improved receptor or co-receptor binding at the cell surface, improved internalization, improved trafficking within the cell and into the nucleus, improved uncoating of the viral particle and/or improved conversion of a single-stranded genome to double-stranded form. In alternative embodiments an altered tropism range or targeting of a specific cell population results in increased efficiency, such that the vector dose is not diluted by administration to tissues where it is not needed.

In alternative embodiments, capsid-free AAV vectors are used as described e.g., in U.S. patent app. No. 20140107186. In alternative embodiments, AAV9 vectors that are heart- or liver-tropic are used as described e.g., in U.S. patent app. No. 20140056854. In alternative embodiments, AAV vectors are described in e.g., in U.S. patent app. Nos. 20130310443; 20130136729, are used to practice the invention.

In alternative embodiments, AAV vectors are pseudo-typed for e.g., improved or altered performance, e.g., to improve or alter the tropism or other features of the virus, as described e.g., in U.S. patent app. No 20120220492. For example, specific or improved targeting allows the delivery vehicle (e.g., the AAV viral particle) to infect and deliver the therapeutic nucleic acid (e.g., an AC6mut) only to those cells intended to be infected, thus decreasing the risk of unwanted side effects from gene therapy and increasing the efficacy of the gene therapy.

In alternative embodiments, dosages of the viral vector are determined by factors such as the condition being treated, the age, weight and health of the patient, and may thus vary among patients. For example, a therapeutically effective human dosage of a viral vector is generally in the range of from about 0.1 ml to about 100 ml of solution containing concentrations of from about $1 \times 10^9$ to $1 \times 10^{16}$ genomes virus vector. An exemplary human dosage for delivery to large organs (e.g., liver, muscle, heart and lung) may be about $5 \times 10^{10}$, to $5 \times 10^{13}$ AAV genomes per 1 kg, at a volume of about 1 to 100 mL. The dosages are adjusted to balance the therapeutic benefit against any side effects and such dosages may vary depending upon the therapeutic application for which the recombinant vector is employed.

The levels of expression of the transgene can be monitored to determine the frequency of dosage resulting in viral vectors, e.g., AAV vectors.

Formulations

In alternative embodiments, the invention provides compositions and methods for delivering and expressing AC6mut in vivo in a cardiac myocyte cell. In alternative embodiments, these compositions comprise AC6mut-encoding nucleic acids formulated for these purposes, e.g., expression vehicles or AC6mut-encoding nucleic acids formulated in a buffer, in a saline solution, in a powder, an emulsion, in a vesicle, in a liposome, in a nanoparticle, in a nanolipoparticle and the like.

In alternative embodiments, the compositions can be formulated in any way and can be applied in a variety of concentrations and forms depending on the desired in vivo or ex vivo conditions, including a desired in vivo or ex vivo method of administration and the like. Details on techniques for in vivo or ex vivo formulations and administrations are well described in the scientific and patent literature.

Formulations and/or carriers of the AC6mut-encoding nucleic acids used to practice this invention are well known in the art. Formulations and/or carriers used to practice this invention can be in forms such as tablets, pills, powders, capsules, liquids, gels, syrups, slurries, suspensions, etc., suitable for in vivo or ex vivo applications.

In alternative embodiments, AC6mut-encoding nucleic acids used to practice this invention can be in admixture with an aqueous and/or buffer solution or as an aqueous and/or buffered suspension, e.g., including a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate. Formulations can be adjusted for osmolarity, e.g., by use of an appropriate buffer.

In practicing this invention, the compounds (e.g., formulations) of the invention can comprise a solution of AC6mut-encoding nucleic acids or genes dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent (e.g., AC6mut-encoding nucleic acids or genes) in these formulations can vary widely, and can be selected primarily based on fluid volumes, viscosities and the like, in accordance with the particular mode of in vivo or ex vivo administration selected and the desired results, e.g., increasing in vivo AC6mut expression.

The solutions and formulations used to practice the invention can be lyophilized; for example, the invention provides a stable lyophilized formulation comprising AC6mut-encoding nucleic acids or genes. In one aspect, this formulation is made by lyophilizing a solution comprising AC6mut-encoding nucleic acid or gene and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations of the invention can be delivered by the use of liposomes (see also discussion, below). By using liposomes, particularly where the liposome surface carries ligands specific for target cells, e.g., cardiac myocytes, or are otherwise preferentially directed to a specific tissue or organ type, e.g., a heart, one can focus the delivery of the active agent into a target cell, e.g., a cardiac myocyte, in an in vivo or ex vivo application.

Nanoparticles, Nanolipoparticles and Liposomes

The invention also provides nanoparticles, nanolipoparticles, vesicles and liposomal membranes comprising compounds (e.g., AC6mut or AC6mut-encoding nucleic acids or genes) used to practice the methods of this invention, e.g., to deliver AC6mut or AC6mut-encoding nucleic acids or genes to cardiac myocyte cells in vivo or ex vivo. In alternative embodiments, these compositions are designed to target specific molecules, including biologic molecules, such as polypeptides, including cell surface polypeptides, e.g., for targeting a desired cell type, e.g., a mammalian cardiac cell, a cardiac myocyte and the like.

The invention provides multilayered liposomes comprising compounds used to practice this invention, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, e.g., to entrap a cAMP-incompetent AC-encoding nucleic acid or gene.

Liposomes can be made using any method, e.g., as described in Park, et al., U.S. Pat. Pub. No. 20070042031, including method of producing a liposome by encapsulating an active agent (e.g., AC6mut-encoding nucleic acids or genes), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice this invention comprise a substituted ammonium and/or polyanions, e.g., for targeting delivery of a compound (e.g., AC6mut-encoding nucleic acids or genes) used to practice this invention to a desired cell type, as described e.g., in U.S. Pat. Pub. No. 20070110798.

The invention also provides nanoparticles comprising compounds (e.g., AC6mut-encoding nucleic acids or genes) used to practice this invention in the form of active agent-containing nanoparticles (e.g., a secondary nanoparticle), as described, e.g., in U.S. Pat. Pub. No. 20070077286. In one embodiment, the invention provides nanoparticles comprising a fat-soluble active agent of this invention or a fat-solubilized water-soluble active agent to act with a bivalent or trivalent metal salt.

In one embodiment, solid lipid suspensions can be used to formulate and to deliver AC6mut-encoding nucleic acids or genes used to practice the invention to a mammalian cell in vivo or ex vivo, as described, e.g., in U.S. Pat. Pub. No. 20050136121.

Delivery Vehicles

In alternative embodiments, any delivery vehicle can be used to practice the methods or compositions of this invention, e.g., to deliver AC6mut or AC6mut-encoding nucleic acids or genes to practice the methods of the invention in vivo or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition of the invention, wherein a surfactant is associated with a nucleic acid via a non-covalent bond e.g. as described, e.g., in U.S. Pat. Pub. No. 20040151766.

In one embodiment, a nucleic acid used to practice this invention can be applied to cells as polymeric hydrogels or water-soluble copolymers, e.g., as described in U.S. Pat. No. 7,413,739; for example, a nucleic acid can be polymerized through a reaction between a strong nucleophile and a conjugated unsaturated bond or a conjugated unsaturated group, by nucleophilic addition, wherein each precursor component comprises at least two strong nucleophiles or at least two conjugated unsaturated bonds or conjugated unsaturated groups.

In one embodiment, a nucleic acid is applied to cells using vehicles with cell membrane-permeant peptide conjugates, e.g., as described in U.S. Pat. Nos. 7,306,783; 6,589,503. In one aspect, the nucleic acid itself is conjugated to a cell membrane-permeant peptide. In one embodiment, a nucleic acid and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver AC6mut-encoding nucleic acids or genes to a cell, e.g., using any electroporation system as described e.g. in U.S. Pat. Nos. 7,109,034; 6,261,815; 5,874,268.

Implanting Cells In Vivo

In alternative embodiments, the methods of the invention also comprise implanting or engrafting cells, e.g., cardiac or cardiac myocyte cells, comprising or expressing AC6mut-encoding nucleic acids or genes used to practice the invention; and in one aspect, methods of the invention comprise implanting or engrafting the AC6mut-encoding nucleic acids or genes (or cells expressing them) in a vessel, tissue or organ ex vivo or in vivo, e.g., a heart or a cardiac myocyte, or implanting or engrafting the re-programmed differentiated cell in an individual in need thereof.

Cells can be removed from an individual, treated using the compositions and/or methods of this invention, and reinserted (e.g., injected or engrafted) into a tissue, organ or into the individual, using any known technique or protocol. For example, de-differentiated re-programmed cells, stem cells, or re-programmed differentiated cells, can be re-implanted (e.g., injected or engrafted) using e.g., microspheres e.g., as described in U.S. Pat. No. 7,442,389; e.g., in one aspect, the cell carrier comprises a bulking agent comprising round and smooth polymethylmethacrylate microparticles preloaded within a mixing and delivery system and an autologous carrier comprising these cells. In another embodiment, the cells are re-administered to a tissue, an organ, e.g., a heart, and/or to an individual in need thereof in a biocompatible crosslinked matrix, as described e.g., in U.S. Pat. App. Pub. No. 20050027070.

In another embodiment, the cells of the invention (e.g., cells made by practicing the methods of this invention) are re-administered (e.g., injected or engrafted) to a tissue, an organ and/or an individual in need thereof within, or protected by, a biocompatible, nonimmunogenic coating, e.g., as on the surface of a synthetic implant, e.g., as described in U.S. Pat. No. 6,969,400, describing e.g., a protocol where AC6mut can be conjugated to a polyethylene glycol that has been modified to contain multiple nucleophilic groups, such as primary amino or thiol group.

In one embodiment, the cells of the invention (e.g., cells made by practicing the methods of this invention) are re-administered (e.g., injected or engrafted) to a tissue, an organ and/or an individual in need thereof using grafting methods as described e.g. by U.S. Pat. Nos. 7,442,390; 5,733,542.

Any method for delivering polypeptides, nucleic acids and/or cells to a tissue or organ (e.g., a cardiac myocyte, heart) can be used, and these protocols are well known in the art, e.g., as described in U.S. Pat. No. 7,514,401, describing e.g., using intracoronary (IC), intravenous (IV), and/or local delivery (direct myocardial injection) of polypeptides, nucleic acids and/or cells to a heart in situ. For example, in alternative embodiments, aerosol drug particles into the lungs and into the bloodstream, gene therapy, continuous infusions, repeated injections and/or sustained release polymers can be used for delivering polypeptides, nucleic acids and/or cells to a tissue or organ (e.g., a lung, kidney, heart). In alternative embodiments, nucleic acids and/or cells can be given through a catheter into the coronary arteries or by direct injection into the left atrium or ventricular myocardium via a limited thoracotomy; or delivered into the myocardium via a catheter passed during cardiac catheterization; or delivered into the pericardial space.

In alternative embodiments, nucleic acids used to practice this invention, or a vector comprising a nucleic acid used to practice the invention (e.g., an adenovirus-associated virus or vector (AAV), or an adenoviral gene therapy vector), or a vesicle, liposome, nanoparticle or nanolipid particle (NLP) of the invention, and the like, to a tissue or organ (e.g., a lung, kidney, heart); e.g. as described in U.S. Pat. No. 7,501,486.

Compositions used to practice this invention can be used in combination with other therapeutic agents, e.g. angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

Compositions used to practice this invention can be used for ameliorating or treating any of a variety of cardiopathies and cardiovascular diseases, e.g., cardiopathies and cardiovascular diseases, e.g., coronary artery disease (CAD); atherosclerosis; thrombosis; restenosis; vasculitis including autoimmune and viral vasculitis such as polyarteritis nodosa, Churg-Strass syndrome, Takayasu's arteritis, Kawasaki Disease and Rickettsial vasculitis; atherosclerotic aneurisms; myocardial hypertrophy; congenital heart diseases (CHD); ischemic heart disease and anginas; acquired valvular/endocardial diseases; primary myocardial diseases including myocarditis; arrhythmias; and transplant rejections; metabolic myocardial diseases and myocardiomyopathies such as congestive, hypertrophic and restrictive cardiomyopathies, and/or heart transplants.

Kits and Instructions

The invention provides kits comprising compositions and methods of the invention, including instructions for use thereof. As such, cells, delivery vehicles, vectors, expression vectors, recombinant viruses and the like, of the invention, can also be provided.

For example, in alternative embodiments, the invention provides kits comprising compositions comprising (a) AC6mut-encoding nucleic acid, (b) delivery vehicles, vectors, expression vectors, recombinant viruses and the like, of the invention, (c) a liquid or aqueous formulation of the invention, or (d) the vesicle, liposome, nanoparticle or nanolipid particle of the invention. In one aspect, the kit further comprising instructions for practicing any methods of the invention, e.g., in vitro or ex vivo methods for delivering a desired AC6mut or AC6mut-expressing nucleic acid, vector, and the like, to a cardiac myocyte cell.

The invention will be further described with reference to the following examples; however, it is to be understood that the invention is not limited to such examples.

EXAMPLES

Example 1

Delivery of cAMP-Incompetent AC Increases Cardiac Function

This example demonstrates the effectiveness of an exemplary embodiment of the invention: delivery of cAMP-incompetent AC to cardiac myocytes for the treatment of heart failure. In this study, we asked whether an AC mutant molecule that reduces LV cAMP production would have favorable effects on left ventricle (LV) function through its effects on $Ca^{2+}$ handling alone.

So many clinical trials of positive inotropes have failed, that it is now axiomatic that agents that increase cAMP are deleterious to the failing heart. An alternative strategy is to alter myocardial $Ca^{2+}$ handling or myofilament response to $Ca^{2+}$ using agents that do not affect cAMP. Although left ventricular (LV) function is tightly linked to adenylyl cyclase (AC) activity, the beneficial effects of AC may be independent of cAMP and instead stem from effects on $Ca^{2+}$ handling.

In this study, we generated transgenic mice with cardiac-directed expression of a cyclic adenosine monophosphate-incompetent (cAMP-incompetent) adenylyl cyclase type 6 (AC6) polypeptide, the so-called "AC6 mutant", or "AC6mut". Cardiac myocytes of these AC6mut transgenic mice showed impaired cAMP production in response to isoproterenol (74% reduction; p<0.001), but LV size and function were normal. Isolated hearts showed preserved LV function in response to isoproterenol stimulation. AC6mut expression was associated with increased sarcoplasmic reticulum $Ca^{2+}$ uptake and the EC50 for SERCA2a activation was reduced. Cardiac myocytes isolated from AC6mut mice showed increased amplitude of $Ca^{2+}$ transients in response to isoproterenol (p=0.0001). AC6mut expression also was associated with increased expression of LV S100A1 (p=0.03) and reduced expression of phospholamban protein (p=0.01). This study determined that LV AC mutant expression is associated with normal cardiac function despite impaired cAMP generation. The mechanism appears to be through effects on $Ca^{2+}$ handling—effects that occur despite diminished cAMP.

Data from previous studies indicated that increased cardiac AC type 6 (AC6), a dominant AC isoform expressed in mammalian cardiac myocytes [6], has protean beneficial effects on the failing left ventricle (LV) [7],[8],[9],[10],[11],[12]. These unexpected beneficial effects must be reconciled with the dire consequences on the heart of beta (B) adrenergic receptor (BAR) stimulation and elevations in intracellular cAMP [13],[14],[15],[16],[17],[18]. Indeed, the apparent benefits of AC6 expression in the failing heart is paradoxical. Using pharmacological inhibitors, data from previous studies suggest that some of the beneficial effects of increased cardiac AC6 expression do not depend upon increased cAMP generation [2],[3]. Because of the inherent limitations of studies using pharmacological inhibition in cultured cardiac myocytes, we generated a catalytically inactive murine AC6 mutant (AC6mut) molecule by substitution of Ala for Asp at position 426 in the catalytic core (position 426: position number based on SEQ ID NO:16), a change predicted to alter $Mg^{2+}$ binding but not influence G-protein dynamics [4]. This murine AC6mut molecule, when studied in vitro, markedly impairs cAMP generation, but retains the cellular distribution pattern associated with AC6 [4]. Such in vitro studies fall far short of establishing how such a molecule might influence cardiac function in vivo.

We therefore generated transgenic murine lines with cardiac-directed expression of AC6mut. Our hope was that such lines would provide additional insight vis-à-vis differentiation of cAMP vs $Ca^{2+}$ handling effects on the function of the intact normal heart. Furthermore, such studies might indicate whether AC6mut provides inotropic stimulation free from the potentially deleterious effects of increased cAMP. Our hypothesis was that LV function, despite marked diminution in cAMP generating capacity, would remain normal, through beneficial counterbalancing effects conferred by AC6 on $Ca^{2+}$ handling.

Methods

Generation of AC6mut Transgenic Mice (FIG. 1A).

The use of animals was in accordance with Association for Assessment and Accreditation of Laboratory Animal Care guidelines and was approved by the Institutional Animal Care and Use Committee of VA San Diego Healthcare System. To generate mice with cardiac-directed expression of AC6mut, the murine AC6mut cDNA [4] with an AU1 tag at the C-terminus, was subcloned between the α-myosin heavy chain promoter and SV40 polyA. A 9.2-kb fragment containing the expression cassette was used for pronuclear injection, carried out in the transgenic mouse facility at University of California, San Diego (inbred C57BL/6). Founder mice were identified by polymerase chain reaction (PCR) of genomic DNA prepared from tail tips.

The AC6mut gene was detected using a primer homologous to the α-MHC promoter (forward: 5' CACATAGAAGCCTAGCCCACACC) (SEQ ID NO:1); the reverse primer was for the AC6 region (5' CAGGAGGCCACTAAACCATGAC) (SEQ ID NO:2).

AC6mut mRNA was detected using the following primers: (forward: 5' TGGGCCTCTCTACTCTGCAT (SEQ ID NO:3); reverse: 5' TGGATGTAACCTCGGGTCTC) (SEQ ID NO:4) enabling quantification of fold increase of AC6mut mRNA over endogenous AC6 mRNA.

Endogenous AC6 mRNA was detected using primers homologous to its 3'-untranslated region (forward: 5' GGCATTGAGTGGGACTTTGT (SEQ ID NO:5); reverse: 5' TCTGCATCCAAACAAACGAA) (SEQ ID NO:6). This 3' untranslated region was not present in the AC6mut cDNA, enabling quantification of endogenous AC6.

Founder animals were crossbred with wild-type mice of the same strain, and selected animals were used for analysis of cardiac transgene expression. We documented variable transgene expression in independent lines and selected a line with a 17-fold increase in AC6mut protein expression (vs endogenous AC6) for our studies. LV expression levels of AC types 2-9 were determined using quantitative RT-PCR as previously described [5].

Echocardiography.

Anesthesia was induced with 5% isoflurane (at a flow rate of 1 L/min oxygen) and maintained with 1% isoflurane in oxygen. Images were obtained using a 16 L MHz linear probe and Sonos 5500® Echocardiograph system (Philips Medical Systems, Bothell, Wash.), as previously reported [7]. Data were acquired and analyzed without knowledge of group identity.

Isolated Perfused Hearts: LV Contractile Function.

Cardiac function was assessed in isolated perfused hearts to assess LV contractile function in a manner unaffected by reflex activation or anesthesia, as previously reported [7]. An intraventricular balloon catheter was deployed to measure isovolumic LV pressure (LV end-diastolic pressure 10 mmHg; 1.7 mM ionized $Ca^{2+}$). Isoproterenol was delivered in bolus doses (from 0.1 nM to 300 nM) at five-minute intervals as LV pressure was recorded. Subsequently, the first derivative of the LV pressure (LV dP/dt) was derived and used as a surrogate of LV contractile function. Data were acquired and analyzed without knowledge of group identity.

Calcium Uptake.

Initial rate of ATP-dependent sarcoplasmic reticulum (SR) $Ca^{2+}$ uptake in LV homogenates was measured by the modified Millipore filtration technique as described previously [11].

Calcium Transient.

Cytosolic calcium transients were measured using Indo-1, as described previously [19]. Cardiac myocytes were plated onto laminin-coated glass cover slips and loaded with indo-1/AM (3 µM, Calbiochem, La Jolla Calif.) and dispersing agent, pluronic F-127 (0.02 mg/ml, Calbiochem, La Jolla Calif.) for 30 min. Following dye loading, cover slips were mounted in a superfusion chamber, rinsed to remove excess indo-1/AM, and mounted on a Nikon DIAPHOT™ epifluorescence microscope equipped with a 40× objective interfaced to a Photon Technologies photometry system (Birmingham N.J.) with the excitation wavelength set to 365 nm via a monochromator. Fluorescence emission was split and directed to two photomultiplier tubes through 20-nm bandpass filters centered at 405 and 485 nm, respectively. The ratio F405/F485 represents a measure for $[Ca^{2+}]i$. During these measurements, cardiac myocytes were superfused with 25 mM HEPES (pH 7.3) containing 2 mM $CaCl_2$. Myocytes were field-stimulated at 0.3 Hz. Isoproterenol-stimulated $Ca^{2+}$ transient was determined by adding isoproterenol (10 µM) to the buffer. Calcium transients were recorded from at least 20 cells per heart and for at least 3 hearts per group. Diastolic and systolic intracellular $Ca^{2+}$ levels were obtained from the basal and maximal F405/F485 ratio per cycle, respectively.

Cardiac Myocyte Isolation.

Cardiac myocyte isolation was performed as previously described [4].

Cyclic AMP Measurement.

Isolated cardiac myocytes were stimulated with isoproterenol (10 µM, 10 min) or the water-soluble forskolin analog NKH477 (10 µM, 10 min), and then lysed (2.5% dodecyltrimethylammonium bromide, 0.05 M sodium acetate, pH 5.8, and 0.02% bovine serum albumin) Cyclic AMP was measured using the cAMP BIOTRAK™ enzyme immunoassay system (GE Healthcare, Pittsburgh, Pa.) as previously reported [4].

PKA Activity Assay.

Isolated cardiac myocytes were stimulated with isoproterenol (10 µM, 10 min) or NKH477 (10 µM, 10 min) Cardiac myocytes were homogenized in buffer A: 20 mM Tris-HCl (pH 7.4), 0.5 mM EGTA, 0.5 mM EDTA, and protease inhibitor cocktail from Invitrogen) and centrifuged (14,000×g, 5 min, 4° C.). The supernatant was incubated with PKA biotinylated peptide substrate (SignaTECT® (SIGNATECT®) cAMP-Dependent Protein Kinase Assay System (Promega, Madison Wis.)) in the presence of [$\gamma$-$^{32}$P] ATP. The $^{32}$P-labeled, biotinylated substrate was recovered with a streptavidin matrix, and the specific activity of PKA determined.

Isoproterenol-Stimulated Phosphorylation of Ryanodine Receptor-2, PLB, and Troponin I in Cardiac Myocytes.

To determine dynamic phosphorylation of key $Ca^{2+}$ regulating proteins, we conducted studies of basal and isoproterenol-stimulated phosphorylation of RyR2, PLB and TnI in cultured cardiac myocytes isolated from each group (FIG. 2C). Cultured cardiac myocytes (100,000 cells per well) were used in these studies and immunoblotting performed before and after incubation with isoproterenol (10 µM, 10 min) Cells were lysed in lysis buffer: 20 mM Tris-HCl (pH 7.5), 150 mM NaCl, 1 mM Na2EDTA, 1 mM EGTA, 1% Triton, 2.5 mM sodium pyrophosphate, 1 mM β-glycerophosphate, 1 mM Na3VO4, 1 µg/ml leupeptin). Protein concentration was measured using the Bradford method Immunoblots were normalized to GAPDH and compared (FIG. 2D).

PDE Activity Assay.

Phosphodiesterase activity was assayed using the Cyclic Nucleotide Phosphodiesterase Assay Kit (Enzo). LV tissues were homogenized in buffer containing 10 mM Tris-HCl (pH 7.4), 1 mM PMSF, 10 mM activated orthovanadate, 1x protease inhibitor cocktail (Life Sciences) and centrifuged at 10,000 rpm (10 min) in a microfuge. Tissue homogenates were desalted by gel filtration using Desalting Column Resin (Enzo). Twenty µg of protein (Bradford) was added to each well and PDE activity measured.

Immunofluorescence.

Isolated cardiac myocytes were attached to laminin coated 2-well chamber slides for 1 hr, washed, fixed (10% formalin, 15 min, 23° C.), blocked with normal goat serum (1 hr) and incubated (4° C., overnight) with: anti-AU1 antibody (Fitzgerald, 1:300; for detecting AC6mut transgene protein); anti-Cav3 antibody (BD Pharmagen, 1:100; for detecting caveolae); anti-PDI antibody (Invitrogen, 1:1000; for detecting SR); anti-lamin A (Abcam, 1:200; for detecting nuclear envelope); anti-CREM-1 antibody (Santa Cruz, 1:50); or anti-phospho-CREB antibody (Upstate, 1:100). Cardiac myocytes were washed with PBS and then incubated with secondary antibodies (Alexia Fluo 488 or 594 conjugated, 1:1000 dilution) for 1 hr. To identify the nucleus, cells were incubated with Hoechst dye (1:1000 dilution, 20 min) Cardiac myocytes then were imaged as previously described [2].

Detection of mRNA and Immunoblotting.

Quantitative reverse transcription polymerase chain reaction (RT-qPCR) was used to quantify mRNA and immunoblotting was used to quantify protein content [4]. The primers for RyR2 included (forward: 5'AACC-TACCAGGCTGTGGATG) (SEQ ID NO:7); and (reverse: 5' GACTCGATGGGCAAGTCAAT) (SEQ ID NO:8).

We used the anti-AC5/6 antibody to identify endogenous AC6 and AC6mut (Santa Cruz, 1:200 dilution). The epitope for the AC5/6 antibody is at the C-terminus of AC6 and AC6mut (sequence: KGYQLECRGVVKVKGKGEMT-TYFLNGGPSS (SEQ ID NO:9); protein accession #O43306 and #Q01234). We used AU1 antibody (Fitzgerald, 1:2,000) to detect AC6mut protein. Additional antibodies used included: calreticulin (ABR Affinity, 1:1,000); calsequestrin (Novus Biologicals, 1:1,000); GAPDH (Fitzgerald, 1:20,000); PDE3A (Advam); PKA catalytic subunit (BD Transduction, 1:1,000); p-PKA catalytic subunit (Cell Signaling, 1:1,000); PKA-RIIα and PKA-RIIβ (BD Transduction, 1:1,000); phospho-PKA-RIIα (S96) and phospho-PKA-RIIβ (S114) (Santa Cruz, 1:200); PKCα catalytic subunit (Santa Cruz, 1:200); PLB (Affinity Bioreagents, 1:5,000); phospho 516-PLB (Badrilla, 1:3,000 dilution); phospho-RyR2 (S2808) (Abcam, 1:1,000); S100A1 (Epiyomics, 1:1,000); SERCA2a (Enzo, 1:1,000); troponin I and phospho-TnI (S22/23) (Cell Signaling, 1:1,000 each)

Statistical Analysis.

Data represent mean±SE; group differences were tested for statistical significance using either ANOVA, followed by Bonferroni t-testing, or, when appropriate, Student's t test (unpaired, 2-tailed). The null hypothesis was rejected when p<0.05.

Results

AC6mut Transgenic Mice.

AC6mut mice were physically indistinguishable from their transgene negative siblings. Necropsy of adult mice showed that body weight, tibial length, LV weight, and lung weight showed no group differences. (Table 1).

LV Expression of AC6mut.

AC6mut mRNA was increased 62-fold and protein was increased 17-fold over the levels of endogenous AC6, which were detected using primers and antibody to the common regions on both endogenous AC6 and transgene AC6mut in RT-PCR and immunoblotting (FIGS. 1B and 1C).

LV Expression of Endogenous AC Types.

The mRNA of endogenous AC types 2-9 showed no group differences (data not shown).

LV cAMP Production.

LV samples from AC6mut mice showed reduced cAMP production when stimulated with isoproterenol (74% reduction; p<0.001) or NKH477, a water-soluble forskolin analog (52% reduction; p=0.05) (FIG. 1D); basal cAMP production was unchanged. Thus, the transgenic line was suited to test the overall effect of reduced βAR-stimulated cAMP production in the presence of increased AC6mut expression on LV function.

PKA Activity and Expression.

Cardiac myocytes isolated from AC6mut mice showed a 48% reduction in basal PKA activity (p=0.01). In addition there were reductions in PKA activity stimulated by isoproterenol (38% reduction; p=0.006); and NKH477 (38% reduction; p=0.001) (FIG. 2A, upper). AC6mut expression did not alter LV expression of the PKA catalytic subunit (FIG. 2A, lower) or expression or phosphorylation of PKA-RII-α and β (phospho-PKA-RIIa: AC6mut, 0.32±0.04 du; Con, 0.30±0.03 du, p=0.7; phospho-PKA-RIIβ: AC6mut, 7.1±1.1 du; Con, 10.6±01.4 du; p=0.09; FIG. 2B). PKC catalytic subunit expression also showed no group difference (PKCa: AC6mut, 0.8±0.1 du; Con, 0.7±0.1 du, p=0.4; FIG. 2B)

Isoproterenol-Stimulated Phosphorylation of Ryanodine Receptor-2, PLB and Troponin I in Cardiac Myocytes.

Basal phosphorylation of RyR2, PLB and TnI showed no group differences (P-RyR2: AC6mut, 4.4±0.6 vs Con, 2.4±0.5 du, p=0.06; P-PLB: AC6mut, 0.3±0.03 vs Con, 0.2±0.1 du, p=0.8; P-TnI: AC6mut, 0.8±0.2 vs Con, 1.0±0.01 du, p=0.24, FIG. 2C). Isoproterenol stimulation was associated with increased phosphorylation of RyR2, PLB, and TnI in both groups (vs un-stimulated), but the extent of phosphorylation generally was greater in LV from AC6mut mice (P-RyR2: AC6mut, 30.0±1.1 vs Con, 7.4±1.1 du, p=0.001, P-PLB: AC6mut, 16.8±2.4 vs Con, 5.3±0.1 du, p=0.01; P-TnI: AC6mut, 5.8±1.4 vs Con, 2.2±0.7 du, p=0.07; FIG. 2C). TnI protein expression was not different between groups (AC6mut, 0.9±0.1 vs Con, 0.7±0.2 du; p=0.5; FIG. 2B. RyR2 mRNA expression showed no group difference.

PDE Activity and PDE3A Expression.

There was no group difference in PDE activity in LV samples (AC6mut: 1252±23 Units/mg, n=7; Control: 1293±39 Units/mg, n=6; p=0.38). LV PDE3A protein expression showed no group difference (AC6mut: 0.3±0.1 vs Con, 0.4±0.1 du, p=0.6. FIG. 2B).

Intracellular Distribution of AC6mut.

AC6mut protein was identified in association with caveolae (mainly associated with plasma membrane), SR, and nuclear envelope (FIG. 1E).

Echocardiography.

Echocardiography showed that basal cardiac structure and function were unchanged by cardiac-directed expression of AC6mut. LV dimensions were not different between groups, and basal LV ejection fraction and the velocity of circumferential fiber shortening were similar (Table 2). Thus, despite marked diminution of LV cAMP generating capacity in AC6mut mice, LV structure and basal function were unaltered.

LV Contractile Function in Response to Isoproterenol.

To assess cardiac contractility in a manner independent of autonomic nervous influence, endogenous catecholamines, and anesthesia, LV pressure development was measured in isolated perfused hearts. Basal and isoproterenol-stimulated LV dP/dt showed no group differences (FIG. 3), despite marked diminution in LV cAMP generating capacity.

$Ca^{2+}$ Uptake and $Ca^{2+}$ Related Proteins.

ATP-dependent SR $Ca^{2+}$ uptake rate in pooled LV homogenates from AC6mut and transgene-negative sibling control mice was determined Increased AC6mut expression was associated with increased SR $Ca^{2+}$ uptake (FIG. 4A, upper panel). In addition, an increased affinity of SERCA2a for $Ca^{2+}$ was reflected in a reduced $Ca^{2+}$ concentration required for a half maximal effect (EC50: AC6mut 1.1 µmol/L; Control 3.7 µmol/L, n=6, FIG. 4A, lower panel).

Associated with these physiological changes in $Ca^{2+}$ handling was altered LV expression of proteins that regulate SR $Ca^{2+}$ uptake. For example, AC6mut expression was associated with a 43% reduction in LV PLB protein expression (p=0.01), and a 73% increase in LV S100A1 protein content (p=0.03) (FIGS. 4B and 4C). The contents of LV SERCA2a, calreticulin, and calsequestrin were unchanged, and PLB phosphorylation at Ser16 was unchanged (FIG. 4D).

Transcription Factors.

AC6mut expression was associated with a 2-fold increase in LV expression of CREM-1 (p=0.03, FIG. 4B) and a 1.7-fold increase in phosphorylation of CREB at Ser133 (p=0.01, FIG. 4C); total CREB protein content was unaltered. To determine whether increased CREM-1 and phospho-CREB were present in the nuclei, immunofluorescence staining of isolated cardiac myocytes was performed using anti-CREM-1 and anti-phospho-CREB (S133) antibodies. We detected increased nuclear localization of CREM-1 and phospho-CREB in AC6mut mice (FIG. 4E).

Calcium Transients:

To determine whether increased SR $Ca^{2+}$ uptake associated with AC6mut expression would affect cytosolic $[Ca^{2+}]i$, cardiac myocyte real-time $[Ca^{2+}]i$ was assessed using the ratiometric dye Indo-1. Basal $Ca^{2+}$ release during contraction was unchanged (FIG. 5A). However, AC6mut expression was associated with increased peak systolic $Ca^{2+}$ transient amplitude after isoproterenol stimulation (p=0.0001, FIGS. 5B and 5C), and time to peak amplitude was decreased (p=0.03, FIG. 5D). In addition, time to 50% relaxation (tau) was decreased (p=0.04) in cardiac myocytes from AC6mut mice (FIG. 5E). Thus, SERCA2a activity, expression of PLB and S100A1, and isoproterenol-stimulated $Ca^{2+}$ transients all were altered by AC6mut expression in a manner that would favorably influence LV function.

DISCUSSION

The most surprising and important finding of this study is that cardiac-directed expression of a mutant AC6 molecule that markedly impairs βAR-stimulated cAMP production is associated with preserved LV function in response to isoproterenol stimulation. This was confirmed by echocardiography and studies of contractile function in isolated perfused hearts. Marked diminution of cardiac cAMP generation in other settings is associated with proportional reductions in LV contractile function. For example, most models of heart failure, where cAMP impairment typically is 50% reduced, there is a similar reduction in LV dP/dt and in βAR-responsiveness [10],[11],[12],[13],[14]. Furthermore, deletion of AC6, which is associated with a 60% reduction in cAMP generating capacity, was also associated with a similar reduction in LV contractile function [5]. What then explains preservation of isoproterenol-stimulated LV contractile function?

The proximate mechanisms for preserved LV function despite markedly impaired cAMP generation in the AC6mut line were favorable changes on $Ca^{2+}$ handling. We previously reported that cardiac-directed expression of AC6 increased function of the failing heart, but because of pronounced effects of AC6 on βAR signaling, it was impossible to determine the degree to which these beneficial effects reflected augmented βAR signaling per se vs $Ca^{2+}$ handling [10],[11]. Supporting the link of AC6 to $Ca^{2+}$ handling is the observation that AC6 deletion has striking adverse effects on $Ca^{2+}$ handling [5], but since cAMP-generating capacity was reduced following AC6 deletion, the independent effects of AC6 on $Ca^{2+}$ handling were difficult to ascertain. What is new in the present study, however, is the demonstration in TG mice that an AC6 mutant molecule appears to mimic the parent molecule's favorable effects on $Ca^{2+}$ handling, thereby preserving LV function even whilst cAMP generating capacity is markedly diminished. It appears that the effects of AC6 on $Ca^{2+}$ handling does not require cAMP generation, and must therefore occur through alternative mechanisms.

We found that AC6mut expression is associated with increased SR $Ca^{2+}$ uptake in LV homogenates and increased $Ca^{2+}$ transients with reduced time of relaxation in intact cardiac myocytes. Associated with these physiologically favorable effects of AC6mut expression was reduced PLB expression, a $Ca^{2+}$ regulator that inhibits SERCA2a activity. Reduced PLB content or increased PLB phosphorylation at Ser16 is associated with reduction of its inhibitory effects, which increases SERCA2a activity [20],[21],[22]. We previously found that PLB expression is reduced in cultured cardiac myocytes expressing AC6 or AC6mut [4], but the current study is the first to demonstrate that this effect is also seen in vivo (FIG. 4B). Increases in the degree of isoproterenol-stimulated phosphorylation of RyR2, PLB, and to a lesser extent, TnI (FIG. 2C) in cardiac myocytes isolated from AC6mut mice would be predicted also to increase LV contractile function.

AC6mut expression was associated with increased expression and nuclear translocation of CREM-1 (FIGS. 3B and 3E), a transcriptional suppressor in the CREB/ATF family [23]. We previously identified that, in the setting of AC6 expression, the PLB promoter was negatively regulated by increased ATF3 in neonatal rat cardiac myocytes through the CRE site in the PLB promoter [2]. In the present study we did not see increased ATF3 expression associated with AC6mut expression. However, both ATF3 and CREM-1 recognize the same CRE sites, so it is plausible that the AC6mut-related increased CREM-1 may be mechanistically important in reduced PLB expression. This will require additional study.

AC6mut expression was associated with an unanticipated increase in LV expression of the $Ca^{2+}$ sensitizing protein, S100A1, which increases contractile function through modulation of RyR2 and SERCA2a [24]. How might AC6mut expression be linked with increased LV S100A1 expression? AC6mut expression was associated with increased phosphorylation and nuclear translocation of CREB (FIGS. 4C and 4E), processes that are required for CREB activation. CREB is a transcriptional activator that regulates many genes through CRE site(s) in their promoters [25]. The S100A1 promoter possesses a CRE site [26], indicating that S100A1 expression could plausibly have been activated by AC6mut expression. In addition, compartmentalization of PKA and cAMP may also be factors [27],[28].

The substantial improvements in $Ca^{2+}$ handling appear to have preserved LV function despite marked diminution in cAMP generation. The precise pathways by which increased amounts of AC6mut influence transcriptional regulation and ultimately the physiological behavior of cardiac myocytes and LV function will require additional studies. Histological studies (FIG. 1E) confirm that substantial amounts of transgene AC6mut are present in multiple intracellular compartments, not just in the plasma membrane. This enables AC6mut protein to interact with important intracellular proteins that influence intracellular signaling and thereby affect physiological function.

The importance of AC6 vis-à-vis $Ca^{2+}$ handling was recently underscored by AC6 deletion [5]. In this setting, cAMP generating capacity was reduced, albeit not by as much as in the present study, but $Ca^{2+}$ handling was markedly impaired. In the present study, we see more marked impairment of cAMP generation, but $Ca^{2+}$ handling is increased, not decreased. This is because, unlike in AC6 deletion, the AC6 molecule, albeit one deficient in cAMP generating capacity, is present in the cytoplasm where it may influence $Ca^{2+}$ handling.

We did not examine transgenic lines that expressed reduced amounts of AC6mut to determine if the physiological effects were proportional to level of AC6mut expression.

One could argue that a 17-fold increase in AC6mut protein (vs endogenous AC6) might affect signaling in a non-specific manner. While our data cannot discount this possibility, it is important to recognize that endogenous AC6 is an exceedingly low abundance protein—approximately 100-fold less abundant, for example, than Gsα [29]. Therefore, even expressed at 17-fold higher level than endogenous AC6, it still is considerably less abundant than Gsα. Furthermore, similar increases in the catalytically active (normal) AC6 are associated with marked increases in recruitable cAMP production [30]. These observations suggest that the findings are specific.

CONCLUSIONS

Substantial improvements in $Ca^{2+}$ handling appear to preserve LV function despite marked diminution in cAMP generation Immunofluorescence indicates that AC6mut is located on the nuclear envelope, providing an opportunity for AC6mut to influence transcription factor expression and function. Increased CREM-1, a transcriptional suppressor and increased phospho-CREB (FIG. 4E) may be involved in altered expression of PLB and S100A1 respectively. We conclude that AC6mut preserves cardiac function through increased $Ca^{2+}$ handling and altered protein expression, despite reduced cAMP generation. These results provide insight regarding the interplay between $Ca^{2+}$ handling and PAR signaling vis-à-vis LV function, and indicate that AC6mut may provide inotropic stimulation free from the potentially deleterious effects of increased cAMP. Data indicated reduced cardiac myocyte apoptosis associated with AC6mut expression in the failing heart, which is a focus of an ongoing study in our laboratory.

FIGURE LEGENDS

Figure 1:
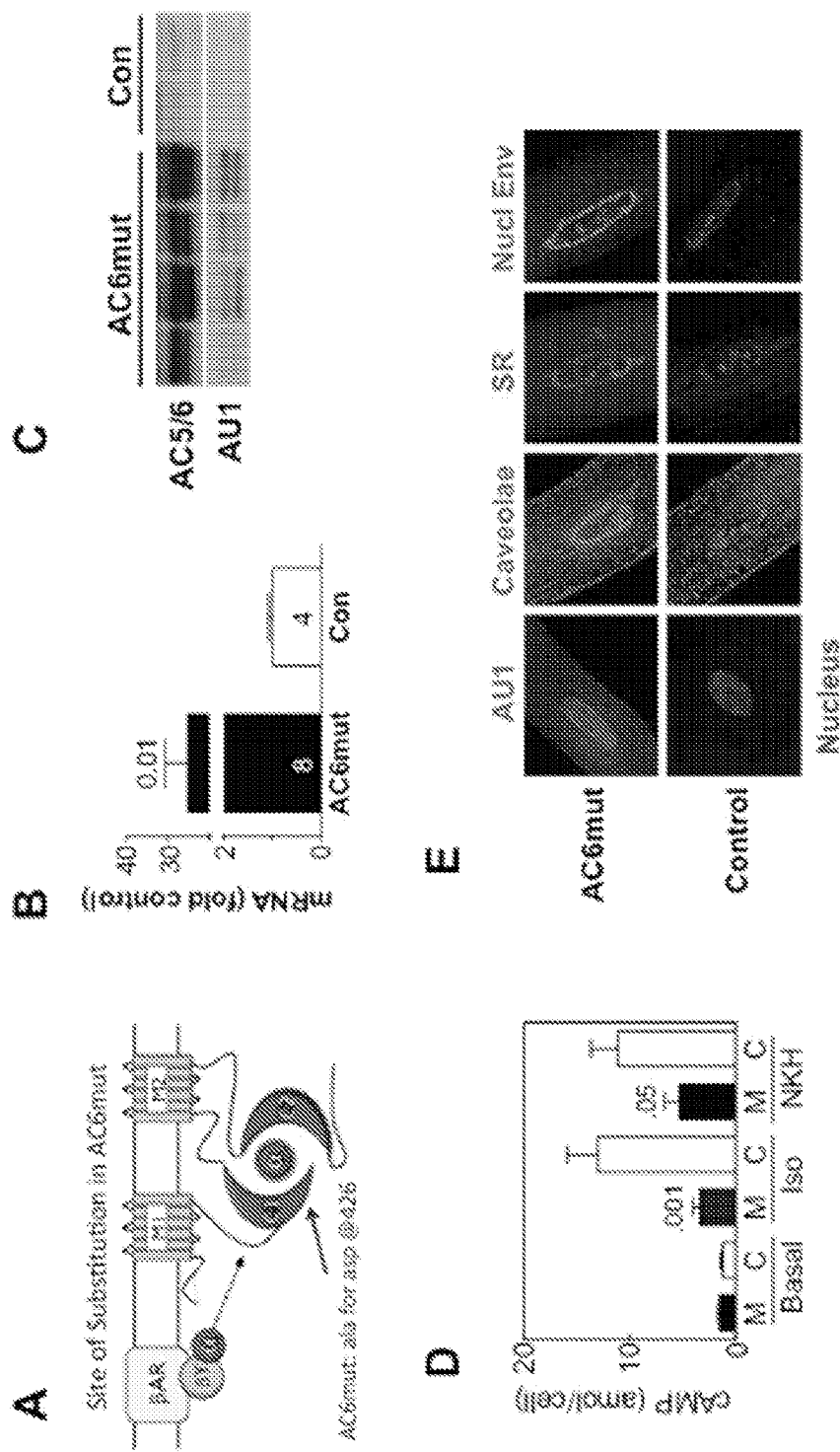
FIG. 1 illustrates the design, expression, activity and cellular distribution of the exemplary AC6mut of the invention.

FIG. 1. AC6mut Design, Expression, Activity and Cellular Distribution
A. The diagram depicts the site of substitution of alanine (ala) for aspartic acid (asp) at position 426 (position number based on SEQ ID NO:16) in the C1 domain (intracellular loop) in the construction of AC6mut. The substitution inhibits $Mg^{2+}$ binding and alters the efficiency of Gsα-mediated activation of the catalytic core, which impairs the enzymatic activity of AC6, resulting in reduced cAMP production. M1 and M2, transmembrane domains of AC6; C1 and C2, cytoplasmic domains of AC6, which form the catalytic core; βAR, β-adrenergic receptor; βY and α, components of the guanosine 5'-triphosphate (GTP)-binding protein, Gs
B. AC6mut mRNA expression was assessed by qRT-PCR using primers common to endogenous AC6 and transgene AC6mut. Primers for detecting GAPDH mRNA were used for internal control of the qRT-PCR reaction. AC6mut mRNA was increased 62-fold vs endogenous AC6. Animal number in bars+SE; Student's t-test, unpaired, 2 tails
C. AC6mut protein was detected in immunoblotting using anti-AC5/6 antibody and confirmed using anti-AU1 tag antibody. AC6mut protein was increased 17-fold vs endogenous AC6.
D. Cyclic AMP production in isolated cardiac myocytes from AC6mut and control mice, before (Basal) and after stimulation with isoproterenol (Iso; 10 µM, 10 min) or NKH477 (NKH; 10 µM, 10 min); cAMP Enzymeimmunoassay. Cardiac myocytes from AC6mut mice (M vs C, control) showed impaired cAMP production in response to Iso and NKH477, a forskolin analog. Bars denote mean+SE; p values from 1-way ANOVA followed by Bonferroni post test (n=6, each group).
E. Double immunofluorescence staining of AC6mut protein in cardiac myocytes isolated from AC6mut vs control mice using anti-AU1 antibody (red); anti-caveolin 3 (Cav-3) antibody (green, for caveolae); anti-protein disulphide-isomerase (PDI) antibody (green, for sarcoplasmic reticulum); anti-lamin A antibody (green, for nuclear envelope), and anti-voltage dependent anion selective channel protein (VDAC) antibody (green, for mitochondria). Nucleus is blue. AC6mut transgene was detected in caveolae, SR, and nuclear envelope, but was not associated with mitochondria.

FIG. 2. Activities and Expression of PKA, PKS and PDE
A. Upper Graph: PKA activity in isolated cardiac myocytes without stimulation (Basal) or stimulated with isoproterenol (Iso; 10 µM, 10 min) or NKH477 (NKH; 10 µM, 10 min). AC6mut expression reduced basal PKA activity (p=0.01) and both Iso (p=0.001) and NKH (p=0.001) activities were reduced as well (n=3, each group). Lower Gel: PKA protein in LV homogenates. LV PKA catalytic subunit protein expression was unaltered by AC6mut expression.
B. The expression of key signaling proteins and their phosphorylation are shown in immunoblots using left ventricular homogenates from AC6mut and control mice. No group differences were observed. Shown are phospho (P) and Total (T) PKA regulatory subunits II-α and II-β, PKCα, Phosphodiesterase type 3A (PDE3A), phospho-troponin I (P22/23-TnI), and total TnI.
C. Phosphorylation of RyR2, PLB and TnI before and after isoproterenol stimulation was assessed in cultured cardiac myocytes isolated from each group. Basal phosphorylation of RyR2, PLB and TnI showed no group differences. Isoproterenol stimulation was associated with increased phosphorylation of RyR2, PLB, and TnI in both groups, but was more extensive in cardiac myocytes from AC6mut mice (FIG. 2C).
D. The data from FIG. 2C indicating that isoproterenol stimulation was associated with increased phosphorylation of RyR2, PLB, and TnI in cardiac myocytes from AC6mut mice are shown in graphic format, normalized for loading (GAPDH). The increase in TnI phosphorylation was not statistically significant (p=0.07).

FIG. 3. Left Ventricular Contractile Function
Isolated hearts from AC6mut TG mice (closed circle; n=11) showed preserved LV dP/dt in response to isoproterenol stimulation through a wide range of isoproterenol doses. Data were acquired and analyzed without knowledge of group identity. Open circles, transgene negative control mice (n=12). There was no group difference (2-way ANOVA). Data points denote mean±SE.

FIG. 4. SR $Ca^{2+}$ uptake, $Ca^{2+}$ signaling proteins, and transcriptional factors
A. Upper: $Ca^{2+}$ uptake activity in pooled LV samples from AC6mut and TG negative sibling control mice (n=6, both groups)
Lower: Expression of AC6mut decreased SERCA2a affinity for $Ca^{2+}$. The effective concentration of $Ca^{2+}$ for 50% maximal effect ($EC_{50}$) was calculated from the initial ATP-dependent $Ca^{2+}$ uptake rate at different free $Ca^{2+}$ concentrations.
B. Upper: AC6mut expression was associated with decreased LV phospholamban (PLB) expression.
Lower: AC6mut expression was associated with increased LV CREM-1 protein expression.

C. Upper: AC6mut expression was associated with increased LV S100A1 protein expression.

Lower: AC6mut expression was associated with increased LV P133-CREB protein expression. Total CREB expression was similar in both groups.

D. AC6mut expression did not affect LV expression of SERCA2a, calreticulin, calsequestrin or phospho-S16-PLB proteins. (n=4, both groups).

E. Double immunofluorescence staining of AC6mut protein in isolated cardiac myocytes from AC6mut and control mice using anti-AU1 antibody (red) and anti-CREM-1 antibody (green) or anti-AU1 and anti-phospho-CREB (S133, green). Nucleus was showing in blue. AC6mut expression increased nuclear localizations of CREM-1 and phospho-CREB.

In graphs (A,B,C), bars denote mean+SE; numbers in bars indicate group size; members above bars indicate p values from Student's t-test (unpaired, 2 tailed)

FIG. 5. Cytosolic $Ca^{2+}$ Transients in Isolated Cardiac Myocytes from AC6mut and Control Mice A. Basal $Ca^{2+}$ released (systolic-diastolic $Ca^{2+}$) showed no group difference.

B. Representative Indo-1 $Ca^{2+}$ transient recordings in cardiac myocytes stimulated with isoproterenol (Iso; 10 μM) were higher in cardiac myocytes from AC6mut mice. Summary data are displayed in Panel C.

C. $Ca^{2+}$ released in the presence of isoproterenol was increased in cardiac myocytes from AC6mut mice.

D. Time-to-peak $Ca^{2+}$ transient in the presence of isoproterenol was decreased in cardiac myocytes from AC6mut mice.

E. Time to 50% relaxation (tau) in the presence of isoproterenol was decreased in cardiac myocytes from AC6mut mice.

Experiments were repeated four times. Bars denote mean+SE; numbers in bars indicate number of cardiac myocytes; numbers above bars indicate p values from Student's t-test (unpaired, 2-tailed).

REFERENCES

1. Cleland J G, Teerlink J R, Senior R, Nifontov E M, McMurray J J, et al. (2011) The effects of the cardiac myosin activator, omecamtiv mecarbil, on cardiac function in systolic heart failure: a double-blind, placebo-controlled, crossover, dose-ranging phase 2 trial. Lancet 378: 676-683.
2. Gao, M H, Tang T, Guo T, Sun S Q, Feramisco J R, et al. (2004) Adenylyl cyclase type VI gene transfer reduces phospholamban expression in cardiac myocytes via activating transcription factor 3. J Biol Chem 279: 38797-3802.
3. Gao M H, Tang T, Guo T, Yajima T, Pestonjamasp K, et al. (2008) Adenylyl cyclase type VI increases Akt activity and phospholamban phosphorylation in cardiac myocytes. J Biol Chem 283: 33527-33535.
4. Gao M H, Tang T, Lai N C, Yajima T, Miyanohara A, et al. (2011) Beneficial effects of adenylyl cyclase type 6 (AC6) expression persist using a catalytically inactive AC6 mutant. Mol Pharmacol 79: 381-388.
5. Tang T, Gao M H, Lai N C, Firth A L, Takahashi T, et al. (2008) Adenylyl cyclase type 6 deletion decreases left ventricular function via impaired calcium handling. Circulation. 117: 61-69.
6. Ping P, Anzai T, Gao M H, Hammond H K. (1996) Adenylyl cyclase and G protein receptor kinase expression during development of heart failure. Am J Physiol Heart Circ Physiol 273: H707-717.
7. Roth D M, Bayat H, Drumm J D, Gao M H, Swaney J S, Ander A, et al. (2002) Adenylyl cyclase increases survival in cardiomyopathy. Circulation 105: 1989-1994.
8. Takahashi T, Tang T, Lai N C, Roth D M, Rebolledo B, Saito M, et al. (2006) Increased cardiac adenylyl cyclase expression is associated with increased survival after myocardial infarction. Circulation 114: 388-396.
9. Lai N C, Roth D M, Gao M H, Tang T, Dalton N, et al. (2004) Intracoronary adenovirus encoding adenylyl cyclase VI increases left ventricular function in heart failure. Circulation 110: 330-336.
10. Roth D M, Gao M H, Lai N C, Drumm J, Dalton N, et al. (1999) Cardiac-directed adenylyl cyclase expression improves heart function in murine cardiomyopathy. Circulation 99: 3099-3102.
11. Lai N C, Tang T, Gao M H, Saito M, Takahashi T, et al. (2008) Activation of cardiac adenylyl cyclase expression increases function of the failing ischemic heart in mice. J Am Coll Cardiol 51: 1490-1497.
12. Tang T, Gao M H, Roth D M, Guo T, Hammond H K. (2004) Adenylyl cyclase type VI corrects cardiac sarcoplasmic reticulum calcium uptake defects in cardiomyopathy. Am J Physiol 287: H1906-1912.
13. Gaudin C, Ishikawa Y, Wight D C, Mandavi V, Nadal-Ginard B, et al. (1995) Overexpression of Gsα protein in the hearts of transgenic mice. J Clin Invest 95: 1676-1683.
14. Engelhardt S, Hein L, Wiesmann F, Lohse M J. (1999) Progressive hypertrophy and heart failure in β1-adrenergic receptor transgenic mice. Proc Natl Acad Sci 96: 7059-7064.
15. Liggett S B, Tepe N M, Lorenz J N, Canning A M, Jantz T D, et al. (2000) Early and delayed consequences of β2-adrenergic receptor overexpression in mouse hearts: critical role for expression level. Circulation 101: 1707-1714.
16. Antos C L, Frey N, Marx S O, Reiken S, Gaburjakova M, et al. (2001) Dilated cardiomyopathy and sudden death resulting from constitutive activation of protein kinase A. Circ Res 89: 997-1004.
17. Packer M, Carver J R, Rodeheffer R J, Ivanhoe R J, Dibianco R, et al. (1991) Effect of oral milrinone on mortality in severe chronic heart failure. The PROMISE Study Research Group. N Engl J Med 325: 1468-1475.
18. Bristow M R, Ginsburg R, Minobe W, Cubicciotti R S, Sageman W S, et al. (1982) Decreased catecholamine sensitivity and beta-adrenergic-receptor density in failing human hearts. N Engl J Med 307: 205-211.
19. Suarez J, Scott B, Dillmann W H. (2008) Conditional increase in SERCA2a protein is able to reverse contractile dysfunction and abnormal calcium flux in established diabetic cardiomyopathy. Am J Physiol 295: R1439-1445.
20. Brittsan A G, Kranias E G. (2000) Phospholamban and cardiac contractile function. J Mol Cell Cardiol 32: 2131-2139.
21. Chu G, Lester J W, Young K B, Luo W, Zhai J, et al. (2000) A single site (Ser16) phosphorylation in phospholamban is sufficient in mediating its maximal cardiac responses to beta-agonists. J Biol Chem 275: 38938-38943.
22. Luo W, Chu G, Sato Y, Zhou Z, Kadambi V J, et al. (1998) Transgenic approaches to define the functional role of dual site phospholamban phosphorylation. J Biol Chem 273: 4734-4739.

23. Foulkes N S, Borrelli E, Sassone-Corsi P. (1991) CREM gene: use of alternative DNA-binding domains generates multiple antagonists of cAMP-induced transcription. Cell 64: 739-749.
24. Most P, Remppis A, Pleger S T, Löffler E, Ehlermann P, et al. (2003) Transgenic overexpression of the Ca2+-binding protein S100A1 in the heart leads to increase in vivo myocardial contractile performance. J Biol Chem 278: 33809-33817.
25. Mayr B, Montminy M. (2001) Transcriptional regulation by the phosphorylation-dependent factor CREB. Nat Rev Mol Cell Biol 2: 599-609.
26. Song W, Zimmer D B. (1996) Expression of the rat S100A1 gene in neurons, glia, and skeletal muscle. Brain Res 721: 204-216.
27. Iancu R V, Ramamurthy G, Harvey R D. (2008) Spatial and temporal aspects of cAMP signaling in cardiac myocytes. Clin Exp Pharmacol Physiol 35: 1343-1348.
28. Efendiev R, Samelson B K, Nguyen B T, Phatarpekar P V, Baameur F, et al. (2010) AKAP79 interacts with multiple adenylyl cyclase (AC) isoforms and scaffolds AC5 and AC6 to α-amino-3-hydroxyl-5-methyl-4-isoxazole-propionate (AMPA) receptors. J Biol Chem 285: 14450-14458.
29. Ostrom R S, Post S R, Insel P A. (2000). Stoichiometry and compartmentation in G protein-coupled receptor signaling: implications for therapeutic interventions involving Gs. J Pharmacol Exp Ther 294:407-412.
30. Gao M H, Lai N C, Roth D M, Zhou J, Zhu J, Anzai T, Dalton N, Hammond H K. (1999) Adenylylcyclase increases responsiveness to catecholamine stimulation in transgenic mice. Circulation 99:1618-1622.

TABLE 1

| Body, LV, and Lung Weight | | | |
|---|---|---|---|
| | AC6mut (23) | TG- Control (16) | p |
| Body (g) | 25.5 ± 0.7 | 25.0 ± 1.2 | 0.7 |
| LV (mg) | 91 ± 2.7 | 89 ± 3.4 | 0.6 |

TABLE 1-continued

| Body, LV, and Lung Weight | | | |
|---|---|---|---|
| | AC6mut (23) | TG- Control (16) | p |
| Tibial Length (mm) | 17 ± 0.1 | 16.7 ± 0.2 | 0.3 |
| LV/Body (mg/g) | 3.6 ± 0.1 | 3.6 ± 0.1 | 0.9 |
| LV/TL (mg/mm) | 5.4 ± 0.1 | 5.3 ± 0.2 | 0.7 |
| Lung (mg) | 150 ± 4.9 | 149 ± 6.7 | 0.9 |
| Lung/Body (mg/g) | 6.0 ± 0.2 | 6.0 ± 0.2 | 0.9 |

LV, left ventricle;
TL, tibial length.
Values represent mean ± SE;
Student's t test (unpaired, 2-tailed).

TABLE 2

| Echocardiography (Basal) | | | |
|---|---|---|---|
| | AC6mut (8) | TG- Control (12) | p |
| HR (bpm) | 501 ± 26 | 506 ± 17 | 0.9 |
| EDD (mm) | 4.2 ± 0.2 | 4.3 ± 0.1 | 0.7 |
| ESD (mm) | 2.9 ± 0.2 | 3.0 ± 0.1 | 0.4 |
| PW Thickness (mm) | 0.6 ± 0.1 | 0.6 ± 0.1 | 0.5 |
| Septal Thickness (mm) | 0.6 ± 0.1 | 0.6 ± 0.1 | 0.4 |
| EDV (μL) | 76 ± 7 | 78 ± 4 | 0.8 |
| ESV (μL) | 25 ± 4 | 27 ± 2 | 0.6 |
| EF (%) | 69 ± 3 | 65 ± 2 | 0.2 |
| CO (μL/min) | 26 ± 2 | 26 ± 2 | 0.8 |
| Vcf (circ/sec) | 7.0 ± 0.7 | 6.2 ± 0.3 | 0.2 |

A number of embodiments of the invention have been described. Nevertheless, it will be understood that various modifications may be made without departing from the spirit and scope of the invention. Accordingly, other embodiments are within the scope of the following claims.

What is claimed is:

1. A method for increasing cardiac function, thereby treating, ameliorating, or reversing the effects of a heart failure in an individual in need thereof, comprising administering via intracoronary injection a nucleic acid comprising a sequence encoding a mutated adenylyl cyclase type 6 (AC6mut) protein having a sequence comprising SEQ ID NO:13, in which an alanine (ala) replaces an aspartic acid (asp) at amino acid residue 426, rendering the AC6mut protein having reduced ability to catalyze the breakdown of ATP to cAMP, thus having reduced capacity to generate increased levels of cAMP, wherein the AC6mut protein is encoded by a nucleic acid operatively linked to a transcriptional regulatory sequence, which comprises a cytomegalovirus (CMV) promoter, an adenylyl cyclase (AC) gene promoter, or a myocyte cell-specific promoter, wherein the AC6mut protein-encoding nucleic acid is contained in an adenovirus vector, wherein the AC6mut protein when expressed causes an increase in ATP-dependent sarcoplasmic reticulum (SR) Ca++ uptake and release and a decrease in phospholamban (PLB) expression and function, thereby increasing cardiac function and treating, ameliorating, or reversing the effects of the heart failure.

2. The method of claim 1, wherein the adenovirus vector is formulated in or as a an aqueous or a saline formulation.

3. The method of claim 1, wherein the adenovirus vector is formulated in a vesicle, a liposome, a nanoliposome, a nanoparticle or a nanolipid particle (NLP).

4. The method of claim 1, wherein the cause of the heart failure comprises an atherosclerosis.

5. The method of claim 1, wherein the cause of the heart failure comprises a thrombosis.

6. The method of claim 1, wherein the cause of the heart failure comprises a restenosis.

7. The method of claim 1, wherein the cause of the heart failure comprises a vasculitis or a viral vasculitis.

8. The method of claim 1, wherein the cause of the heart failure comprises an autoimmune vasculitis.

9. The method of claim 1, wherein the cause of the heart failure comprises an atherosclerotic aneurism.

10. The method of claim 1, wherein the cause of the heart failure comprises Kawasaki Disease.

11. The method of claim 1, wherein the cause of the heart failure comprises a myocardial hypertrophy.

12. The method of claim 1, wherein the cause of the heart failure comprises a congenital heart disease (CHD).

13. The method of claim 1, wherein the cause of the heart failure comprises an ischemic heart disease or an angina.

14. The method of claim 1, wherein the cause of the heart failure comprises an acquired valvular or an endocardial disease.

15. The method of claim 1, wherein the cause of the heart failure comprises an polyarteritis nodosa; a Churg-Strass syndrome; a Takayasu's arteritis; or, a Rickettsial vasculitis.

* * * * *

SEQUENCE LISTING

```
<160> NUMBER OF SEQ ID NOS: 17

<210> SEQ ID NO 1
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 1
cacatagaag cctagcccac acc                                              23

<210> SEQ ID NO 2
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 2
caggaggcca ctaaaccatg ac                                               22

<210> SEQ ID NO 3
<211> LENGTH: 20
```

```
<212> TYPE: DNA
<213> ORGANISM: artificial sequence
<220> FEATURE:
<223> OTHER INFORMATION: synthetic oligonucleotide

<400> SEQUENCE: 3
tgggcctctc tactctgcat                                              20

<210> SEQ ID NO 4
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 4
tggatgtaac ctcgggtctc                                              20

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 5
ggcattgagt gggactttgt                                              20

<210> SEQ ID NO 6
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 6
tctgcatcca aacaaacgaa                                              20

<210> SEQ ID NO 7
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 7
aacctaccag gctgtggatg                                              20

<210> SEQ ID NO 8
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 8
gactcgatgg gcaagtcaat                                              20

<210> SEQ ID NO 9
<211> LENGTH: 30
<212> TYPE: PRT
<213> ORGANISM: artificial sequence
<220> FEATURE:
<223> OTHER INFORMATION: synthetic peptide

<400> SEQUENCE: 9
```

```
Lys Gly Tyr Gln Leu Glu Cys Arg Gly Val Lys Val Lys Gly Lys
1               5                   10                  15

Gly Glu Met Thr Thr Tyr Phe Leu Asn Gly Gly Pro Ser Ser
            20                  25                  30

<210> SEQ ID NO 10
<211> LENGTH: 1168
<212> TYPE: PRT
<213> ORGANISM: homo sapiien

<400> SEQUENCE: 10

Met Ser Trp Phe Ser Gly Leu Leu Val Pro Lys Val Asp Glu Arg Lys
1               5                   10                  15

Thr Ala Trp Gly Glu Arg Asn Gly Gln Lys Arg Ser Arg Arg Arg Gly
                20                  25                  30

Thr Arg Ala Gly Gly Phe Cys Thr Pro Arg Tyr Met Ser Cys Leu Arg
            35                  40                  45

Asp Ala Glu Pro Pro Ser Pro Thr Pro Ala Gly Pro Pro Arg Cys Pro
50                  55                  60

Trp Gln Asp Asp Ala Phe Ile Arg Arg Gly Pro Gly Lys Gly Lys
65                  70                  75                  80

Glu Leu Gly Leu Arg Ala Val Ala Leu Gly Phe Glu Asp Thr Glu Val
                85                  90                  95

Thr Thr Thr Ala Gly Gly Thr Ala Glu Val Ala Pro Asp Ala Val Pro
            100                 105                 110

Arg Ser Gly Arg Ser Cys Trp Arg Arg Leu Val Gln Val Phe Gln Ser
        115                 120                 125

Lys Gln Phe Arg Ser Ala Lys Leu Glu Arg Leu Tyr Gln Arg Tyr Phe
130                 135                 140

Phe Gln Met Asn Gln Ser Ser Leu Thr Leu Leu Met Ala Val Leu Val
145                 150                 155                 160

Leu Leu Thr Ala Val Leu Leu Ala Phe His Ala Ala Pro Ala Arg Pro
                165                 170                 175

Gln Pro Ala Tyr Val Ala Leu Leu Ala Cys Ala Ala Ala Leu Phe Val
            180                 185                 190

Gly Leu Met Val Val Cys Asn Arg His Ser Phe Arg Gln Asp Ser Met
        195                 200                 205

Trp Val Val Ser Tyr Val Val Leu Gly Ile Leu Ala Ala Val Gln Val
210                 215                 220

Gly Gly Ala Leu Ala Ala Asp Pro Arg Ser Pro Ser Ala Gly Leu Trp
225                 230                 235                 240

Cys Pro Val Phe Phe Val Tyr Ile Ala Tyr Thr Leu Leu Pro Ile Arg
                245                 250                 255

Met Arg Ala Ala Val Leu Ser Gly Leu Gly Leu Ser Thr Leu His Leu
            260                 265                 270

Ile Leu Ala Trp Gln Leu Asn Arg Gly Asp Ala Phe Leu Trp Arg Gln
        275                 280                 285

Leu Gly Ala Asn Val Leu Leu Phe Leu Cys Thr Asn Val Ile Gly Ile
290                 295                 300

Cys Thr His Tyr Pro Ala Glu Val Ser Gln Arg Gln Ala Phe Gln Glu
305                 310                 315                 320

Thr Arg Gly Tyr Ile Gln Ala Arg Leu His Leu Gln His Glu Asn Arg
                325                 330                 335

Gln Gln Glu Arg Leu Leu Leu Ser Val Leu Pro Gln His Val Ala Met
            340                 345                 350
```

```
Glu Met Lys Glu Asp Ile Asn Thr Lys Lys Glu Asp Met Met Phe His
            355                 360                 365
Lys Ile Tyr Ile Gln Lys His Asp Asn Val Ser Ile Leu Phe Ala Asp
        370                 375                 380
Ile Glu Gly Phe Thr Ser Leu Ala Ser Gln Cys Thr Ala Gln Glu Leu
385                 390                 395                 400
Val Met Thr Leu Asn Glu Leu Phe Ala Arg Phe Asp Lys Leu Ala Ala
                405                 410                 415
Glu Asn His Cys Leu Arg Ile Lys Ile Leu Gly Asp Cys Tyr Tyr Cys
            420                 425                 430
Val Ser Gly Leu Pro Glu Ala Arg Ala Asp His Ala His Cys Cys Val
        435                 440                 445
Glu Met Gly Val Asp Met Ile Glu Ala Ile Ser Leu Val Arg Glu Val
        450                 455                 460
Thr Gly Val Asn Val Asn Met Arg Val Gly Ile His Ser Gly Arg Val
465                 470                 475                 480
His Cys Gly Val Leu Gly Leu Arg Lys Trp Gln Phe Asp Val Trp Ser
                485                 490                 495
Asn Asp Val Thr Leu Ala Asn His Met Glu Ala Gly Gly Arg Ala Gly
            500                 505                 510
Arg Ile His Ile Thr Arg Ala Thr Leu Gln Tyr Leu Asn Gly Asp Tyr
        515                 520                 525
Glu Val Glu Pro Gly Arg Gly Gly Glu Arg Asn Ala Tyr Leu Lys Glu
        530                 535                 540
Gln His Ile Glu Thr Phe Leu Ile Leu Gly Ala Ser Gln Lys Arg Lys
545                 550                 555                 560
Glu Glu Lys Ala Met Leu Ala Lys Leu Gln Arg Thr Arg Ala Asn Ser
                565                 570                 575
Met Glu Gly Leu Met Pro Arg Trp Val Pro Asp Arg Ala Phe Ser Arg
            580                 585                 590
Thr Lys Asp Ser Lys Ala Phe Arg Gln Met Gly Ile Asp Asp Ser Ser
        595                 600                 605
Lys Asp Asn Arg Gly Thr Gln Asp Ala Leu Asn Pro Glu Asp Glu Val
        610                 615                 620
Asp Glu Phe Leu Ser Arg Ala Ile Asp Ala Arg Ser Ile Asp Gln Leu
625                 630                 635                 640
Arg Lys Asp His Val Arg Arg Phe Leu Leu Thr Phe Gln Arg Glu Asp
                645                 650                 655
Leu Glu Lys Lys Tyr Ser Arg Lys Val Asp Pro Arg Phe Gly Ala Tyr
            660                 665                 670
Val Ala Cys Ala Leu Leu Val Phe Cys Phe Ile Cys Phe Ile Gln Leu
        675                 680                 685
Leu Ile Phe Pro His Ser Thr Leu Met Leu Gly Ile Tyr Ala Ser Ile
        690                 695                 700
Phe Leu Leu Leu Leu Ile Thr Val Leu Ile Cys Ala Val Tyr Ser Cys
705                 710                 715                 720
Gly Ser Leu Phe Pro Lys Ala Leu Gln Arg Leu Ser Arg Ser Ile Val
                725                 730                 735
Arg Ser Arg Ala His Ser Thr Ala Val Gly Ile Phe Ser Val Leu Leu
            740                 745                 750
Val Phe Thr Ser Ala Ile Ala Asn Met Phe Thr Cys Asn His Thr Pro
        755                 760                 765
```

```
Ile Arg Ser Cys Ala Ala Arg Met Leu Asn Leu Thr Pro Ala Asp Ile
770                 775                 780

Thr Ala Cys His Leu Gln Gln Leu Asn Tyr Ser Leu Gly Leu Asp Ala
785                 790                 795                 800

Pro Leu Cys Glu Gly Thr Met Pro Thr Cys Ser Phe Pro Glu Tyr Phe
                805                 810                 815

Ile Gly Asn Met Leu Leu Ser Leu Leu Ala Ser Ser Val Phe Leu His
                820                 825                 830

Ile Ser Ser Ile Gly Lys Leu Ala Met Ile Phe Val Leu Gly Leu Ile
            835                 840                 845

Tyr Leu Val Leu Leu Leu Gly Pro Pro Ala Thr Ile Phe Asp Asn
850                 855                 860

Tyr Asp Leu Leu Leu Gly Val His Gly Leu Ala Ser Ser Asn Glu Thr
865                 870                 875                 880

Phe Asp Gly Leu Asp Cys Pro Ala Ala Gly Arg Val Ala Leu Lys Tyr
                885                 890                 895

Met Thr Pro Val Ile Leu Leu Val Phe Ala Leu Ala Leu Tyr Leu His
                900                 905                 910

Ala Gln Gln Val Glu Ser Thr Ala Arg Leu Asp Phe Leu Trp Lys Leu
            915                 920                 925

Gln Ala Thr Gly Glu Lys Glu Glu Met Glu Glu Leu Gln Ala Tyr Asn
930                 935                 940

Arg Arg Leu Leu His Asn Ile Leu Pro Lys Asp Val Ala Ala His Phe
945                 950                 955                 960

Leu Ala Arg Glu Arg Arg Asn Asp Glu Leu Tyr Tyr Gln Ser Cys Glu
                965                 970                 975

Cys Val Ala Val Met Phe Ala Ser Ile Ala Asn Phe Ser Glu Phe Tyr
                980                 985                 990

Val Glu Leu Glu Ala Asn Asn Glu Gly Val Glu Cys Leu Arg Leu Leu
            995                 1000                1005

Asn Glu Ile Ile Ala Asp Phe Asp Glu Ile Ile Ser Glu Glu Arg
1010                1015                1020

Phe Arg Gln Leu Glu Lys Ile Lys Thr Ile Gly Ser Thr Tyr Met
1025                1030                1035

Ala Ala Ser Gly Leu Asn Ala Ser Thr Tyr Asp Gln Val Gly Arg
1040                1045                1050

Ser His Ile Thr Ala Leu Ala Asp Tyr Ala Met Arg Leu Met Glu
1055                1060                1065

Gln Met Lys His Ile Asn Glu His Ser Phe Asn Asn Phe Gln Met
1070                1075                1080

Lys Ile Gly Leu Asn Met Gly Pro Val Val Ala Gly Val Ile Gly
1085                1090                1095

Ala Arg Lys Pro Gln Tyr Asp Ile Trp Gly Asn Thr Val Asn Val
1100                1105                1110

Ser Ser Arg Met Asp Ser Thr Gly Val Pro Asp Arg Ile Gln Val
1115                1120                1125

Thr Thr Asp Leu Tyr Gln Val Leu Ala Ala Lys Gly Tyr Gln Leu
1130                1135                1140

Glu Cys Arg Gly Val Val Lys Val Lys Gly Lys Gly Glu Met Thr
1145                1150                1155

Thr Tyr Phe Leu Asn Gly Gly Pro Ser Ser
1160                1165
```

<210> SEQ ID NO 11
<211> LENGTH: 1176
<212> TYPE: PRT
<213> ORGANISM: mus musculus

<400> SEQUENCE: 11

```
Met Pro Thr Ser Pro Arg Pro Val Ala Ser Met Ser Trp Phe Ser Gly
1               5                   10                  15

Leu Leu Val Pro Lys Val Asp Glu Arg Lys Thr Ala Trp Gly Glu Arg
            20                  25                  30

Asn Gly Gln Lys Arg Pro Arg His Ala Asn Arg Ala Ser Gly Phe Cys
        35                  40                  45

Ala Pro Arg Tyr Met Ser Cys Leu Lys Asn Ala Glu Pro Pro Ser Pro
    50                  55                  60

Thr Pro Ala Ala His Thr Arg Cys Pro Trp Gln Asp Glu Ala Phe Ile
65                  70                  75                  80

Arg Arg Ala Gly Pro Gly Arg Gly Val Glu Leu Gly Leu Arg Ser Val
                85                  90                  95

Ala Leu Gly Phe Asp Asp Thr Glu Val Thr Thr Pro Met Gly Thr Ala
            100                 105                 110

Glu Val Ala Pro Asp Thr Ser Pro Arg Ser Gly Pro Ser Cys Trp His
        115                 120                 125

Arg Leu Val Gln Val Phe Gln Ser Lys Gln Phe Arg Ser Ala Lys Leu
    130                 135                 140

Glu Arg Leu Tyr Gln Arg Tyr Phe Phe Gln Met Asn Gln Ser Ser Leu
145                 150                 155                 160

Thr Leu Leu Met Ala Val Leu Val Leu Leu Met Ala Val Leu Leu Thr
                165                 170                 175

Phe His Ala Ala Pro Ala Gln Pro Gln Pro Ala Tyr Val Ala Leu Leu
            180                 185                 190

Thr Cys Ala Ser Val Leu Phe Val Val Leu Met Val Val Cys Asn Arg
        195                 200                 205

His Ser Phe Arg Gln Asp Ser Met Trp Val Val Ser Tyr Val Val Leu
    210                 215                 220

Gly Ile Leu Ala Ala Val Gln Val Gly Gly Ala Leu Ala Ala Asn Pro
225                 230                 235                 240

His Ser Pro Ser Ala Gly Leu Trp Cys Pro Val Phe Phe Val Tyr Ile
                245                 250                 255

Thr Tyr Thr Leu Leu Pro Ile Arg Met Arg Ala Ala Val Leu Ser Gly
            260                 265                 270

Leu Gly Leu Ser Thr Leu His Leu Ile Leu Ala Trp Gln Leu Asn Ser
        275                 280                 285

Ser Asp Pro Phe Leu Trp Lys Gln Leu Gly Ala Asn Val Val Leu Phe
    290                 295                 300

Leu Cys Thr Asn Ala Ile Gly Val Cys Thr His Tyr Pro Ala Glu Val
305                 310                 315                 320

Ser Gln Arg Gln Ala Phe Gln Glu Thr Arg Gly Tyr Ile Gln Ala Arg
                325                 330                 335

Leu His Leu Gln His Glu Asn Arg Gln Glu Arg Leu Leu Leu Ser
            340                 345                 350

Val Leu Pro Gln His Val Ala Met Glu Met Lys Glu Asp Ile Asn Thr
        355                 360                 365

Lys Lys Glu Asp Met Met Phe His Lys Ile Tyr Ile Gln Lys His Asp
    370                 375                 380
```

```
Asn Val Ser Ile Leu Phe Ala Asp Ile Glu Gly Phe Thr Ser Leu Ala
385                 390                 395                 400

Ser Gln Cys Thr Ala Gln Glu Leu Val Met Thr Leu Asn Glu Leu Phe
        405                 410                 415

Ala Arg Phe Asp Lys Leu Ala Ala Glu Asn His Cys Leu Arg Ile Lys
            420                 425                 430

Ile Leu Gly Asp Cys Tyr Tyr Cys Val Ser Gly Leu Pro Glu Ala Arg
        435                 440                 445

Ala Asp His Ala His Cys Cys Val Glu Met Gly Val Asp Met Ile Glu
    450                 455                 460

Ala Ile Ser Leu Val Arg Glu Val Thr Gly Val Asn Val Asn Met Arg
465                 470                 475                 480

Val Gly Ile His Ser Gly Arg Val His Cys Gly Val Leu Gly Leu Arg
                485                 490                 495

Lys Trp Gln Phe Asp Val Trp Ser Asn Asp Val Thr Leu Ala Asn His
            500                 505                 510

Met Glu Ala Gly Gly Arg Ala Gly Arg Ile His Ile Thr Arg Ala Thr
            515                 520                 525

Leu Gln Tyr Leu Asn Gly Asp Tyr Glu Val Glu Pro Gly Arg Gly Gly
        530                 535                 540

Glu Arg Asn Ala Tyr Leu Lys Glu Gln Cys Ile Glu Thr Phe Leu Ile
545                 550                 555                 560

Leu Gly Ala Ser Gln Lys Arg Lys Glu Lys Ala Met Leu Ala Lys
                565                 570                 575

Leu Gln Arg Thr Arg Ala Asn Ser Met Glu Gly Leu Met Pro Arg Trp
            580                 585                 590

Val Pro Asp Arg Ala Phe Ser Arg Thr Lys Asp Ser Lys Ala Phe Arg
        595                 600                 605

Gln Met Gly Ile Asp Asp Ser Ser Lys Asp Asn Arg Gly Ala Gln Asp
    610                 615                 620

Ala Leu Asn Pro Glu Asp Glu Val Asp Glu Phe Leu Gly Arg Ala Ile
625                 630                 635                 640

Asp Ala Arg Ser Ile Asp Gln Leu Arg Lys Asp His Val Arg Arg Phe
                645                 650                 655

Leu Leu Thr Phe Gln Arg Glu Asp Leu Glu Lys Lys Tyr Ser Arg Lys
            660                 665                 670

Val Asp Pro Arg Phe Gly Ala Tyr Val Ala Cys Ala Leu Leu Val Phe
        675                 680                 685

Cys Phe Ile Cys Phe Ile Gln Leu Leu Val Phe Pro Tyr Ser Thr Leu
    690                 695                 700

Ile Leu Gly Ile Tyr Ala Ala Ile Phe Leu Leu Leu Val Thr Val
705                 710                 715                 720

Leu Ile Cys Ala Val Cys Ser Cys Gly Ser Phe Phe Pro Lys Ala Leu
                725                 730                 735

Gln Arg Leu Ser Arg Asn Ile Val Arg Ser Arg Val His Ser Thr Ala
            740                 745                 750

Val Gly Ile Phe Ser Val Leu Leu Val Phe Ile Ser Ala Ile Ala Asn
        755                 760                 765

Met Phe Thr Cys Asn His Thr Pro Ile Arg Thr Cys Ala Ala Arg Met
    770                 775                 780

Leu Asn Leu Thr Pro Ala Asp Val Thr Ala Cys His Leu Gln Gln Leu
785                 790                 795                 800

Asn Tyr Ser Leu Gly Leu Asp Ala Pro Leu Cys Glu Gly Thr Ala Pro
```

```
            805                 810                 815
Thr Cys Ser Phe Pro Glu Tyr Phe Val Gly Asn Val Leu Leu Ser Leu
        820                 825                 830

Leu Ala Ser Ser Val Phe Leu His Ile Ser Ser Ile Gly Lys Leu Ala
        835                 840                 845

Met Thr Phe Ile Leu Gly Phe Thr Tyr Leu Val Leu Leu Leu Leu Gly
850                 855                 860

Pro Pro Ala Ala Ile Phe Asp Asn Tyr Asp Leu Leu Leu Gly Val His
865                 870                 875                 880

Gly Leu Ala Ser Ser Asn Glu Thr Phe Asp Gly Leu Asp Cys Pro Ala
                885                 890                 895

Val Gly Arg Val Ala Leu Lys Tyr Met Thr Pro Val Ile Leu Leu Val
            900                 905                 910

Phe Ala Leu Ala Leu Tyr Leu His Ala Gln Gln Val Glu Ser Thr Ala
            915                 920                 925

Arg Leu Asp Phe Leu Trp Lys Leu Gln Ala Thr Gly Glu Lys Glu Glu
        930                 935                 940

Met Glu Glu Leu Gln Ala Tyr Asn Arg Arg Leu Leu His Asn Ile Leu
945                 950                 955                 960

Pro Lys Asp Val Ala Ala His Phe Leu Ala Arg Glu Arg Arg Asn Asp
                965                 970                 975

Glu Leu Tyr Tyr Gln Ser Cys Glu Cys Val Ala Val Met Phe Ala Ser
            980                 985                 990

Ile Ala Asn Phe Ser Glu Phe Tyr  Val Glu Leu Glu Ala  Asn Asn Glu
            995                  1000                 1005

Gly Val Glu Cys Leu Arg Leu  Leu Asn Glu Ile Ile  Ala Asp Phe
    1010                1015                 1020

Asp Glu Ile Ile Ser Glu Glu  Arg Phe Arg Gln Leu  Glu Lys Ile
    1025                1030                 1035

Lys Thr Ile Gly Ser Thr Tyr  Met Ala Ala Ser Gly  Leu Asn Ala
    1040                1045                 1050

Ser Thr Tyr Asp Gln Val Gly  Arg Ser His Ile Thr  Ala Leu Ala
    1055                1060                 1065

Asp Tyr Ala Met Arg Leu Met  Glu Gln Met Lys His  Ile Asn Glu
    1070                1075                 1080

His Ser Phe Asn Asn Phe Gln  Met Lys Ile Gly Leu  Asn Met Gly
    1085                1090                 1095

Pro Val Val Ala Gly Val Ile  Gly Ala Arg Lys Pro  Gln Tyr Asp
    1100                1105                 1110

Ile Trp Gly Asn Thr Val Asn  Val Ser Ser Arg Met  Asp Ser Thr
    1115                1120                 1125

Gly Val Pro Asp Arg Ile Gln  Val Thr Thr Asp Leu  Tyr Gln Val
    1130                1135                 1140

Leu Ala Ala Lys Gly Tyr Gln  Leu Glu Cys Arg Gly  Val Val Lys
    1145                1150                 1155

Val Lys Gly Lys Gly Glu Met  Thr Thr Tyr Phe Leu  Asn Gly Gly
    1160                1165                 1170

Pro Ser Ser
    1175

<210> SEQ ID NO 12
<211> LENGTH: 1176
<212> TYPE: PRT
<213> ORGANISM: artificial sequence
```

<220> FEATURE:
<223> OTHER INFORMATION: synthetic polypeptide

<400> SEQUENCE: 12

```
Met Pro Thr Ser Pro Arg Pro Val Ala Ser Met Ser Trp Phe Ser Gly
1               5                   10                  15

Leu Leu Val Pro Lys Val Asp Glu Arg Lys Thr Ala Trp Gly Glu Arg
            20                  25                  30

Asn Gly Gln Lys Arg Pro Arg His Ala Asn Arg Ala Ser Gly Phe Cys
        35                  40                  45

Ala Pro Arg Tyr Met Ser Cys Leu Lys Asn Ala Glu Pro Pro Ser Pro
    50                  55                  60

Thr Pro Ala Ala His Thr Arg Cys Pro Trp Gln Asp Glu Ala Phe Ile
65                  70                  75                  80

Arg Arg Ala Gly Pro Gly Arg Gly Val Glu Leu Gly Leu Arg Ser Val
                85                  90                  95

Ala Leu Gly Phe Asp Asp Thr Glu Val Thr Thr Pro Met Gly Thr Ala
            100                 105                 110

Glu Val Ala Pro Asp Thr Ser Pro Arg Ser Gly Pro Ser Cys Trp His
        115                 120                 125

Arg Leu Val Gln Val Phe Gln Ser Lys Gln Phe Arg Ser Ala Lys Leu
    130                 135                 140

Glu Arg Leu Tyr Gln Arg Tyr Phe Phe Gln Met Asn Gln Ser Ser Leu
145                 150                 155                 160

Thr Leu Leu Met Ala Val Leu Val Leu Leu Met Ala Val Leu Leu Thr
                165                 170                 175

Phe His Ala Ala Pro Ala Gln Pro Gln Pro Ala Tyr Val Ala Leu Leu
            180                 185                 190

Thr Cys Ala Ser Val Leu Phe Val Val Leu Met Val Val Cys Asn Arg
        195                 200                 205

His Ser Phe Arg Gln Asp Ser Met Trp Val Val Ser Tyr Val Val Leu
    210                 215                 220

Gly Ile Leu Ala Ala Val Gln Val Gly Gly Ala Leu Ala Ala Asn Pro
225                 230                 235                 240

His Ser Pro Ser Ala Gly Leu Trp Cys Pro Val Phe Phe Val Tyr Ile
                245                 250                 255

Thr Tyr Thr Leu Leu Pro Ile Arg Met Arg Ala Ala Val Leu Ser Gly
            260                 265                 270

Leu Gly Leu Ser Thr Leu His Leu Ile Leu Ala Trp Gln Leu Asn Ser
        275                 280                 285

Ser Asp Pro Phe Leu Trp Lys Gln Leu Gly Ala Asn Val Val Leu Phe
    290                 295                 300

Leu Cys Thr Asn Ala Ile Gly Val Cys Thr His Tyr Pro Ala Glu Val
305                 310                 315                 320

Ser Gln Arg Gln Ala Phe Gln Glu Thr Arg Gly Tyr Ile Gln Ala Arg
                325                 330                 335

Leu His Leu Gln His Glu Asn Arg Gln Gln Glu Arg Leu Leu Leu Ser
            340                 345                 350

Val Leu Pro Gln His Val Ala Met Glu Met Lys Glu Asp Ile Asn Thr
        355                 360                 365

Lys Lys Glu Asp Met Met Phe His Lys Ile Tyr Ile Gln Lys His Asp
    370                 375                 380

Asn Val Ser Ile Leu Phe Ala Asp Ile Glu Gly Phe Thr Ser Leu Ala
385                 390                 395                 400
```

```
Ser Gln Cys Thr Ala Gln Glu Leu Val Met Thr Leu Asn Glu Leu Phe
                405                 410                 415
Ala Arg Phe Asp Lys Leu Ala Ala Glu Asn His Cys Leu Arg Ile Lys
            420                 425                 430
Ile Leu Gly Ala Cys Tyr Tyr Cys Val Ser Gly Leu Pro Glu Ala Arg
        435                 440                 445
Ala Asp His Ala His Cys Cys Val Glu Met Gly Val Asp Met Ile Glu
    450                 455                 460
Ala Ile Ser Leu Val Arg Glu Val Thr Gly Val Asn Val Asn Met Arg
465                 470                 475                 480
Val Gly Ile His Ser Gly Arg Val His Cys Gly Val Leu Gly Leu Arg
            485                 490                 495
Lys Trp Gln Phe Asp Val Trp Ser Asn Asp Val Thr Leu Ala Asn His
        500                 505                 510
Met Glu Ala Gly Gly Arg Ala Gly Arg Ile His Ile Thr Arg Ala Thr
    515                 520                 525
Leu Gln Tyr Leu Asn Gly Asp Tyr Glu Val Glu Pro Gly Arg Gly Gly
        530                 535                 540
Glu Arg Asn Ala Tyr Leu Lys Glu Gln Cys Ile Glu Thr Phe Leu Ile
545                 550                 555                 560
Leu Gly Ala Ser Gln Lys Arg Lys Glu Glu Lys Ala Met Leu Ala Lys
            565                 570                 575
Leu Gln Arg Thr Arg Ala Asn Ser Met Glu Gly Leu Met Pro Arg Trp
            580                 585                 590
Val Pro Asp Arg Ala Phe Ser Arg Thr Lys Asp Ser Lys Ala Phe Arg
        595                 600                 605
Gln Met Gly Ile Asp Asp Ser Ser Lys Asp Asn Arg Gly Ala Gln Asp
    610                 615                 620
Ala Leu Asn Pro Glu Asp Glu Val Asp Glu Phe Leu Gly Arg Ala Ile
625                 630                 635                 640
Asp Ala Arg Ser Ile Asp Gln Leu Arg Lys Asp His Val Arg Arg Phe
            645                 650                 655
Leu Leu Thr Phe Gln Arg Glu Asp Leu Glu Lys Lys Tyr Ser Arg Lys
            660                 665                 670
Val Asp Pro Arg Phe Gly Ala Tyr Val Ala Cys Ala Leu Leu Val Phe
        675                 680                 685
Cys Phe Ile Cys Phe Ile Gln Leu Leu Val Phe Pro Tyr Ser Thr Leu
    690                 695                 700
Ile Leu Gly Ile Tyr Ala Ala Ile Phe Leu Leu Leu Val Thr Val
705                 710                 715                 720
Leu Ile Cys Ala Val Cys Ser Cys Gly Ser Phe Phe Pro Lys Ala Leu
            725                 730                 735
Gln Arg Leu Ser Arg Asn Ile Val Arg Ser Arg Val His Ser Thr Ala
            740                 745                 750
Val Gly Ile Phe Ser Val Leu Leu Val Phe Ile Ser Ala Ile Ala Asn
        755                 760                 765
Met Phe Thr Cys Asn His Thr Pro Ile Arg Thr Cys Ala Ala Arg Met
    770                 775                 780
Leu Asn Leu Thr Pro Ala Asp Val Thr Ala Cys His Leu Gln Gln Leu
785                 790                 795                 800
Asn Tyr Ser Leu Gly Leu Asp Ala Pro Leu Cys Glu Gly Thr Ala Pro
            805                 810                 815
```

```
Thr Cys Ser Phe Pro Glu Tyr Phe Val Gly Asn Val Leu Leu Ser Leu
            820                 825                 830

Leu Ala Ser Ser Val Phe Leu His Ile Ser Ser Ile Gly Lys Leu Ala
            835                 840                 845

Met Thr Phe Ile Leu Gly Phe Thr Tyr Leu Val Leu Leu Leu Leu Gly
            850                 855                 860

Pro Pro Ala Ala Ile Phe Asp Asn Tyr Asp Leu Leu Leu Gly Val His
865                 870                 875                 880

Gly Leu Ala Ser Ser Asn Glu Thr Phe Asp Gly Leu Asp Cys Pro Ala
                    885                 890                 895

Val Gly Arg Val Ala Leu Lys Tyr Met Thr Pro Val Ile Leu Leu Val
            900                 905                 910

Phe Ala Leu Ala Leu Tyr Leu His Ala Gln Gln Val Glu Ser Thr Ala
            915                 920                 925

Arg Leu Asp Phe Leu Trp Lys Leu Gln Ala Thr Gly Glu Lys Glu Glu
            930                 935                 940

Met Glu Glu Leu Gln Ala Tyr Asn Arg Arg Leu Leu His Asn Ile Leu
945                 950                 955                 960

Pro Lys Asp Val Ala Ala His Phe Leu Ala Arg Glu Arg Arg Asn Asp
                    965                 970                 975

Glu Leu Tyr Tyr Gln Ser Cys Glu Cys Val Ala Val Met Phe Ala Ser
            980                 985                 990

Ile Ala Asn Phe Ser Glu Phe Tyr Val Glu Leu Glu Ala Asn Asn Glu
            995                 1000                1005

Gly Val Glu Cys Leu Arg Leu Leu Asn Glu Ile Ile Ala Asp Phe
            1010                1015                1020

Asp Glu Ile Ile Ser Glu Glu Arg Phe Arg Gln Leu Glu Lys Ile
            1025                1030                1035

Lys Thr Ile Gly Ser Thr Tyr Met Ala Ala Ser Gly Leu Asn Ala
            1040                1045                1050

Ser Thr Tyr Asp Gln Val Gly Arg Ser His Ile Thr Ala Leu Ala
            1055                1060                1065

Asp Tyr Ala Met Arg Leu Met Glu Gln Met Lys His Ile Asn Glu
            1070                1075                1080

His Ser Phe Asn Asn Phe Gln Met Lys Ile Gly Leu Asn Met Gly
            1085                1090                1095

Pro Val Val Ala Gly Val Ile Gly Ala Arg Lys Pro Gln Tyr Asp
1100                1105                1110

Ile Trp Gly Asn Thr Val Asn Val Ser Ser Arg Met Asp Ser Thr
            1115                1120                1125

Gly Val Pro Asp Arg Ile Gln Val Thr Thr Asp Leu Tyr Gln Val
            1130                1135                1140

Leu Ala Ala Lys Gly Tyr Gln Leu Glu Cys Arg Gly Val Val Lys
            1145                1150                1155

Val Lys Gly Lys Gly Glu Met Thr Thr Tyr Phe Leu Asn Gly Gly
            1160                1165                1170

Pro Ser Ser
    1175

<210> SEQ ID NO 13
<211> LENGTH: 1168
<212> TYPE: PRT
<213> ORGANISM: artificial sequence
<220> FEATURE:
<223> OTHER INFORMATION: synthetic polypeptide
```

<400> SEQUENCE: 13

```
Met Ser Trp Phe Ser Gly Leu Leu Val Pro Lys Val Asp Glu Arg Lys
1               5                   10                  15

Thr Ala Trp Gly Glu Arg Asn Gly Gln Lys Arg Ser Arg Arg Arg Gly
            20                  25                  30

Thr Arg Ala Gly Gly Phe Cys Thr Pro Arg Tyr Met Ser Cys Leu Arg
        35                  40                  45

Asp Ala Glu Pro Pro Ser Pro Thr Pro Ala Gly Pro Pro Arg Cys Pro
    50                  55                  60

Trp Gln Asp Asp Ala Phe Ile Arg Arg Gly Gly Pro Gly Lys Gly Lys
65                  70                  75                  80

Glu Leu Gly Leu Arg Ala Val Ala Leu Gly Phe Glu Asp Thr Glu Val
                85                  90                  95

Thr Thr Thr Ala Gly Gly Thr Ala Glu Val Ala Pro Asp Ala Val Pro
            100                 105                 110

Arg Ser Gly Arg Ser Cys Trp Arg Arg Leu Val Gln Val Phe Gln Ser
        115                 120                 125

Lys Gln Phe Arg Ser Ala Lys Leu Glu Arg Leu Tyr Gln Arg Tyr Phe
    130                 135                 140

Phe Gln Met Asn Gln Ser Ser Leu Thr Leu Leu Met Ala Val Leu Val
145                 150                 155                 160

Leu Leu Thr Ala Val Leu Leu Ala Phe His Ala Ala Pro Ala Arg Pro
                165                 170                 175

Gln Pro Ala Tyr Val Ala Leu Leu Ala Cys Ala Ala Ala Leu Phe Val
            180                 185                 190

Gly Leu Met Val Val Cys Asn Arg His Ser Phe Arg Gln Asp Ser Met
        195                 200                 205

Trp Val Val Ser Tyr Val Val Leu Gly Ile Leu Ala Ala Val Gln Val
    210                 215                 220

Gly Gly Ala Leu Ala Ala Asp Pro Arg Ser Pro Ser Ala Gly Leu Trp
225                 230                 235                 240

Cys Pro Val Phe Phe Val Tyr Ile Ala Tyr Thr Leu Leu Pro Ile Arg
                245                 250                 255

Met Arg Ala Ala Val Leu Ser Gly Leu Gly Leu Ser Thr Leu His Leu
            260                 265                 270

Ile Leu Ala Trp Gln Leu Asn Arg Gly Asp Ala Phe Leu Trp Arg Gln
        275                 280                 285

Leu Gly Ala Asn Val Leu Leu Phe Leu Cys Thr Asn Val Ile Gly Ile
    290                 295                 300

Cys Thr His Tyr Pro Ala Glu Val Ser Gln Arg Gln Ala Phe Gln Glu
305                 310                 315                 320

Thr Arg Gly Tyr Ile Gln Ala Arg Leu His Leu Gln His Glu Asn Arg
                325                 330                 335

Gln Gln Glu Arg Leu Leu Leu Ser Val Leu Pro Gln His Val Ala Met
            340                 345                 350

Glu Met Lys Glu Asp Ile Asn Thr Lys Lys Glu Asp Met Met Phe His
        355                 360                 365

Lys Ile Tyr Ile Gln Lys His Asp Asn Val Ser Ile Leu Phe Ala Asp
    370                 375                 380

Ile Glu Gly Phe Thr Ser Leu Ala Ser Gln Cys Thr Ala Gln Glu Leu
385                 390                 395                 400

Val Met Thr Leu Asn Glu Leu Phe Ala Arg Phe Asp Lys Leu Ala Ala
```

```
            405                 410                 415
Glu Asn His Cys Leu Arg Ile Lys Ile Leu Gly Ala Cys Tyr Tyr Cys
                420                 425                 430
Val Ser Gly Leu Pro Glu Ala Arg Ala Asp His Ala His Cys Cys Val
            435                 440                 445
Glu Met Gly Val Asp Met Ile Glu Ala Ile Ser Leu Val Arg Glu Val
            450                 455                 460
Thr Gly Val Asn Val Asn Met Arg Val Gly Ile His Ser Gly Arg Val
465                 470                 475                 480
His Cys Gly Val Leu Gly Leu Arg Lys Trp Gln Phe Asp Val Trp Ser
                485                 490                 495
Asn Asp Val Thr Leu Ala Asn His Met Glu Ala Gly Gly Arg Ala Gly
            500                 505                 510
Arg Ile His Ile Thr Arg Ala Thr Leu Gln Tyr Leu Asn Gly Asp Tyr
            515                 520                 525
Glu Val Glu Pro Gly Arg Gly Gly Glu Arg Asn Ala Tyr Leu Lys Glu
            530                 535                 540
Gln His Ile Glu Thr Phe Leu Ile Leu Gly Ala Ser Gln Lys Arg Lys
545                 550                 555                 560
Glu Glu Lys Ala Met Leu Ala Lys Leu Gln Arg Thr Arg Ala Asn Ser
                565                 570                 575
Met Glu Gly Leu Met Pro Arg Trp Val Pro Asp Arg Ala Phe Ser Arg
            580                 585                 590
Thr Lys Asp Ser Lys Ala Phe Arg Gln Met Gly Ile Asp Asp Ser Ser
            595                 600                 605
Lys Asp Asn Arg Gly Thr Gln Asp Ala Leu Asn Pro Glu Asp Glu Val
            610                 615                 620
Asp Glu Phe Leu Ser Arg Ala Ile Asp Ala Arg Ser Ile Asp Gln Leu
625                 630                 635                 640
Arg Lys Asp His Val Arg Arg Phe Leu Leu Thr Phe Gln Arg Glu Asp
                645                 650                 655
Leu Glu Lys Lys Tyr Ser Arg Lys Val Asp Pro Arg Phe Gly Ala Tyr
            660                 665                 670
Val Ala Cys Ala Leu Leu Val Phe Cys Phe Ile Cys Phe Ile Gln Leu
            675                 680                 685
Leu Ile Phe Pro His Ser Thr Leu Met Leu Gly Ile Tyr Ala Ser Ile
            690                 695                 700
Phe Leu Leu Leu Leu Ile Thr Val Leu Ile Cys Ala Val Tyr Ser Cys
705                 710                 715                 720
Gly Ser Leu Phe Pro Lys Ala Leu Gln Arg Leu Ser Arg Ser Ile Val
                725                 730                 735
Arg Ser Arg Ala His Ser Thr Ala Val Gly Ile Phe Ser Val Leu Leu
            740                 745                 750
Val Phe Thr Ser Ala Ile Ala Asn Met Phe Thr Cys Asn His Thr Pro
            755                 760                 765
Ile Arg Ser Cys Ala Ala Arg Met Leu Asn Leu Thr Pro Ala Asp Ile
            770                 775                 780
Thr Ala Cys His Leu Gln Gln Leu Asn Tyr Ser Leu Gly Leu Asp Ala
785                 790                 795                 800
Pro Leu Cys Glu Gly Thr Met Pro Thr Cys Ser Phe Pro Glu Tyr Phe
                805                 810                 815
Ile Gly Asn Met Leu Leu Ser Leu Leu Ala Ser Ser Val Phe Leu His
            820                 825                 830
```

Ile Ser Ser Ile Gly Lys Leu Ala Met Ile Phe Val Leu Gly Leu Ile
    835                 840                 845

Tyr Leu Val Leu Leu Leu Gly Pro Pro Ala Thr Ile Phe Asp Asn
    850                 855                 860

Tyr Asp Leu Leu Leu Gly Val His Gly Leu Ala Ser Asn Glu Thr
865                 870                 875                 880

Phe Asp Gly Leu Asp Cys Pro Ala Ala Gly Arg Val Ala Leu Lys Tyr
                885                 890                 895

Met Thr Pro Val Ile Leu Leu Val Phe Ala Leu Ala Leu Tyr Leu His
            900                 905                 910

Ala Gln Gln Val Glu Ser Thr Ala Arg Leu Asp Phe Leu Trp Lys Leu
            915                 920                 925

Gln Ala Thr Gly Glu Lys Glu Glu Met Glu Glu Leu Gln Ala Tyr Asn
        930                 935                 940

Arg Arg Leu Leu His Asn Ile Leu Pro Lys Asp Val Ala Ala His Phe
945                 950                 955                 960

Leu Ala Arg Glu Arg Arg Asn Asp Glu Leu Tyr Tyr Gln Ser Cys Glu
                965                 970                 975

Cys Val Ala Val Met Phe Ala Ser Ile Ala Asn Phe Ser Glu Phe Tyr
            980                 985                 990

Val Glu Leu Glu Ala Asn Asn Glu Gly Val Glu Cys Leu Arg Leu Leu
            995                1000                1005

Asn Glu Ile Ile Ala Asp Phe Asp Glu Ile Ile Ser Glu Glu Arg
1010                1015                1020

Phe Arg Gln Leu Glu Lys Ile Lys Thr Ile Gly Ser Thr Tyr Met
1025                1030                1035

Ala Ala Ser Gly Leu Asn Ala Ser Thr Tyr Asp Gln Val Gly Arg
1040                1045                1050

Ser His Ile Thr Ala Leu Ala Asp Tyr Ala Met Arg Leu Met Glu
1055                1060                1065

Gln Met Lys His Ile Asn Glu His Ser Phe Asn Asn Phe Gln Met
1070                1075                1080

Lys Ile Gly Leu Asn Met Gly Pro Val Val Ala Gly Val Ile Gly
1085                1090                1095

Ala Arg Lys Pro Gln Tyr Asp Ile Trp Gly Asn Thr Val Asn Val
1100                1105                1110

Ser Ser Arg Met Asp Ser Thr Gly Val Pro Asp Arg Ile Gln Val
1115                1120                1125

Thr Thr Asp Leu Tyr Gln Val Leu Ala Ala Lys Gly Tyr Gln Leu
1130                1135                1140

Glu Cys Arg Gly Val Val Lys Val Lys Gly Lys Gly Glu Met Thr
1145                1150                1155

Thr Tyr Phe Leu Asn Gly Gly Pro Ser Ser
1160                1165

<210> SEQ ID NO 14
<211> LENGTH: 3537
<212> TYPE: DNA
<213> ORGANISM: homo sapiens
<220> FEATURE:
<221> NAME/KEY: misc_feature
<222> LOCATION: (163)..(163)
<223> OTHER INFORMATION: n is a, c, g, or t

<400> SEQUENCE: 14

```
gaattcgccc ttcggcagca tgtcatggtt tagtggcctc ctggtcccta aagtggatga      60
acggaaaaca gcctggggtg aacgcaatgg gcagaagcgt tcgcggcgcc gtggcactcg     120
ggcaggtggc ttctgcacgc cccgctatat gagctgcctc cgngatgcag agccacccag     180 ccccaccccct gcgggccccc ctcggtgccc ctggcaggat gacgccttca tccgagggg     240 cggcccaggc aagggcaagg agctggggct gcggcagtg gccctgggct tcgaggatac     300
cgaggtgaca acgacagcgg gcgggacggc tgaggtggcg cccgacgcgg tgcccaggag     360
tgggcgatcc tgctggcgcc gtctggtgca ggtgttccag tcgaagcagt tccgttcggc     420
caagctggag cgcctgtacc agcggtactt cttccagatg aaccagagca gcctgacgct     480
gctgatggcg gtgctggtgc tgctcacagc ggtgctgctg gctttccacg ccgcacccgc     540
ccgccctcag cctgcctatg tggcactgtt ggcctgtgcc gccgcccgt tcgtggggct     600 catggtggtg tgtaaccggc atagcttccg ccaggactcc atgtgggtgg tgagttacgt     660
ggtgctgggc atcctggcgg cagtgcaggt cgggggcgct ctcgcagcag acccgcgcag     720
cccctctgcg ggcctctggt gccctgtgtt ctttgtctac atcgcctaca cgctcctccc     780
catccgcatg cgggctgccg tcctcagcgg cctgggcctc tccaccttgc atttgatctt     840
ggcctggcaa cttaaccgtg gtgatgcctt cctctggagg cagctcggtg ccaatgtgct     900
gctgttcctc tgcaccaacg tcattggcat ctgcacacac tatccagcag aggtgtctca     960
gcgccaggcc tttcaggaga cccgcggtta catccaggcc cggctccacc tgcagcatga    1020
gaatcggcag caggagcggc tgctgctgtc ggtattgccc cagcacgtcg ccatggagat    1080
gaaagaagac atcaacacaa aaaagaaga catgatgttc cacaagatct acatacagaa    1140
gcatgacaat gtcagcatcc tgtttgcaga cattgagggc ttcaccagcc tggcatccca    1200
gtgcactgcg caggagctgg tcatgaccct gaatgagctc tttgcccggt ttgacaagct    1260
ggctgcggag aatcactgcc tgaggatcaa gatcttgggg gactgttact actgtgtgtc    1320
agggctgccg gaggcccggg ccgaccatgc ccactgctgt gtggagatgg gggtagacat    1380
gattgaggcc atctcgctgg tacgtgaggt gacaggtgtg aatgtgaaca tgcgcgtggg    1440
catccacagc gggcgcgtgc actgcggcgt ccttggcttg cggaaatggc agttcgatgt    1500
gtggtccaat gatgtgaccc tggccaacca catggaggca ggaggccggg ctggccgcat    1560
ccacatcact cgggcaacac tgcagtacct gaacggggac tacgaggtgg agccaggccg    1620
tggtggcgag cgcaacgcgt acctcaagga gcagcacatt gagactttcc tcatcctggg    1680
cgccagccag aaacggaaag aggagaaggc catgctggcc aagctgcagc ggactcgggc    1740
caactccatg gaagggctga tgccgcgctg ggttcctgat cgtgccttct cccggaccaa    1800
ggactccaag gccttccgcc agatgggcat tgatgattcc agcaaagaca ccgggggcac    1860
ccaagatgcc ctgaaccctg aggatgaggt ggatgagttc ctgagccgtg ccatcgatgc    1920
ccgcagcatt gatcagctgc ggaaggacca tgtgcgccgg tttctgctca ccttccagag    1980
agaggatctt gagaagaagt actcccggaa ggtggatccc cgcttcggag cctacgttgc    2040
ctgtgccctg ttggtcttct gcttcatctg cttcatccag cttctcatct tcccacactc    2100 cacccctgatg cttgggatct atgccagcat cttcctgctg ctgctaatca ccgtgctgat    2160
ctgtgctgtg tactcctgtg gttctctgtt ccctaaggcc ctgcaacgtc tgtcccgcag    2220
cattgtccgc tcacgggcac atagcaccgc agttggcatc ttttccgtcc tgcttgtgtt    2280
tacttctgcc attgccaaca tgttcacctg taaccacacc ccatacggga gctgtgcagc    2340
ccggatgctg aatttaacac tgctgacat cactgcctgc acctgcagc agctcaatta    2400
```

```
ctctctgggc ctggatgctc ccctgtgtga gggcaccatg cccacctgca gctttcctga    2460
gtacttcatc gggaacatgc tgctgagtct cttggccagc tctgtcttcc tgcacatcag    2520
cagcatcggg aagttggcca tgatctttgt cttgggctc atctatttgg tgctgcttct    2580
gctgggtccc ccagccacca tctttgacaa ctatgaccta ctgcttggcg tccatggctt    2640
ggcttcttcc aatgagacct tgatgggct ggactgtcca gctgcaggga gggtggccct    2700
caaatatatg accctgtga ttctgctggt gtttgcgctg cgctgtatc tgcatgctca    2760 gcaggtggag tcgactgccc gcctagactt cctctggaaa ctacaggcaa caggggagaa    2820
ggaggagatg gaggagctac aggcatacaa ccggaggctg ctgcataaca ttctgcccaa    2880
ggacgtggcg gcccacttcc tggcccggga gcgccgcaat gatgaactct actatcagtc    2940
gtgtgagtgt gtggctgtta tgtttgcctc cattgccaac ttctctgagt tctatgtgga    3000
gctggaggca aacaatgagg gtgtcgagtg cctgcggctg ctcaacgaga tcatcgctga    3060
ctttgatgag attatcagcg aggagcggtt ccggcagctg gaaaagatca agacgattgg    3120
tagcacctac atggctgcct cagggctgaa cgccagcacc tacgatcagg tgggccgctc    3180
ccacatcact gccctggctg actacgccat gcggctcatg gagcagatga agcacatcaa    3240
tgagcactcc ttcaacaatt ccagatgaa gattgggctg aacatgggcc cagtcgtggc    3300
aggtgtcatc ggggctcgga agccacagta tgacatctgg gggaacacag tgaatgtctc    3360
tagtcgtatg gacagcacgg gggtccccga ccgaatccag gtgaccacgg acctgtacca    3420
ggttctagct gccaagggct accagctgga gtgtcgaggg gtggtcaagg tgaagggcaa    3480 ggggggagatg accacctact tcctcaatgg ggggcccagc agttaacagg ggaattc     3537

<210> SEQ ID NO 15
<211> LENGTH: 3537
<212> TYPE: DNA
<213> ORGANISM: mus musculus
<220> FEATURE:
<221> NAME/KEY: misc_feature
<222> LOCATION: (163)..(163)
<223> OTHER INFORMATION: n is a, c, g, or t

<400> SEQUENCE: 15
gaattcgccc ttcggcagca tgtcatggtt tagtggcctc ctggtcccta aagtggatga     60
acggaaaaca gcctgggtg aacgcaatgg gcagaagcgt tcgcggcgcc gtggcactcg    120
ggcaggtggc ttctgcacgc cccgctatat gagctgcctc cgngatgcag agccacccag    180 ccccaccct gcgggccccc ctcggtgccc ctggcaggat gacgccttca tccggagggg    240
cggcccaggc aagggcaagg agctggggct gcgggcagtg gccctgggct tcgaggatac    300
cgaggtgaca acgacagcgg gcgggacggc tgaggtggcg cccgacgcgg tgcccaggag    360
tgggcgatcc tgctggcgcc gtctggtgca ggtgttccag tcgaagcagt tccgttcggc    420
caagctggag cgcctgtacc agcggtactt cttccagatg aaccagagca gcctgacgct    480
gctgatggcg gtgctggtgc tgctcacagc ggtgctgctg gctttccacg ccgcacccgc    540
ccgccctcag cctgcctatg tggcactgtt ggcctgtgcc gccgccctgt tcgtggggct    600
catggtggtg tgtaaccggc atagcttccg ccaggactcc atgtgggtgg tgagttacgt    660
ggtgctgggc atcctggcgg cagtgcaggt cggggggcgct ctcgcagcag acccgcgcag    720 ccctctgcg ggcctctggt gccctgtgtt ctttgtctac atcgcctaca cgctcctccc    780
catccgcatg cgggctgccg tcctcagcgg cctgggcctc tccaccttgc atttgatctt    840
```

```
ggcctggcaa cttaaccgtg gtgatgcctt cctctggagg cagctcggtg ccaatgtgct    900
gctgttcctc tgcaccaacg tcattggcat ctgcacacac tatccagcag aggtgtctca    960
gcgccaggcc tttcaggaga cccgcggtta catccaggcc cggctccacc tgcagcatga   1020
gaatcggcag caggagcggc tgctgctgtc ggtattgccc cagcacgtcg ccatggagat   1080
gaaagaagac atcaacacaa aaaagaagaa catgatgttc cacaagatct acatacagaa   1140
gcatgacaat gtcagcatcc tgtttgcaga cattgagggc ttcaccagcc tggcatccca   1200
gtgcactgcg caggagctgg tcatgaccct gaatgagctc tttgcccggt tgacaagct    1260
ggctgcggag aatcactgcc tgaggatcaa gatcttgggg gactgttact actgtgtgtc   1320
agggctgccg gaggcccggg ccgaccatgc ccactgctgt gtggagatgg gggtagacat   1380
gattgaggcc atctcgctgg tacgtgaggt gacaggtgtg aatgtgaaca tgcgcgtggg   1440
catccacagc gggcgcgtgc actgcggcgt ccttggcttg cggaaatggc agttcgatgt   1500
gtggtccaat gatgtgaccc tggccaacca catggaggca ggaggccggg ctggccgcat   1560
ccacatcact cgggcaacac tgcagtacct gaacggggac tacgaggtgg agccaggccg   1620
tggtggcgag cgcaacgcgt acctcaagga gcagcacatt gagactttcc tcatcctggg   1680
cgccagccag aaacggaaag aggagaaggc catgctggcc aagctgcagc ggactcgggc   1740
caactccatg gaagggctga tgccgcgctg ggttcctgat cgtgccttct cccggaccaa   1800
ggactccaag gccttccgcc agatgggcat tgatgattcc agcaaagaca accggggcac   1860
ccaagatgcc ctgaaccctg aggatgaggt ggatgagttc ctgagccgtg ccatcgatgc   1920
ccgcagcatt gatcagctgc ggaaggacca tgtgcgccgg tttctgctca ccttccagag   1980
agaggatctt gagaagaagt actcccggaa ggtggatccc cgcttcggag cctacgttgc   2040
ctgtgccctg ttggtcttct gcttcatctg cttcatccag cttctcatct cccacactc    2100
caccctgatg cttgggatct atgccagcat cttcctgctg ctgctaatca ccgtgctgat   2160
ctgtgctgtg tactcctgtg gttctctgtt ccctaaggcc ctgcaacgtc tgtcccgcag   2220
cattgtccgc tcacgggcac atagcaccgc agttggcatc ttttccgtcc tgcttgtgtt   2280
tacttctgcc attgccaaca tgttcacctg taaccacacc cccatacgga gctgtgcagc   2340
ccggatgctg aatttaacac tgctgacat cactgcctgc cacctgcagc agctcaatta    2400
ctctctgggc ctggatgctc ccctgtgtga gggcaccatg cccacctgca gctttcctga   2460
gtacttcatc gggaacatgc tgctgagtct cttggccagc tctgtcttcc tgcacatcag   2520
cagcatcggg aagttggcca tgatctttgt cttggggctc atctatttgg tgctgcttct   2580
gctgggtccc ccagccacca tctttgacaa ctatgaccta ctgcttggcg tccatggctt   2640
ggcttcttcc aatgagacct tgatgggctg gactgtcca gctgcaggga gggtggccct    2700
caaatatatg acccctgtga ttctgctggt gtttgcgctg gcgctgtatc tgcatgctca   2760
gcaggtggag tcgactgccc gcctagactt cctctggaaa ctacaggcaa caggggagaa   2820
ggaggagatg gaggagctac aggcatacaa ccggaggctg ctgcataaca ttctgcccaa   2880
ggacgtggcg gcccacttcc tggcccggga gcgccgcaat gatgaactct actatcagtc   2940
gtgtgagtgt gtggctgtta tgtttgcctc cattgccaac ttctctgagt ctatgtgga    3000
gctggaggca aacaatgagg gtgtcgagtg cctgcggctg ctcaacgaga tcatcgctga   3060
ctttgatgag attatcagcg aggagcggtt ccggcagctg gaaaagatca agacgattgg   3120
tagcacctac atggctgcct cagggctgaa cgccagcacc tacgatcagg tgggccgctc   3180
ccacatcact gccctggctg actacgccat gcggctcatg gagcagatga agcacatcaa   3240
```

```
tgagcactcc ttcaacaatt tccagatgaa gattgggctg aacatgggcc cagtcgtggc    3300
aggtgtcatc ggggctcgga agccacagta tgacatctgg gggaacacag tgaatgtctc    3360
tagtcgtatg gacagcacgg gggtccccga ccgaatccag gtgaccacgg acctgtacca    3420
ggttctagct gccaagggct accagctgga gtgtcgaggg gtggtcaagg tgaagggcaa    3480
gggggagatg accacctact tcctcaatgg ggccccagc agttaacagg ggaattc        3537
```

<210> SEQ ID NO 16
<211> LENGTH: 1166
<212> TYPE: PRT
<213> ORGANISM: mus musculus

<400> SEQUENCE: 16

```
Met Ser Trp Phe Ser Gly Leu Leu Val Pro Lys Val Asp Glu Arg Lys
1               5                   10                  15

Thr Ala Trp Gly Glu Arg Asn Gly Gln Lys Arg Pro Arg His Ala Asn
            20                  25                  30

Arg Ala Ser Gly Phe Cys Ala Pro Arg Tyr Met Ser Cys Leu Lys Asn
        35                  40                  45

Ala Glu Pro Pro Ser Pro Thr Pro Ala Ala His Thr Arg Cys Pro Trp
    50                  55                  60

Gln Asp Glu Ala Phe Ile Arg Arg Ala Gly Pro Gly Arg Gly Val Glu
65                  70                  75                  80

Leu Gly Leu Arg Ser Val Ala Leu Gly Phe Asp Asp Thr Glu Val Thr
                85                  90                  95

Thr Pro Met Gly Thr Ala Glu Val Ala Pro Asp Thr Ser Pro Arg Ser
            100                 105                 110

Gly Pro Ser Cys Trp His Arg Leu Val Gln Val Phe Gln Ser Lys Gln
        115                 120                 125

Phe Arg Ser Ala Lys Leu Glu Arg Leu Tyr Gln Arg Tyr Phe Phe Gln
    130                 135                 140

Met Asn Gln Ser Ser Leu Thr Leu Leu Met Ala Val Leu Val Leu Leu
145                 150                 155                 160

Met Ala Val Leu Leu Thr Phe His Ala Ala Pro Ala Gln Pro Gln Pro
                165                 170                 175

Ala Tyr Val Ala Leu Leu Thr Cys Ala Ser Val Leu Phe Val Val Leu
            180                 185                 190

Met Val Val Cys Asn Arg His Ser Phe Arg Gln Asp Ser Met Trp Val
        195                 200                 205

Val Ser Tyr Val Val Leu Gly Ile Leu Ala Ala Val Gln Val Gly Gly
    210                 215                 220

Ala Leu Ala Ala Asn Pro His Ser Pro Ser Ala Gly Leu Trp Cys Pro
225                 230                 235                 240

Val Phe Phe Val Tyr Ile Thr Tyr Thr Leu Leu Pro Ile Arg Met Arg
                245                 250                 255

Ala Ala Val Leu Ser Gly Leu Gly Leu Ser Thr Leu His Leu Ile Leu
            260                 265                 270

Ala Trp Gln Leu Asn Ser Ser Asp Pro Phe Leu Trp Lys Gln Leu Gly
        275                 280                 285

Ala Asn Val Val Leu Phe Leu Cys Thr Asn Ala Ile Gly Val Cys Thr
    290                 295                 300

His Tyr Pro Ala Glu Val Ser Gln Arg Gln Ala Phe Gln Glu Thr Arg
305                 310                 315                 320
```

-continued

Gly Tyr Ile Gln Ala Arg Leu His Leu Gln His Glu Asn Arg Gln Gln
            325                 330                 335

Glu Arg Leu Leu Leu Ser Val Leu Pro Gln His Val Ala Met Glu Met
            340                 345                 350

Lys Glu Asp Ile Asn Thr Lys Lys Glu Asp Met Met Phe His Lys Ile
            355                 360                 365

Tyr Ile Gln Lys His Asp Asn Val Ser Ile Leu Phe Ala Asp Ile Glu
            370                 375                 380

Gly Phe Thr Ser Leu Ala Ser Gln Cys Thr Ala Gln Glu Leu Val Met
385                 390                 395                 400

Thr Leu Asn Glu Leu Phe Ala Arg Phe Asp Lys Leu Ala Ala Glu Asn
            405                 410                 415

His Cys Leu Arg Ile Lys Ile Leu Gly Asp Cys Tyr Tyr Cys Val Ser
            420                 425                 430

Gly Leu Pro Glu Ala Arg Ala Asp His Ala His Cys Cys Val Glu Met
            435                 440                 445

Gly Val Asp Met Ile Glu Ala Ile Ser Leu Val Arg Glu Val Thr Gly
            450                 455                 460

Val Asn Val Asn Met Arg Val Gly Ile His Ser Gly Arg Val His Cys
465                 470                 475                 480

Gly Val Leu Gly Leu Arg Lys Trp Gln Phe Asp Val Trp Ser Asn Asp
            485                 490                 495

Val Thr Leu Ala Asn His Met Glu Ala Gly Gly Arg Ala Gly Arg Ile
            500                 505                 510

His Ile Thr Arg Ala Thr Leu Gln Tyr Leu Asn Gly Asp Tyr Glu Val
            515                 520                 525

Glu Pro Gly Arg Gly Gly Glu Arg Asn Ala Tyr Leu Lys Glu Gln Cys
            530                 535                 540

Ile Glu Thr Phe Leu Ile Leu Gly Ala Ser Gln Lys Arg Lys Glu Glu
545                 550                 555                 560

Lys Ala Met Leu Ala Lys Leu Gln Arg Thr Arg Ala Asn Ser Met Glu
            565                 570                 575

Gly Leu Met Pro Arg Trp Val Pro Asp Arg Ala Phe Ser Arg Thr Lys
            580                 585                 590

Asp Ser Lys Ala Phe Arg Gln Met Gly Ile Asp Asp Ser Ser Lys Asp
            595                 600                 605

Asn Arg Gly Ala Gln Asp Ala Leu Asn Pro Glu Asp Glu Val Asp Glu
            610                 615                 620

Phe Leu Gly Arg Ala Ile Asp Ala Arg Ser Ile Asp Gln Leu Arg Lys
625                 630                 635                 640

Asp His Val Arg Arg Phe Leu Leu Thr Phe Gln Arg Glu Asp Leu Glu
            645                 650                 655

Lys Lys Tyr Ser Arg Lys Val Asp Pro Arg Phe Gly Ala Tyr Val Ala
            660                 665                 670

Cys Ala Leu Leu Val Phe Cys Phe Ile Cys Phe Ile Gln Leu Leu Val
            675                 680                 685

Phe Pro Tyr Ser Thr Leu Ile Leu Gly Ile Tyr Ala Ala Ile Phe Leu
            690                 695                 700

Leu Leu Leu Val Thr Val Leu Ile Cys Ala Val Cys Ser Cys Gly Ser
705                 710                 715                 720

Phe Phe Pro Lys Ala Leu Gln Arg Leu Ser Arg Asn Ile Val Arg Ser
            725                 730                 735

Arg Val His Ser Thr Ala Val Gly Ile Phe Ser Val Leu Leu Val Phe

```
                740             745             750
Ile Ser Ala Ile Ala Asn Met Phe Thr Cys Asn His Thr Pro Ile Arg
    755             760             765
Thr Cys Ala Ala Arg Met Leu Asn Leu Thr Pro Ala Asp Val Thr Ala
    770             775             780
Cys His Leu Gln Gln Leu Asn Tyr Ser Leu Gly Leu Asp Ala Pro Leu
785             790             795             800
Cys Glu Gly Thr Ala Pro Thr Cys Ser Phe Pro Glu Tyr Phe Val Gly
                805             810             815
Asn Val Leu Leu Ser Leu Leu Ala Ser Ser Val Phe Leu His Ile Ser
            820             825             830
Ser Ile Gly Lys Leu Ala Met Thr Phe Ile Leu Gly Phe Thr Tyr Leu
        835             840             845
Val Leu Leu Leu Gly Pro Pro Ala Ala Ile Phe Asp Asn Tyr Asp
    850             855             860
Leu Leu Leu Gly Val His Gly Leu Ala Ser Ser Asn Glu Thr Phe Asp
865             870             875             880
Gly Leu Asp Cys Pro Ala Val Gly Arg Val Ala Leu Lys Tyr Met Thr
                885             890             895
Pro Val Ile Leu Leu Val Phe Ala Leu Ala Leu Tyr Leu His Ala Gln
            900             905             910
Gln Val Glu Ser Thr Ala Arg Leu Asp Phe Leu Trp Lys Leu Gln Ala
        915             920             925
Thr Gly Glu Lys Glu Glu Met Glu Glu Leu Gln Ala Tyr Asn Arg Arg
    930             935             940
Leu Leu His Asn Ile Leu Pro Lys Asp Val Ala Ala His Phe Leu Ala
945             950             955             960
Arg Glu Arg Arg Asn Asp Glu Leu Tyr Tyr Gln Ser Cys Glu Cys Val
                965             970             975
Ala Val Met Phe Ala Ser Ile Ala Asn Phe Ser Glu Phe Tyr Val Glu
            980             985             990
Leu Glu Ala Asn Asn Glu Gly Val Glu Cys Leu Arg Leu Leu Asn Glu
        995             1000            1005
Ile Ile Ala Asp Phe Asp Glu Ile Ile Ser Glu Glu Arg Phe Arg
    1010            1015            1020
Gln Leu Glu Lys Ile Lys Thr Ile Gly Ser Thr Tyr Met Ala Ala
    1025            1030            1035
Ser Gly Leu Asn Ala Ser Thr Tyr Asp Gln Val Gly Arg Ser His
    1040            1045            1050
Ile Thr Ala Leu Ala Asp Tyr Ala Met Arg Leu Met Glu Gln Met
    1055            1060            1065
Lys His Ile Asn Glu His Ser Phe Asn Asn Phe Gln Met Lys Ile
    1070            1075            1080
Gly Leu Asn Met Gly Pro Val Val Ala Gly Val Ile Gly Ala Arg
    1085            1090            1095
Lys Pro Gln Tyr Asp Ile Trp Gly Asn Thr Val Asn Val Ser Ser
    1100            1105            1110
Arg Met Asp Ser Thr Gly Val Pro Asp Arg Ile Gln Val Thr Thr
    1115            1120            1125
Asp Leu Tyr Gln Val Leu Ala Ala Lys Gly Tyr Gln Leu Glu Cys
    1130            1135            1140
Arg Gly Val Val Lys Val Lys Gly Lys Gly Glu Met Thr Thr Tyr
    1145            1150            1155
```

```
Phe Leu Asn Gly Gly Pro Ser Ser
    1160                1165

<210> SEQ ID NO 17
<211> LENGTH: 1166
<212> TYPE: PRT
<213> ORGANISM: mus musculus

<400> SEQUENCE: 17

Met Ser Trp Phe Ser Gly Leu Leu Val Pro Lys Val Asp Glu Arg Lys
1               5                   10                  15

Thr Ala Trp Gly Glu Arg Asn Gly Gln Lys Arg Pro Arg His Ala Asn
            20                  25                  30

Arg Ala Ser Gly Phe Cys Ala Pro Arg Tyr Met Ser Cys Leu Lys Asn
        35                  40                  45

Ala Glu Pro Pro Ser Pro Thr Pro Ala Ala His Thr Arg Cys Pro Trp
    50                  55                  60

Gln Asp Glu Ala Phe Ile Arg Arg Ala Gly Pro Gly Arg Gly Val Glu
65                  70                  75                  80

Leu Gly Leu Arg Ser Val Ala Leu Gly Phe Asp Asp Thr Glu Val Thr
                85                  90                  95

Thr Pro Met Gly Thr Ala Glu Val Ala Pro Asp Thr Ser Pro Arg Ser
            100                 105                 110

Gly Pro Ser Cys Trp His Arg Leu Val Gln Val Phe Gln Ser Lys Gln
        115                 120                 125

Phe Arg Ser Ala Lys Leu Glu Arg Leu Tyr Gln Arg Tyr Phe Phe Gln
    130                 135                 140

Met Asn Gln Ser Ser Leu Thr Leu Leu Met Ala Val Leu Val Leu Leu
145                 150                 155                 160

Met Ala Val Leu Leu Thr Phe His Ala Ala Pro Ala Gln Pro Gln Pro
                165                 170                 175

Ala Tyr Val Ala Leu Leu Thr Cys Ala Ser Val Leu Phe Val Val Leu
            180                 185                 190

Met Val Val Cys Asn Arg His Ser Phe Arg Gln Asp Ser Met Trp Val
        195                 200                 205

Val Ser Tyr Val Val Leu Gly Ile Leu Ala Ala Val Gln Val Gly Gly
    210                 215                 220

Ala Leu Ala Ala Asn Pro His Ser Pro Ser Ala Gly Leu Trp Cys Pro
225                 230                 235                 240

Val Phe Phe Val Tyr Ile Thr Tyr Thr Leu Leu Pro Ile Arg Met Arg
                245                 250                 255

Ala Ala Val Leu Ser Gly Leu Gly Leu Ser Thr Leu His Leu Ile Leu
            260                 265                 270

Ala Trp Gln Leu Asn Ser Ser Asp Pro Phe Leu Trp Lys Gln Leu Gly
        275                 280                 285

Ala Asn Val Val Leu Phe Leu Cys Thr Asn Ala Ile Gly Val Cys Thr
    290                 295                 300

His Tyr Pro Ala Glu Val Ser Gln Arg Gln Ala Phe Gln Glu Thr Arg
305                 310                 315                 320

Gly Tyr Ile Gln Ala Arg Leu His Leu Gln His Glu Asn Arg Gln Gln
                325                 330                 335

Glu Arg Leu Leu Leu Ser Val Leu Pro Gln His Val Ala Met Glu Met
            340                 345                 350

Lys Glu Asp Ile Asn Thr Lys Lys Glu Asp Met Met Phe His Lys Ile
```

```
                355                 360                 365
Tyr Ile Gln Lys His Asp Asn Val Ser Ile Leu Phe Ala Asp Ile Glu
370                 375                 380
Gly Phe Thr Ser Leu Ala Ser Gln Cys Thr Ala Gln Glu Leu Val Met
385                 390                 395                 400
Thr Leu Asn Glu Leu Phe Ala Arg Phe Asp Lys Leu Ala Ala Glu Asn
                405                 410                 415
His Cys Leu Arg Ile Lys Ile Leu Gly Ala Cys Tyr Tyr Cys Val Ser
                420                 425                 430
Gly Leu Pro Glu Ala Arg Ala Asp His Ala His Cys Cys Val Glu Met
                435                 440                 445
Gly Val Asp Met Ile Glu Ala Ile Ser Leu Val Arg Glu Val Thr Gly
                450                 455                 460
Val Asn Val Asn Met Arg Val Gly Ile His Ser Gly Arg Val His Cys
465                 470                 475                 480
Gly Val Leu Gly Leu Arg Lys Trp Gln Phe Asp Val Trp Ser Asn Asp
                485                 490                 495
Val Thr Leu Ala Asn His Met Glu Ala Gly Gly Arg Ala Gly Arg Ile
                500                 505                 510
His Ile Thr Arg Ala Thr Leu Gln Tyr Leu Asn Gly Asp Tyr Glu Val
                515                 520                 525
Glu Pro Gly Arg Gly Gly Glu Arg Asn Ala Tyr Leu Lys Glu Gln Cys
530                 535                 540
Ile Glu Thr Phe Leu Ile Leu Gly Ala Ser Gln Lys Arg Lys Glu Glu
545                 550                 555                 560
Lys Ala Met Leu Ala Lys Leu Gln Arg Thr Arg Ala Asn Ser Met Glu
                565                 570                 575
Gly Leu Met Pro Arg Trp Val Pro Asp Arg Ala Phe Ser Arg Thr Lys
                580                 585                 590
Asp Ser Lys Ala Phe Arg Gln Met Gly Ile Asp Asp Ser Ser Lys Asp
                595                 600                 605
Asn Arg Gly Ala Gln Asp Ala Leu Asn Pro Glu Asp Glu Val Asp Glu
                610                 615                 620
Phe Leu Gly Arg Ala Ile Asp Ala Arg Ser Ile Asp Gln Leu Arg Lys
625                 630                 635                 640
Asp His Val Arg Arg Phe Leu Leu Thr Phe Gln Arg Glu Asp Leu Glu
                645                 650                 655
Lys Lys Tyr Ser Arg Lys Val Asp Pro Arg Phe Gly Ala Tyr Val Ala
                660                 665                 670
Cys Ala Leu Leu Val Phe Cys Phe Ile Cys Phe Ile Gln Leu Leu Val
                675                 680                 685
Phe Pro Tyr Ser Thr Leu Ile Leu Gly Ile Tyr Ala Ala Ile Phe Leu
                690                 695                 700
Leu Leu Leu Val Thr Val Leu Ile Cys Ala Val Cys Ser Cys Gly Ser
705                 710                 715                 720
Phe Phe Pro Lys Ala Leu Gln Arg Leu Ser Arg Asn Ile Val Arg Ser
                725                 730                 735
Arg Val His Ser Thr Ala Val Gly Ile Phe Ser Val Leu Leu Val Phe
                740                 745                 750
Ile Ser Ala Ile Ala Asn Met Phe Thr Cys Asn His Thr Pro Ile Arg
                755                 760                 765
Thr Cys Ala Ala Arg Met Leu Asn Leu Thr Pro Ala Asp Val Thr Ala
                770                 775                 780
```

```
Cys His Leu Gln Gln Leu Asn Tyr Ser Leu Gly Leu Asp Ala Pro Leu
785                 790                 795                 800

Cys Glu Gly Thr Ala Pro Thr Cys Ser Phe Pro Glu Tyr Phe Val Gly
                805                 810                 815

Asn Val Leu Leu Ser Leu Leu Ala Ser Ser Val Phe Leu His Ile Ser
            820                 825                 830

Ser Ile Gly Lys Leu Ala Met Thr Phe Ile Leu Gly Phe Thr Tyr Leu
        835                 840                 845

Val Leu Leu Leu Gly Pro Pro Ala Ala Ile Phe Asp Asn Tyr Asp
850                 855                 860

Leu Leu Leu Gly Val His Gly Leu Ala Ser Ser Asn Glu Thr Phe Asp
865                 870                 875                 880

Gly Leu Asp Cys Pro Ala Val Gly Arg Val Ala Leu Lys Tyr Met Thr
                885                 890                 895

Pro Val Ile Leu Leu Val Phe Ala Leu Ala Leu Tyr Leu His Ala Gln
            900                 905                 910

Gln Val Glu Ser Thr Ala Arg Leu Asp Phe Leu Trp Lys Leu Gln Ala
        915                 920                 925

Thr Gly Glu Lys Glu Glu Met Glu Glu Leu Gln Ala Tyr Asn Arg Arg
930                 935                 940

Leu Leu His Asn Ile Leu Pro Lys Asp Val Ala Ala His Phe Leu Ala
945                 950                 955                 960

Arg Glu Arg Arg Asn Asp Glu Leu Tyr Tyr Gln Ser Cys Glu Cys Val
                965                 970                 975

Ala Val Met Phe Ala Ser Ile Ala Asn Phe Ser Glu Phe Tyr Val Glu
            980                 985                 990

Leu Glu Ala Asn Asn Glu Gly Val Glu Cys Leu Arg Leu Leu Asn Glu
        995                 1000                1005

Ile Ile Ala Asp Phe Asp Glu Ile Ile Ser Glu Arg Phe Arg
1010                1015                1020

Gln Leu Glu Lys Ile Lys Thr Ile Gly Ser Thr Tyr Met Ala Ala
1025                1030                1035

Ser Gly Leu Asn Ala Ser Thr Tyr Asp Gln Val Gly Arg Ser His
1040                1045                1050

Ile Thr Ala Leu Ala Asp Tyr Ala Met Arg Leu Met Glu Gln Met
1055                1060                1065

Lys His Ile Asn Glu His Ser Phe Asn Asn Phe Gln Met Lys Ile
1070                1075                1080

Gly Leu Asn Met Gly Pro Val Val Ala Gly Val Ile Gly Ala Arg
1085                1090                1095

Lys Pro Gln Tyr Asp Ile Trp Gly Asn Thr Val Asn Val Ser Ser
1100                1105                1110

Arg Met Asp Ser Thr Gly Val Pro Asp Arg Ile Gln Val Thr Thr
1115                1120                1125

Asp Leu Tyr Gln Val Leu Ala Ala Lys Gly Tyr Gln Leu Glu Cys
1130                1135                1140

Arg Gly Val Val Lys Val Lys Gly Lys Gly Glu Met Thr Thr Tyr
1145                1150                1155

Phe Leu Asn Gly Gly Pro Ser Ser
1160                1165
```